United States Patent
Lee et al.

(10) Patent No.: US 9,403,795 B2
(45) Date of Patent: Aug. 2, 2016

(54) CARBAZOLE-BASED COMPOUND AND ORGANIC LIGHT-EMITTING DIODE COMPRISING THE SAME

(75) Inventors: Sun-Young Lee, Yongin (KR); Yoon-Hyun Kwak, Yongin (KR); Bum-Woo Park, Yongin (KR); Dae-Yup Shin, Yongin (KR); Kwan-Hee Lee, Yongin (KR); Hye-In Jeong, Yongin (KR); Sam-Il Kho, Yongin (KR); Mie-Hwa Park, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 0 days.

(21) Appl. No.: 13/362,841

(22) Filed: Jan. 31, 2012

(65) Prior Publication Data

US 2013/0032788 A1    Feb. 7, 2013

(30) Foreign Application Priority Data

Aug. 5, 2011  (KR) .................. 10-2011-0078200
Jan. 6, 2012  (KR) .................. 10-2012-0002021

(51) Int. Cl.
*H01L 51/50*   (2006.01)
*C07D 401/12*  (2006.01)
(Continued)

(52) U.S. Cl.
CPC ............ *C07D 401/12* (2013.01); *C07D 401/14* (2013.01); *C07D 403/12* (2013.01); *C07D 487/04* (2013.01)

(58) Field of Classification Search
USPC .................. 428/690, 917; 313/504, 505, 506; 257/40, E51.05, E51.026, E51.032; 548/440, 304.1, 418
See application file for complete search history.

(56) References Cited

U.S. PATENT DOCUMENTS 5,635,308 A  6/1997  Inoue et al.
5,645,948 A  7/1997  Shi et al.
(Continued)

FOREIGN PATENT DOCUMENTS

JP    08012600       1/1996
JP    2000003782     1/2000
(Continued)

OTHER PUBLICATIONS

Sundholm et al., An initio determination of the induced ring current in aromatic molecules, 1999, Phys. Chem. Chem. Phys., vol. 1, p. 3429-3435.*

(Continued)

*Primary Examiner* — Gregory Clark
(74) *Attorney, Agent, or Firm* — Robert E. Bushnell, Esq.

(57) ABSTRACT

A carbazole-based compound of Formula 1 and an organic light-emitting diode including the same. The carbazole-based compound represented by Formula 1 has a triarylamine structure, wherein at least one of $R_1$ to $R_5$ is essentially a nitrogen-containing group. Thus, the carbazole-based compound has high glass transition temperature and/or high melting point, and is stable during electron injection, and when interposed between a pair of electrodes (anode and cathode) of an organic light-emitting diode, the carbazole-based compound may have excellent thermal resistance against Joule's heat generated in organic layers between the pair of electrodes, between the organic layers, or between the organic layer and the electrode during an operation of the organic light-emitting diode.

22 Claims, 3 Drawing Sheets

(51) Int. Cl.
  *C07D 403/12* (2006.01)
  *C07D 401/14* (2006.01)
  *C07D 487/04* (2006.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 7,737,627 | B2 | 6/2010 | Hwang et al. |
| 2004/0170863 | A1* | 9/2004 | Kim ............... C07C 13/72 428/690 |
| 2005/0106419 | A1 | 5/2005 | Endoh et al. |
| 2005/0121667 | A1 | 6/2005 | Kuehl et al. |
| 2005/0221124 | A1* | 10/2005 | Hwang et al. ............... 428/690 |
| 2006/0020136 | A1 | 1/2006 | Hwang et al. |
| 2006/0115680 | A1 | 6/2006 | Hwang et al. |
| 2006/0240280 | A1* | 10/2006 | Liao et al. ............... 428/690 |
| 2007/0054151 | A1* | 3/2007 | Iwakuma et al. ............... 428/690 |
| 2007/0231503 | A1 | 10/2007 | Hwang et al. |
| 2009/0096357 | A1* | 4/2009 | Lee et al. ............... 313/504 |
| 2009/0096375 | A1* | 4/2009 | Yamashita ............... H01J 9/02 313/582 |
| 2011/0049484 | A1* | 3/2011 | Kim ............... C07D 209/08 257/40 |
| 2011/0193074 | A1* | 8/2011 | Lee ............... H01L 51/0072 257/40 |
| 2011/0233525 | A1 | 9/2011 | Terao et al. |
| 2011/0240979 | A1* | 10/2011 | Kim ............... C07D 487/04 257/40 |
| 2012/0161612 | A1 | 6/2012 | Kim et al. |

FOREIGN PATENT DOCUMENTS

| | | |
|---|---|---|
| JP | 2005166641 | 6/2005 |
| KR | 1020050054427 | 6/2005 |
| KR | 1020050097670 | 10/2005 |
| KR | 1020100003624 | 1/2010 |
| KR | 1020100039815 | 4/2010 |
| KR | 1020100043994 | 4/2010 |
| KR | 1020100094819 | 8/2010 |
| KR | 1020100095504 | 8/2010 |
| KR | 101007516 B1 | 1/2011 |
| KR | 102011088898 A | 8/2011 |
| WO | 2011031086 A2 | 3/2011 |

OTHER PUBLICATIONS

Sakamoto et al., Synthesis, Characterization, and Electron-Transport Property of Perfluorinated Phenylene Dendrimers, J. Am. Chem. Soc. (2000) 122, pp. 1832-1833.

Adachi et al., Confinement of charge carriers and molecular excitons within 5nm thick emitter layer in organic electroluminescent devices with a double heterostructure, Appl. Phys. Lett (1990) 57, 531, pp. 531-533.

Tang et al., Organic electroluminescent diodes, Appl. Phys. Lett. (1987) 51, 913, pp. 913-915.

Yamaguchi et al., Diphenylamino-Substituted 2,5-Diarylsiloles for Single-Layer Organic Electroluminescent Devices, Chem. Lett. (2001) pp. 98-99.

Korean Office Action issued by Korean Intellectual Property Office on Oct. 7, 2015 in connection with Korean Patent Application No. 10-2012-0002021 and Request for Entry attached herewith.

Japanese Office Action mailed on Mar. 1, 2016 issued by JPO in connection with Japanese Patent Application No. 2012-174393 which claims present invention and Request for Entry attached herewith.

* cited by examiner

CARBAZOLE-BASED COMPOUND AND ORGANIC LIGHT-EMITTING DIODE COMPRISING THE SAME

CLAIM OF PRIORITY

This application claims the benefit of Korean Patent Application Nos. 10-2011-0078200, filed on Aug. 5, 2011 and 10-2012-0002021 filed on Jan. 6, 2012 in the Korean Intellectual Property Office, the disclosures of each of which are incorporated herein in their entirety by reference.

BACKGROUND OF THE INVENTION

1. Field of the Invention

The present invention relates to carbazole-based compounds and an organic light-emitting diode including the carbazole-based compounds.

2. Description of the Related Art

Organic light-emitting diodes (OLEDs), which are self-emitting devices, have advantages such as a wide viewing angle, excellent contrast, quick response, high brightness, excellent driving voltage characteristics, and the ability to provide multicolored images.

A general organic light-emitting diode has a structure including a substrate, an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an organic light-emitting diode having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to the ground state, light is emitted.

SUMMARY OF THE INVENTION

The present invention provides carbazole-based compounds and an organic light-emitting diode including the carbazole-based compounds.

According to an aspect of the present invention, there is provided carbazole-based compounds represented by Formula 1 below:

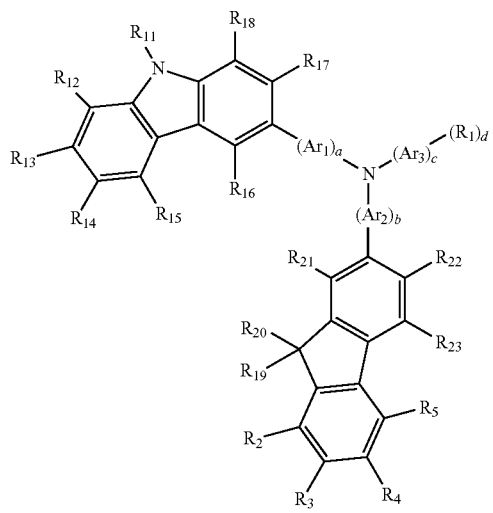

Formula 1 wherein $Ar_1$ to $Ar_3$ are each independently a substituted or unsubstituted $C_5$-$C_{60}$ arylene group;

a and b are each independently an integer from 0 to 5;

c is an integer from 1 to 5;

$R_1$ to $R_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —$Si(R_{31})(R_{32})(R_{33})$, —$N(R_{34})(R_{35})$ or a nitrogen-containing group, wherein at least one of $R_1$ to $R_5$ is a nitrogen-containing group;

d is an integer from 0 to 5;

$R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —$Si(R_{36})(R_{37})(R_{38})$, or —$N(R_{39})(R_{40})$;

$R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group; and the nitrogen-containing group is a 5-membered aromatic ring group, a 6-membered aromatic ring group, a 9-membered aromatic ring group in which a 5-membered aromatic ring group and a 6-membered aromatic ring group are fused to each other, which include at least one nitrogen atom as a ring atom.

According to another aspect of the present invention, there is provided an organic light-emitting diode comprising a first electrode; a second electrode disposed opposite to the first electrode; and an organic layer interposed between the first electrode and the second electrode, wherein the organic layer comprises a carbazole-based compound according to claim 1 as a single material or in a mixture of different materials.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
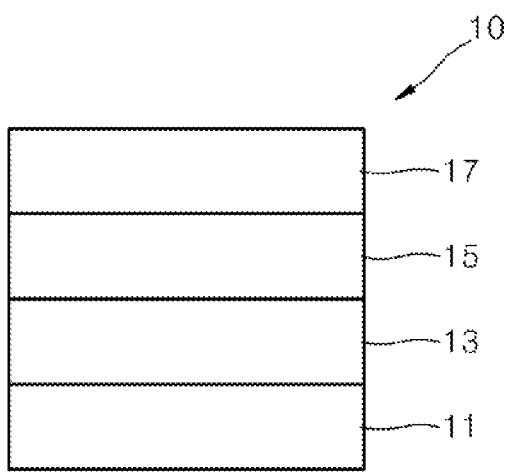
FIG. 1 is a schematic cross-sectional view of an organic light-emitting diode according to an embodiment of the present invention.

Hereinafter, the present invention will now be described more fully with reference to the accompanying drawings, in which exemplary embodiments of the invention are shown.

A carbazole-based compound according to an embodiment of the present invention is represented by Formula 1 below.

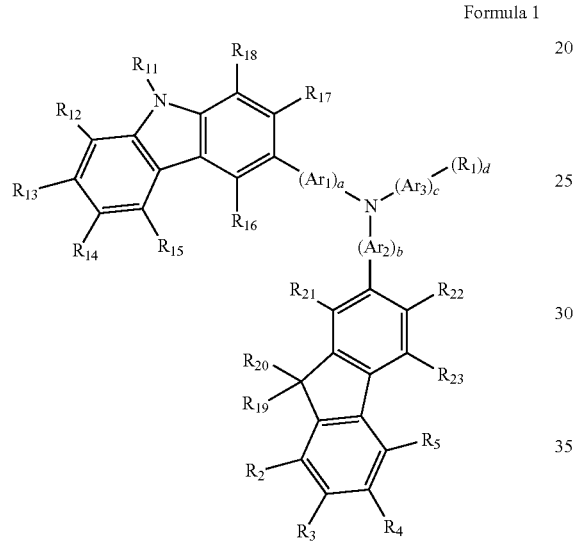

Formula 1

In Formula 1, $Ar_1$ to $Ar_3$ are each independently a substituted or unsubstituted $C_5$-$C_{60}$ arylene group.

For example, $Ar_1$ to $Ar_3$ may be each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyranylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group.

For example, $Ar_1$ to $Ar_3$ may be each independently one of Formulae 2A to 2I below, but are not limited thereto.

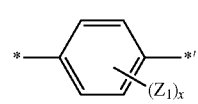

Formula 2A

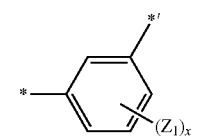

Formula 2B

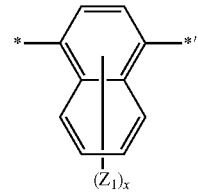

Formula 2C

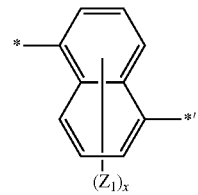

Formula 2D

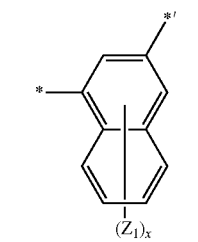

Formula 2E

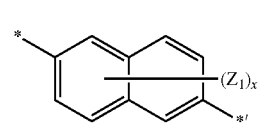

Formula 2F

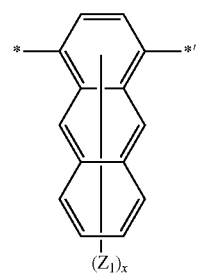

Formula 2G

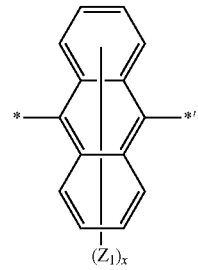

Formula 2H

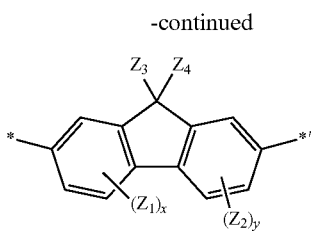

Formula 2I

In Formulae 2A to 2I, $Z_1$ to $Z_4$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($Q_1$)($Q_2$)($Q_3$), or —N($Q_4$)($Q_5$). In this regard, $Q_1$ to $Q_5$ may be each independently a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a substituted or to unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group.

For example, in Formulae 2A to 2I, $Z_1$ to $Z_4$ may be each independently a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_5$-$C_{20}$ aryl group.

For example, in Formulae 2A to 2I, $Z_1$ to $Z_4$ may be each independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid or a salt thereof; a $C_1$-$C_{10}$ alkyl group; e.g., a methyl group, an ethyl group, a propyl group, a butyl group, a pentyl group, and a hexyl group; a $C_1$-$C_{10}$ alkoxy group, e.g., a methoxy group, an ethoxy group, a propoxy group, a butoxy group, and a pentoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a $C_1$-$C_{10}$ alkyl group, and a $C_1$-$C_{10}$ alkoxy group.

According to an embodiment of the present invention, in Formulae 2A to 2I, $Z_1$ to $Z_4$ may be each independently a hydrogen atom, a methyl group, or a phenyl group.

In Formulae 2A to 2I, x is an integer from 1 to 8, and y is an integer from 1 to 3. The x and y may vary within the ranges described above according to the structures of Formulae 2A to 2I. If x is 2 or greater, $Z_1$s may be the same or different from each other. If y is 2 or greater, $Z_2$s may be the same or different from each other.

In Formulae 2A to 2I, * is a binding site with nitrogen positioned at the center of Formula 1, *' is a binding with $R_1$, a carbazole ring, or a fluorene ring in Formula 1.

In Formula 1, a and b may be each independently an integer from 0 to 5. If a and/or b is 0, the carbazole ring and/or fluorene ring of Formula 1 may be directly bound to the nitrogen positioned at the center of Formula 1. For example, a and b may be 0, 1 or 2, but are not limited thereto. If a is 2 or greater, $Ar_1$s may be the same or different from each other. If b is 2 or greater, $Ar_2$s may be the same or different from each other.

In Formula 1, c may be an integer from 1 to 5. That is, in Formula 1, Ar a always exists. For example, c may be 1 or 2, but is not limited thereto. If c is 2 or greater, $Ar_3$s may be the same or different from each other.

In Formula 1, $R_1$ to $R_5$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{31}$)($R_{32}$)($R_{33}$), —N($R_{34}$)($R_{35}$), or a nitrogen-containing group, wherein at least one of $R_1$ to $R_5$ is a nitrogen-containing group.

For example, $R_1$ to $R_5$ may be each independently a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, a substituted or unsubstituted $C_5$-$C_{20}$ aryl group, or a nitrogen-containing group, wherein at least one of $R_1$ to $R_5$ is a nitrogen-containing group.

The nitrogen-containing group is a 5-membered aromatic ring group, a 6-membered aromatic ring group, a 9-membered aromatic ring group in which a 5-membered aromatic ring group and a 6-membered aromatic ring group are fused to each other, which include at least one nitrogen atom as a ring atom. The term "ring atom" used herein indicates an atom forming a ring.

For example, the nitrogen-containing group may be one of Formulae 3A to 3M below.

Formula 3A
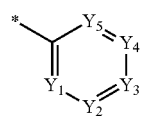

Formula 3B
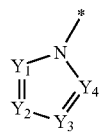

Formula 3C
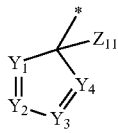

Formula 3D
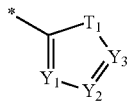

Formula 3E
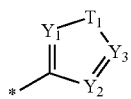

Formula 3F
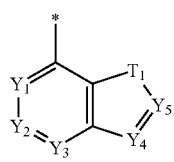

Formula 3G
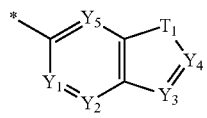

Formula 3H
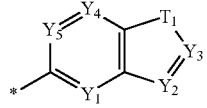

Formula 3I
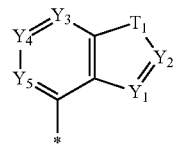

Formula 3J
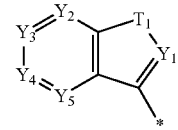

Formula 3K
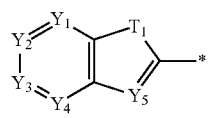

Formula 3L
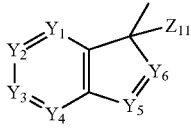

Formula 3M
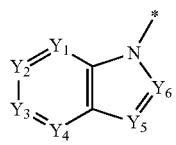

In Formulae 3A to 3M, $Y_1$ to $Y_6$ may be each independently =N— or =C($Z_{12}$)—, and $T_1$ may be —N($Z_{13}$)— or —C($Z_{14}$)($Z_{15}$)—. That is, the ring atom of the nitrogen-containing group may be nitrogen or carbon.

In Formulae 3A to 3M, $Z_{11}$ to $Z_{15}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group.

For example, $Z_{11}$ to $Z_{15}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_5$-$C_{20}$ aryl group.

In addition, $Z_{11}$ to $Z_{15}$ may be each independently a hydrogen atom; a deuterium atom; a halogen atom; a hydroxyl group; a cyano group; a nitro group; an amino group; an amidino group; a hydrazine; a hydrazone; a carboxyl group of a salt thereof; a sulfonic acid group or a salt thereof; a phosphoric acid or a salt thereof; a $C_1$-$C_{10}$ alkyl group, e.g., a methyl group, an ethyl group, a propyl group, a butyl group, a pentyl group, and a hexyl group; a $C_1$-$C_{10}$ alkoxy group, e.g., a methoxy group, an ethoxy group, a propoxy group, a butoxy group, and a pentoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a $C_1$-$C_{10}$ alkyl group, and a $C_1$-$C_{10}$ alkoxy group, but are not limited thereto.

* is a chemical bond.

For example, the nitrogen-containing group may be one of Formulae 4A to 4P below.

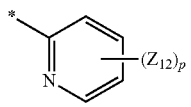
Formula 4A

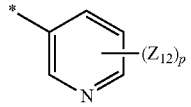
Formula 4B

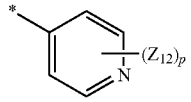
Formula 4C

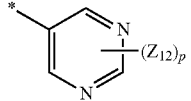
Formula 4D

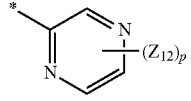
Formula 4E

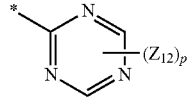
Formula 4F

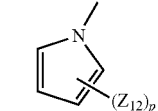
Formula 4G

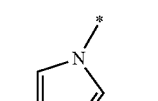
Formula 4H

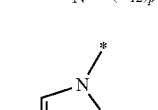
Formula 4I

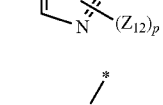
Formula 4J

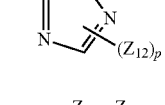
Formula 4K

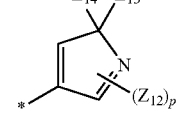

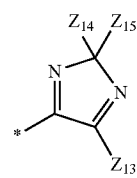
Formula 4L

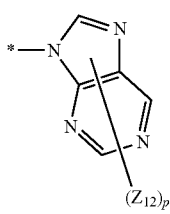
Formula 4M

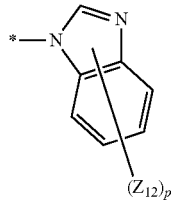
Formula 4N

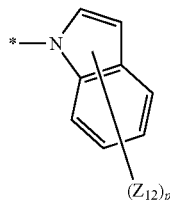
Formula 4O

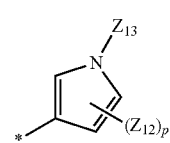
Formula 4P

In Formulae 4A to 4P, $Z_{12}$, $Z_{13}$, $Z_{14}$, and $Z_{15}$ are defined as described above.

According to an embodiment of the present invention, $Z_{12}$, $Z_{13}$, $Z_{14}$, and $Z_{15}$ may be a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a methyl group, an ethyl group, a propyl group, or a butyl group. For example, in Formulae 4A to 4P, $Z_{12}$, $Z_{13}$, $Z_{14}$, and $Z_{15}$ may be hydrogen.

In Formulae 4A to 4P, p is an integer from 1 to 6. The p may vary within the range described above according to the structures of Formulae 4A to 4P. If p is 2 or greater, $Z_{12}$s may be the same or different from each other. * is a chemical bond.

In Formula 1, d may be an integer from 0 to 5. For example, d may be 0, 1, or 2, but is not limited thereto. The d may vary within the range described above according to the structure of $Ar_3$. If d is 2 or greater, $R_1$s may be the same or different from each other.

In Formula 1, $R_{11}$ to $R_{23}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{36}$)($R_{37}$)($R_{38}$), or —N($R_{39}$)($R_{40}$).

For example, $R_1$, to $R_{23}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_5$-$C_{20}$ aryl group.

In addition, $R_{11}$ to $R_{23}$ may be each independently a hydrogen atom; a deuterium atom; a halogen atom; a hydroxyl group; a cyano group; a nitro group; an amino group; an amidino group; a hydrazine; a hydrazone; a carboxyl group or a salt thereof, a sulfonic acid group or a salt thereof; a phosphoric acid or a salt thereof; a $C_1$-$C_{10}$ alkyl group, e.g., a methyl group, an ethyl group, a propyl group, a butyl group, a pentyl group, and a hexyl group; a $C_1$-$C_{10}$ alkoxy group, e.g., a methoxy group, an ethoxy group, a propoxy group, a butoxy group, and a pentoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof; a phosphoric acid or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a $C_1$-$C_{10}$ alkyl group, and a $C_1$-$C_{10}$ alkoxy group, but are not limited thereto.

For example, in Formula 1, $R_{12}$ to $R_{18}$ and $R_{21}$ to $R_{23}$ may be each independently a hydrogen atom, a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, or a phosphoric acid or a salt thereof, and $R_{11}$, $R_{19}$ and $R_{20}$ may be each independently a hydrogen atom, a methyl group, an ethyl group, a propyl group, a butyl group, a pentyl group, a phenyl group, a naphthyl group, an anthryl group, a fluorenyl group, or a pyrenyl group, but are not limited thereto.

In —Si($R_{31}$)($R_{32}$)($R_{33}$), —N($R_{34}$)($R_{35}$), —Si($R_{36}$)($R_{37}$)($R_{38}$), and —N($R_{39}$)($R_{40}$), $R_{31}$ to $R_{40}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted to $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group.

For example, $R_{31}$ to $R_{40}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl is group, a substituted or unsubstituted $C_1$-$C_{10}$ alkoxy group, or a substituted or unsubstituted $C_5$-$C_{20}$ aryl group.

In addition, $R_{31}$ to $R_{40}$ may be each independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid or a salt thereof; a $C_1$-$C_{10}$ alkyl group, e.g., a methyl group, an ethyl group, a propyl group, a butyl group, a pentyl group, and a hexyl group; a $C_1$-$C_{10}$ alkoxy group, e.g., a methoxy group, an ethoxy group, a propoxy group, a butoxy group, and a pentoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a $C_1$-$C_{10}$ alkyl group, and a $C_1$-$C_{10}$ alkoxy group, but are not limited thereto.

$Q_1$ to $Q_5$ are defined as described above with reference to $R_{31}$.

In Formula 1, $R_1$ may be a nitrogen-containing group, and c and d may be each independently 1 or 2. Alternatively, in Formula 1, at least one of $R_2$ to $R_5$ may be a nitrogen-containing group.

The carbazole-based compound may be represented by one of Formulae 1A to 1K below.

Formula 1A

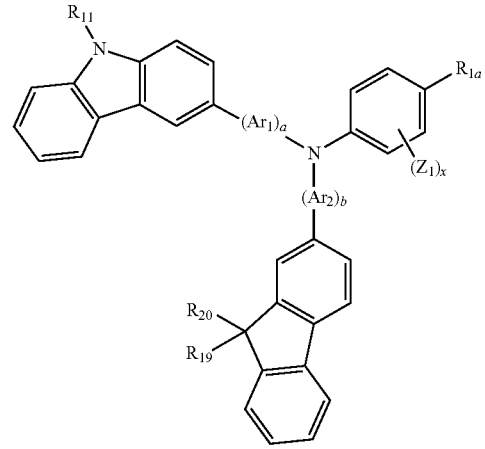

Formula 1B
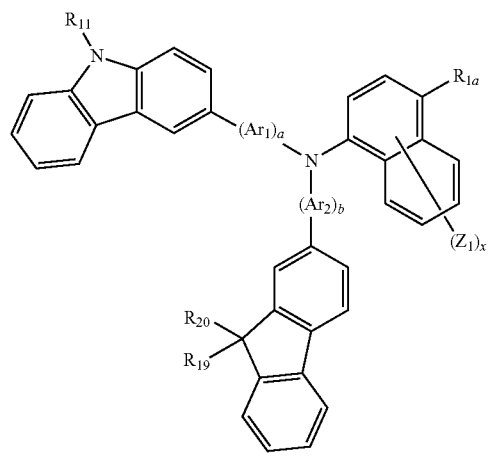
Formula 1E
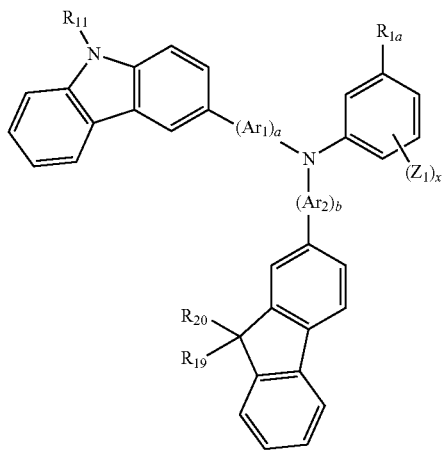
Formula 1C
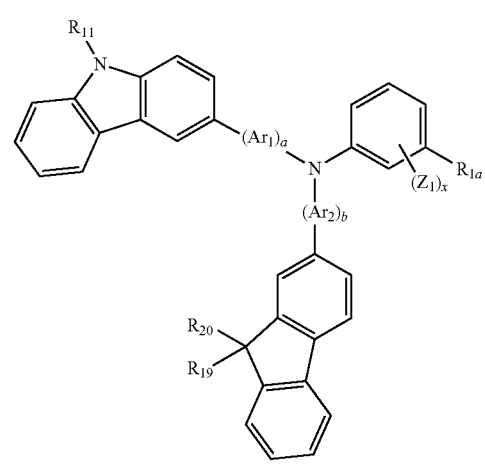
Formula 1F
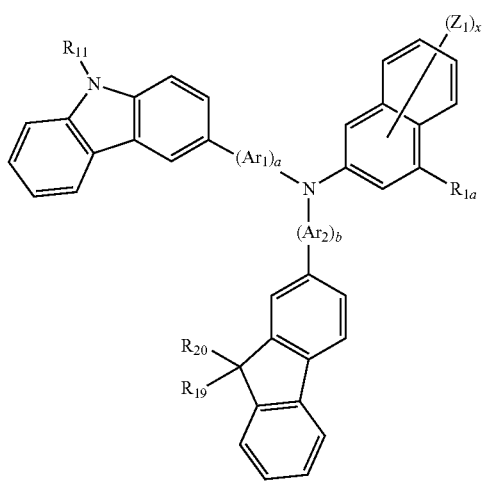
Formula 1D
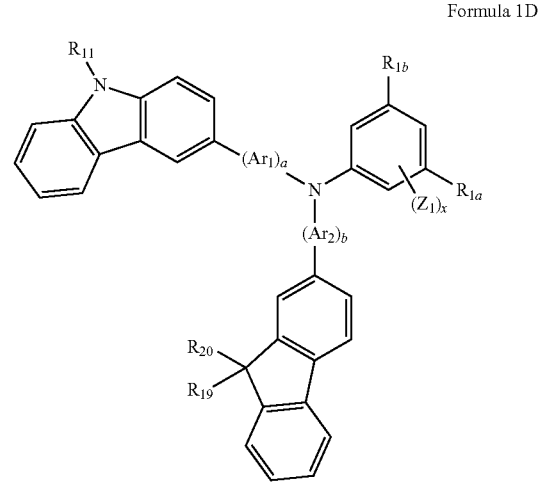
Formula 1G
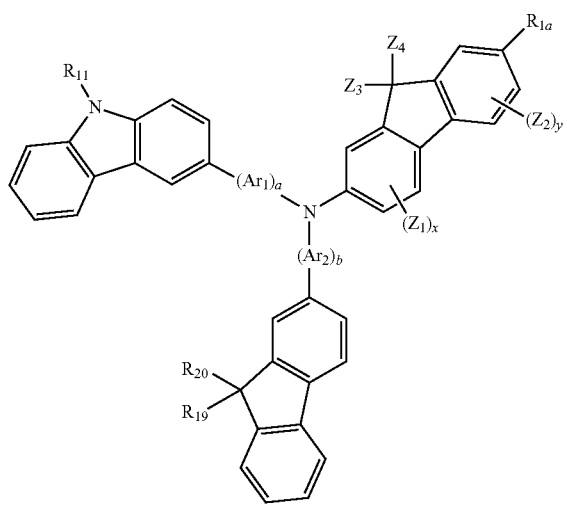

Formula 1H

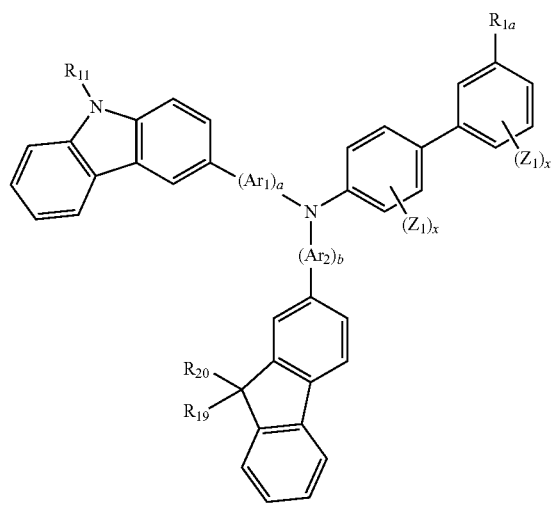

Formula 1I

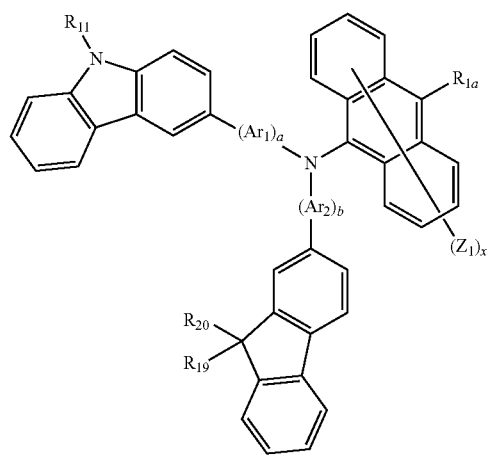

Formula 1J

Formula 1K

In Formulae 1A to 1K, $Ar_1$, $Ar_2$, a, b, $R_{11}$, $R_{19}$, $R_{20}$, $Z_1$ to $Z_4$, $Q_1$ to $Q_5$, x, and y are defined as described above.

In Formulae 1A to 1K, $R_{1a}$, $R_{1b}$, and $R_3$ are the nitrogen-containing group as described above. The nitrogen-containing group is defined as described above.

For example, in Formulae 1A to 1K, $Ar_1$ and $Ar_2$ may be each independently one of Formulae 2A to 2I; a and b may be each independently 0 or 1; $R_{1a}$, $R_{1b}$, and $R_3$ may be each independently one of Formulae 3A to 3M; $Z_1$ to $Z_4$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_5$-$C_{20}$ aryl group; x may be an integer from 1 to 8, but are not limited thereto.

The carbazole-based compound represented by Formula 1 may be any one compound of Compounds 1 to 33 below, but is not limited thereto.

1

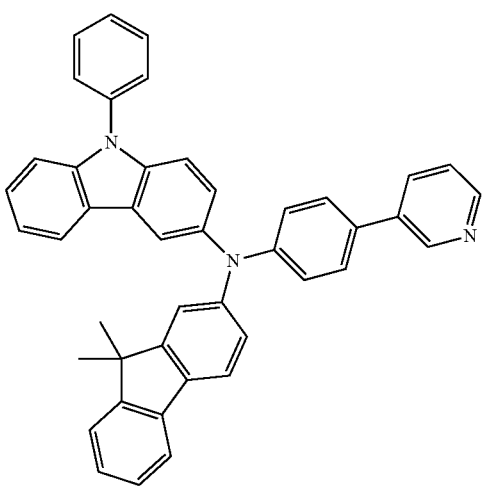

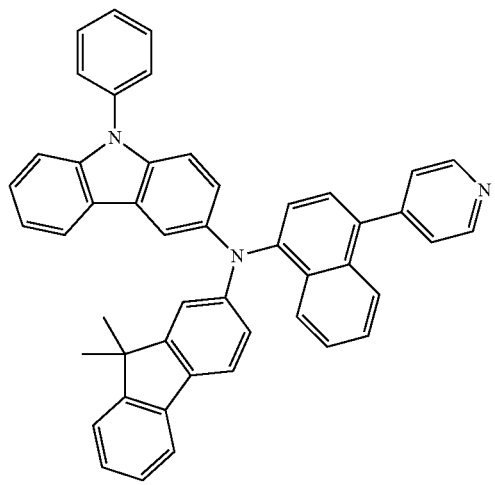
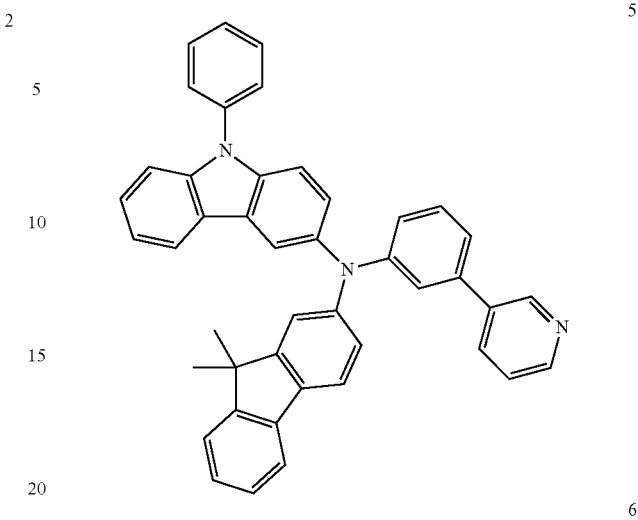
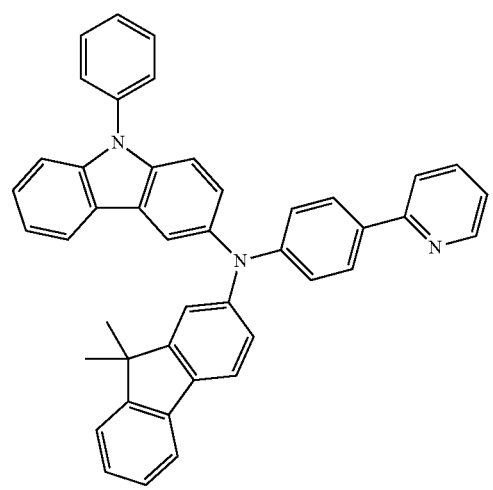
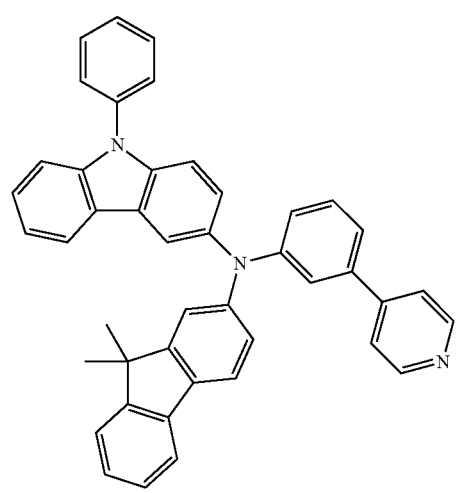
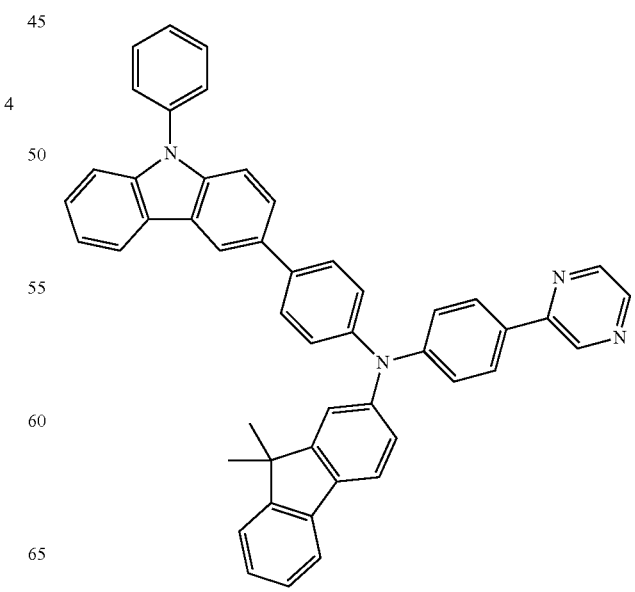

8
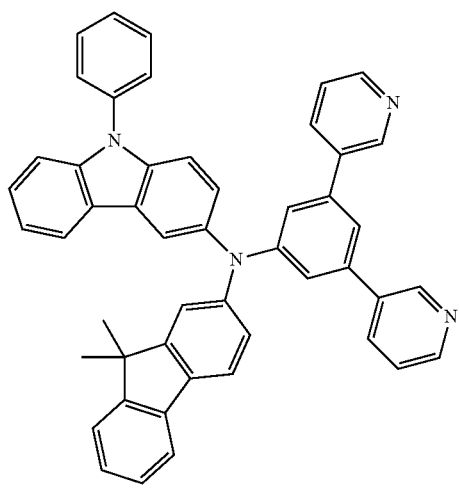
11
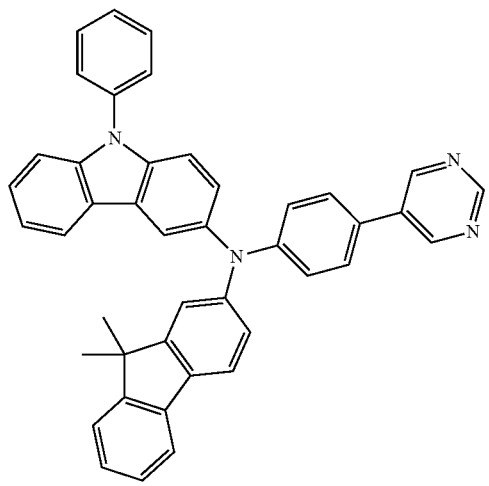
9
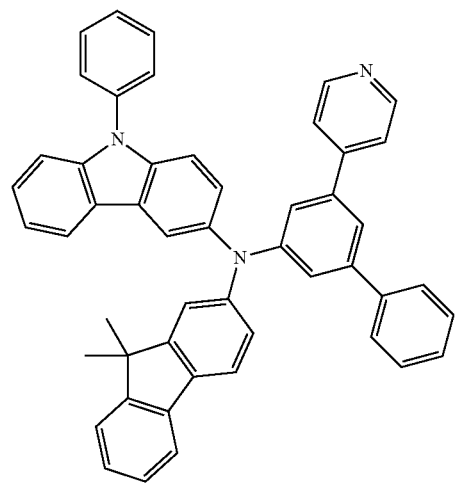
12
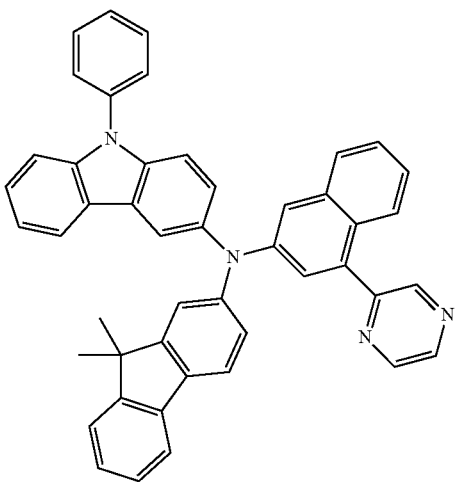
10
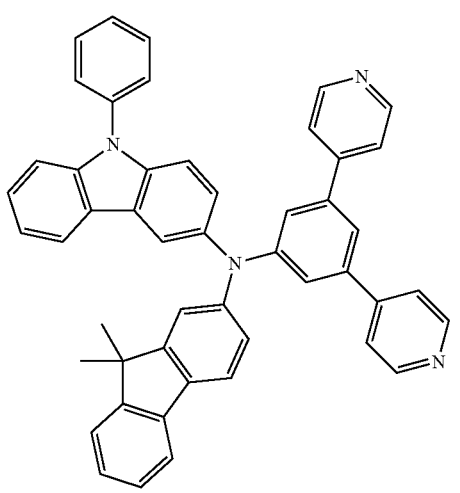
13
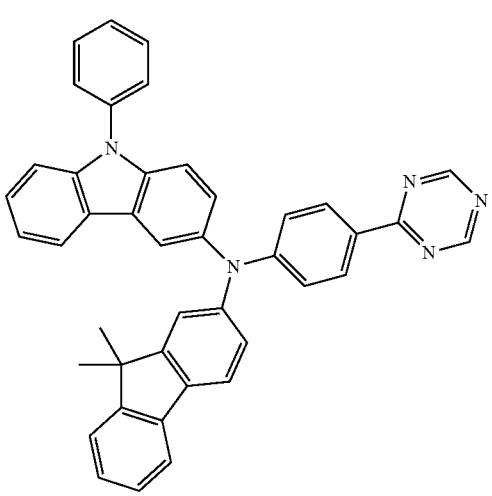

14
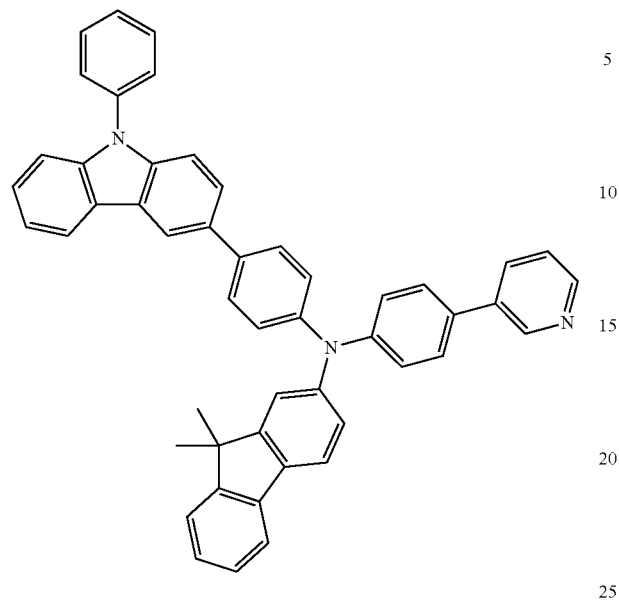
16
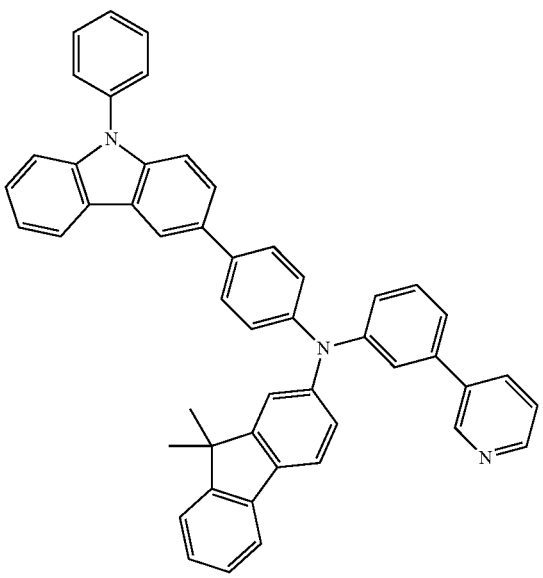
15
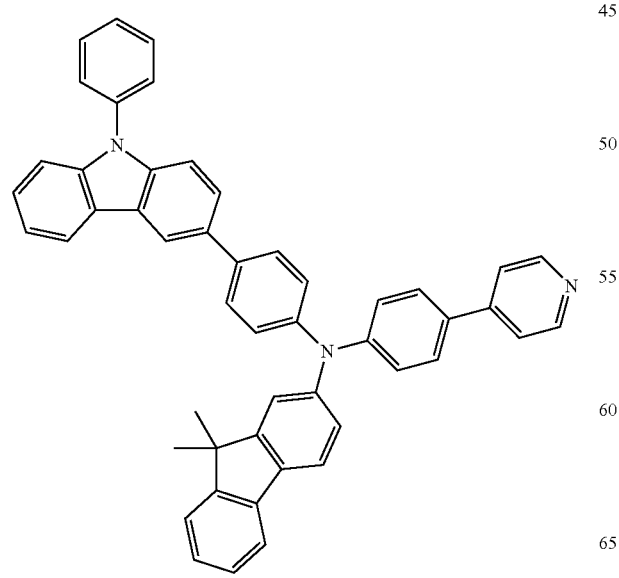
17
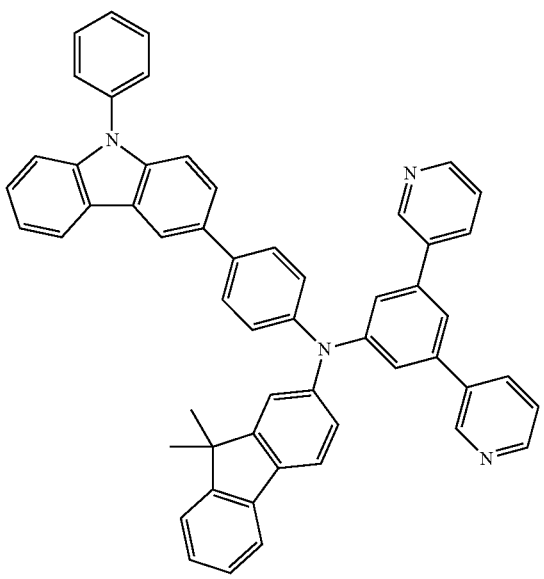

US 9,403,795 B2

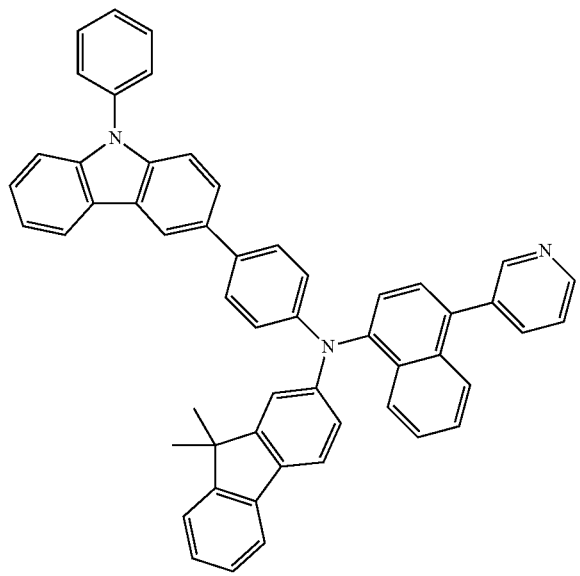
23
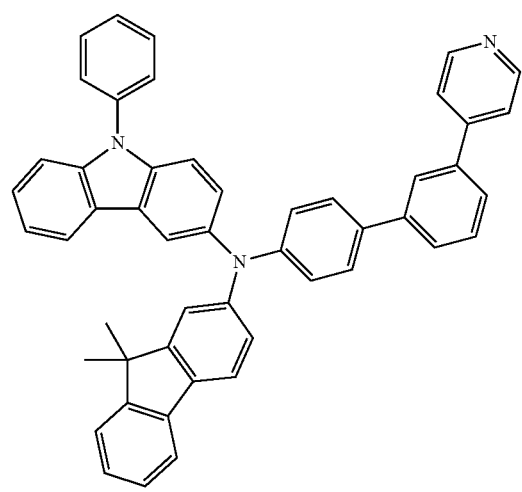
24
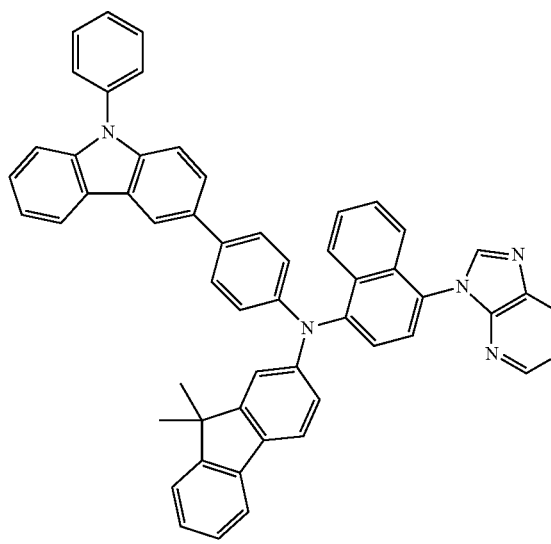
25
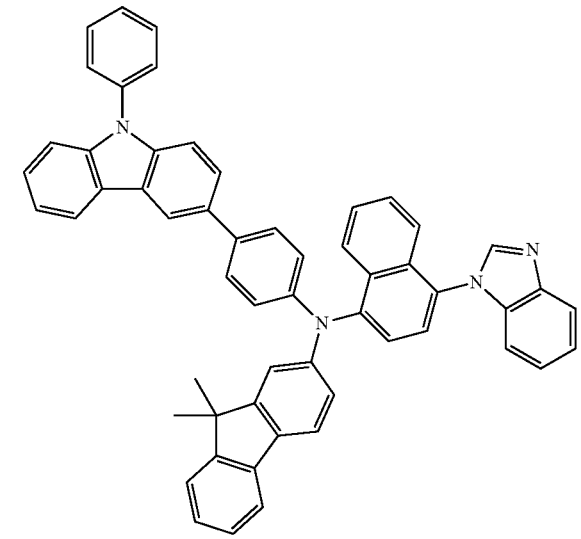
26
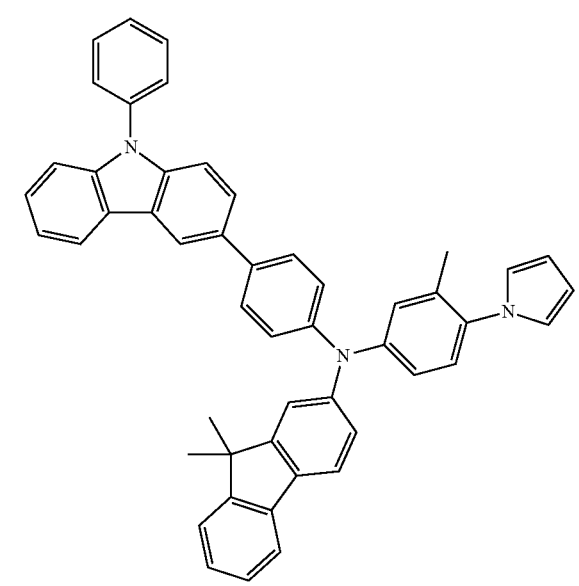
27

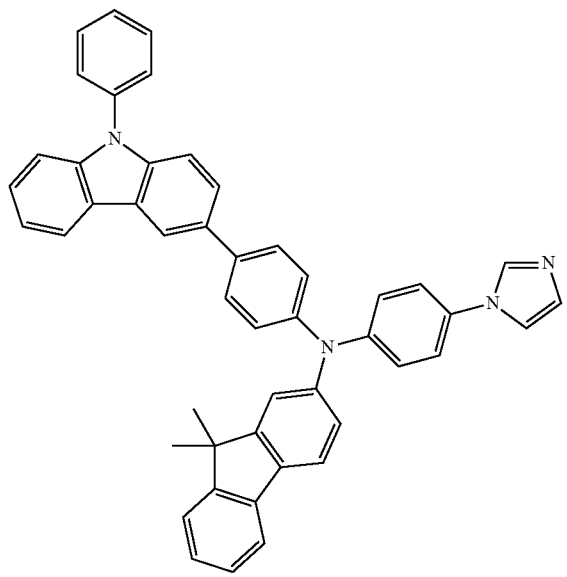
28
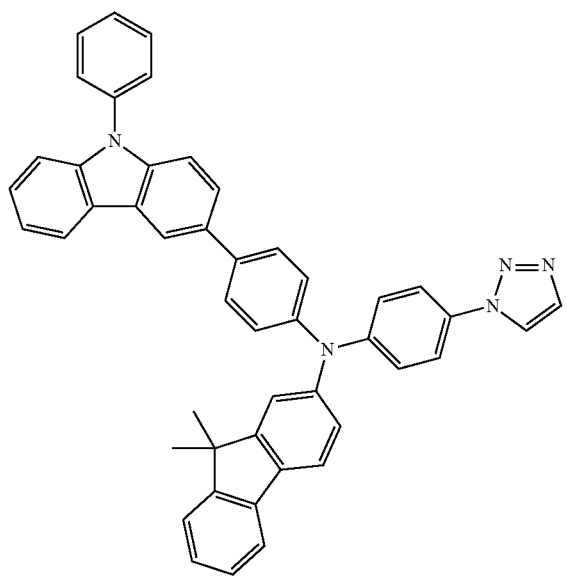
29
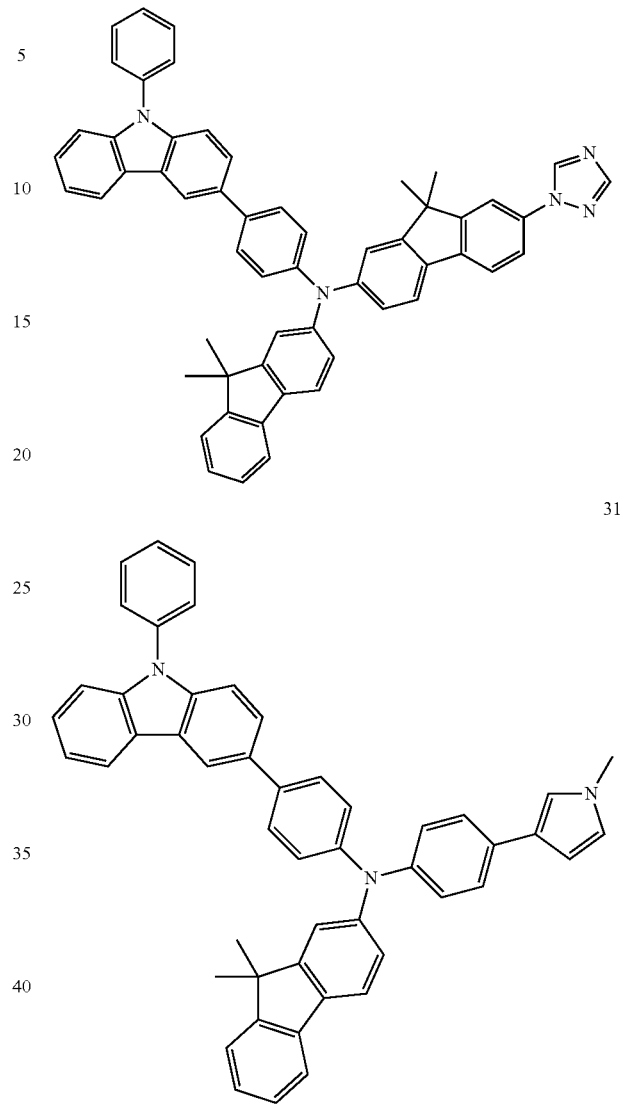
30
31
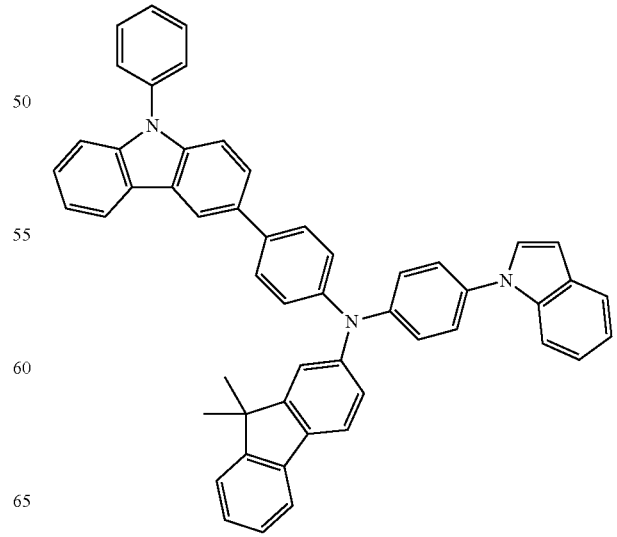
32

33

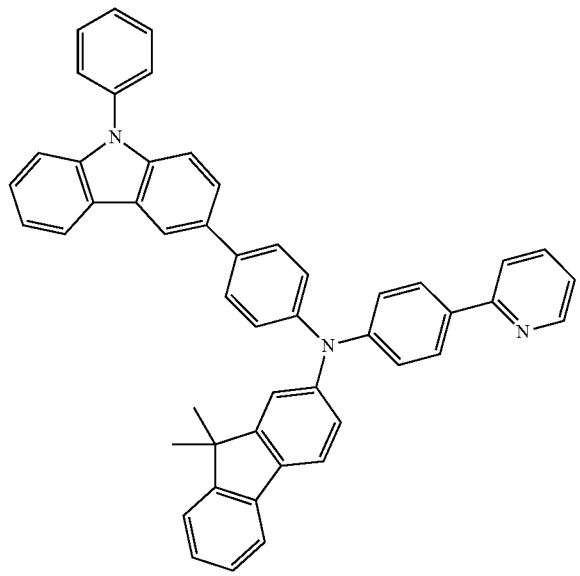

The carbazole-based compound represented by Formula 1 has a triarylamine structure, wherein at least one of $R_1$ to $R_5$ is essentially a nitrogen-containing group as described above. The carbazole-based compound has high glass transition temperature and/or high melting point, and is stable during electron injection. Thus, when interposed between a pair of electrodes (anode and cathode) of an organic light-emitting diode, the carbazole-based compound may have excellent thermal resistance against Joule's heat generated in organic layers between the pair of electrodes, between the organic layers, or between the organic layer and the electrode during an operation of the organic light-emitting diode. For example, when interposed between an emission layer (EML) and an anode, the carbazole-based compound does not substantially deteriorate by electrons transmitted thereto through the EML. When interposed between the EML and a cathode, the carbazole-based compound does not substantially deteriorate by holes transmitted thereto through the EML.

In addition, since the carbazole-based compound represented by Formula 1 essentially includes a fluorene ring, a film including the carbazole-based compound has high degree of planarization. Thus, an organic light-emitting diode including the carbazole-based compound has excellent electrical characteristics.

Furthermore, at least one of $R_1$ to $R_5$ of the carbazole-based compound represented by Formula 1 is a nitrogen-containing group as described above. Since mobility of holes may be efficiently controlled by the nitrogen-containing group, the balance of charges (electrons and holes) is increased in an organic light-emitting diode including the carbazole-based compound. Thus, light-emitting efficiency in the EML may be increased. Since holes move relatively faster than electrons, excessive holes may be injected into the EML from the anode compared to electrons. Accordingly, exciton-forming regions in the EML are distributed close to the cathode, or the organic layers such as the EML deteriorate by the excessively injected holes, resulting in reducing lifetime of the organic light-emitting diode. However, since at least one of $R_1$ to $R_5$ of the carbazole-based compound represented by Formula 1 is a nitrogen-containing group, the mobility of holes is controlled, for example, the mobility of holes is relatively reduced, and the balance of holes and electrons arrived at the EML may be increased. Thus, the lifetime of the organic light-emitting diode may be increased.

In addition, since at least one of $R_1$ to $R_5$ of the carbazole-based compound represented by Formula 1 is a nitrogen-containing group, electrons diffused from the EML are stabilized. Thus, the lifetime of the organic light-emitting diode may be increased.

Meanwhile, the nitrogen-containing group contained in at least one of $R_1$ to $R_5$ of the carbazole-based compound represented by Formula 1 is not directly bound to the nitrogen positioned at the center of Formula 1, but bound to the central nitrogen via a fluorene ring of Formula 1 or $Ar_3$. Thus, changes in hole-related characteristics, such as hole mobility, caused when the nitrogen-containing group contained in at least one of $R_1$ to $R_5$ is directly bound to the central nitrogen may be prevented, so that efficiency of the organic light-emitting diode may be increased.

Examples of the unsubstituted $C_1$-$C_{60}$ alkyl group (or $C_1$-$C_{60}$ alkyl group) used herein are a $C_1$-$C_{60}$ linear or branched alkyl group such as methyl, ethyl, propyl, isobutyl, sec-butyl, pentyl, iso-amyl, and hexyl. The substituted $C_1$-$C_{60}$ alkyl group is obtained by substituting at least one hydrogen atom of the unsubstituted $C_1$-$C_{60}$ alkyl group with a deuterium atom, a halogen atom, a hydroxyl group, a nitro group, a cyano group, an amino group, an amidino group, hydrazine, hydrazone, a carboxyl group and a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —$N(Q_{11})(Q_{12})$, or —$Si(Q_{13})(Q_{14})(Q_{15})$, wherein $Q_{11}$ to $Q_{15}$ are each independently selected from the group consisting of a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group.

The unsubstituted $C_1$-$C_{60}$ alkoxy group (or $C_1$-$C_{60}$ alkoxy group) used herein may be represented by —OA, wherein A is an unsubstituted $C_1$-$C_{60}$ alkyl group. Examples of the $C_1$-$C_{60}$ alkoxy group include methoxy, ethoxy, or isopropyloxy, and at least one hydrogen atom of the $C_1$-$C_{60}$ alkoxy group may be substituted with the same substituent groups described above with reference to the $C_1$-$C_{60}$ alkyl group.

The unsubstituted $C_2$-$C_{60}$ alkenyl group (or $C_2$-$C_{60}$ alkenyl group) used herein refers to a hydrocarbon chain having at least one carbon-carbon double bond within or at a terminal of the unsubstituted $C_2$-$C_{60}$ alkyl group. Examples of the $C_2$-$C_{60}$ alkenyl group include ethenyl, propenyl, and butenyl. At least one hydrogen atom in the unsubstituted $C_2$-$C_{60}$ alkenyl group may be substituted with the same substituent groups described above with reference to the $C_1$-$C_{60}$ alkyl group.

The unsubstituted alkynyl group (or $C_2$-$C_{60}$ alkynyl group) used herein refers to a hydrocarbon chain having at least one carbon-carbon triple bond within or at a terminal of the $C_2$-$C_{60}$ alkyl group defined above. Examples of the $C_2$-$C_{60}$ alkynyl group include ethynyl and propynyl. At least one hydrogen atom in the unsubstituted $C_2$-$C_{60}$ alkynyl group may be substituted with the same substituent groups described above with reference to the $C_1$-$C_{60}$ alkyl group.

The unsubstituted $C_5$-$C_{60}$ aryl group used herein refers to a monovalent group having a $C_5$-$C_{60}$ carbocyclic aromatic system including at least one aromatic ring. The unsubstituted $C_5$-$C_{60}$ arylene group used herein refers to a divalent group having a $C_5$-$C_{60}$ carbocyclic aromatic system including at least one aromatic ring. If the aryl group and arylene group include at least two rings, they may be fused to each other. At least one hydrogen atom in the aryl group and arylene group may be substituted with the same substituent groups described above with reference to the $C_1$-$C_{60}$ alkyl group.

Examples of the substituted or unsubstituted $C_5$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted or unsubstituted $C_5$-$C_{60}$ arylene group may be easily derived from examples of the substituted or unsubstituted $C_5$-$C_{60}$ aryl group.

The unsubstituted $C_2$-$C_{60}$ heteroaryl group is a monovalent group having at least one aromatic ring having at least one of the heteroatoms selected from the group consisting of N, O, P, and S. The unsubstituted $C_2$-$C_{60}$ heteroarylene group is a divalent group having at least one aromatic ring having at least one of the heteroatoms selected from the group consisting of N, O, P, and S. In this regard, when the heteroaryl group and the heteroarylene group have at least two rings, they may be fused to each other. At least one hydrogen atom in the heteroaryl group and the heteroarylene group may be substituted with the same substituent groups described above with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily derived from examples of the substituted or unsubstituted $C_2$-$C_{60}$ arylene group.

The substituted or unsubstituted $C_5$-$C_{60}$ aryloxy group is —$OA_2$, wherein $A_2$ is a substituted or unsubstituted $C_5$-$C_{60}$ aryl group. The substituted or unsubstituted $C_5$-$C_{60}$ arylthio group is —$OA_3$, wherein $A_3$ is a substituted or unsubstituted $C_5$-$C_{60}$ aryl group.

The carbazole-based compound of Formula 1 may be synthesized using a known organic synthesis method. The method of synthesizing the carbazole-based compound will be clear to one of ordinary skill in the art with reference to the examples that follow.

The carbazole-based compound of Formula 1 may be interposed between a pair of electrodes of an organic light-emitting diode. For example, the carbazole-based compound may be used in an EML, between the EML and an anode, and/or between the EML and a cathode. For example, the carbazole-based compound may be used in a hole injection layer (HIL), a hole transport layer (HTL), or a functional layer having both hole injecting and hole transporting capabilities.

Accordingly, an organic light-emitting diode according to an embodiment of the present invention includes a first electrode, a second electrode disposed opposite to the first electrode, and an organic layer interposed between the first electrode and the second electrode, wherein the organic layer includes the carbazole-based compound represented by Formula 1.

The carbazole-based compound may be contained in the organic layer as a single material or a mixture of different materials. For example, the organic light-emitting diode may include Compound 2 alone or a mixture of Compounds 2 and 8 as the carbazole-based compounds. For example, if the organic light-emitting diode includes both of Compounds 2 and 8, Compounds 2 and 8 may be contained in the same layer, e.g., the HTL. Alternatively, Compounds 2 and 8 may be contained in different layers, e.g., Compound 2 is contained in the HTL and Compound 8 is contained in an electron transport layer (ETL). The expression "the organic layer includes the carbazole-based compound as a single material or a mixture of different materials" used herein will be obvious with reference to the descriptions above.

The organic layer may include at least one layer selected from the group consisting of a HIL, a HTL, a functional layer having both hole injecting and hole transporting capabilities (hereinafter, referred to as "H-functional layer"), a buffer layer, an electron blocking layer (EBL), an EML, a hole blocking layer (HBL), an ETL, an electron injection layer (EIL), and a functional layer having both electron injecting and electron transporting capabilities (hereinafter, referred to as "E-functional layer").

The term "organic layer" used herein refers to a single layer and/or a plurality of layers interposed between the first electrode and the second electrode of the organic light-emitting diode.

The organic layer may include at least one of the HIL, the HTL, and the H-functional layer, and the EML. The at least one of the HIL, the HTL, and the H-functional layer may include the carbazole-based compound. For example, the organic layer may include a HTL or H-functional layer including the carbazole-based compound.

At least one of the HIL, the HTL, and the H-functional layer may further include a bipolar compound that has higher hole mobility and higher conductivity than the carbazole-based compound in addition to the carbazole-based compound. By adding the bipolar compound, hole injecting characteristics are improved, so that driving voltage of the organic light-emitting diode may be reduced. In this regard, since both of the bipolar compound and the carbazole-based compound represented by Formula 1 are used, hole mobility may be controlled, charges are balanced, and/or electrons are stabilized by the carbazole-based compound of Formula 1 in spite of a large amount of holes injected by the bipolar compound. Thus, efficiency and lifetime of the organic light-emitting diode may be improved, driving voltage may be reduced, and efficiency and lifetime may be increased by simultaneously using the bipolar compound and the carbazole-based compound of Formula 1, for example, between the anode and the EML.

The bipolar compound may be represented by Formula 300 below.

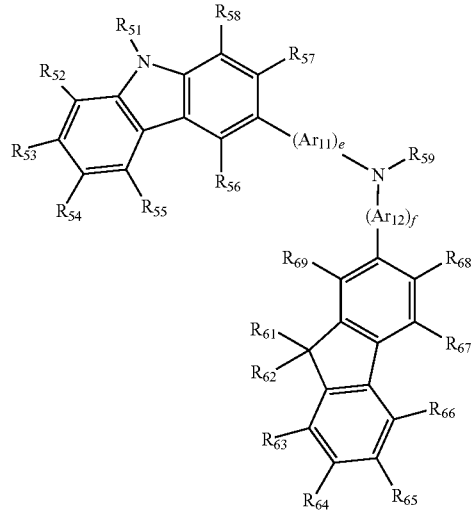

Formula 300

In Formula 300, $Ar_{11}$ and $Ar_{12}$ are each independently a substituted or unsubstituted $C_5$-$C_{60}$ arylene group. $Ar_{11}$ and $Ar_{12}$ are defined as described above with reference to $Ar_1$.

In Formula 300, e and f are each independently an integer from 0 to 5. The e and f are defined as described above with reference to "a".

In Formula 300, $R_{51}$ to $R_{58}$ and $R_{61}$ to $R_{69}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. $R_{51}$ to $R_{58}$ and $R_{61}$ to $R_{69}$ are defined as described above with reference to $R_{11}$.

In Formula 300, $R_{59}$ may be a phenyl group; a naphthyl group; an anthryl group; a biphenyl group; a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment of the present invention, the bipolar compound may be represented by Formula 300A below, but is not limited thereto.

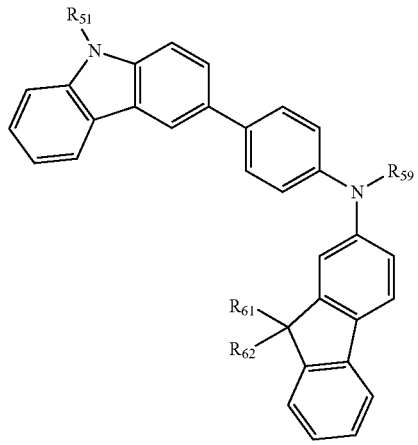

Formula 300A

In Formula 300A, $R_{51}$, $R_{62}$, $R_{61}$, and $R_{59}$ are defined as described above.

For example, the bipolar compound may be Compound 300 below, but is not limited thereto.

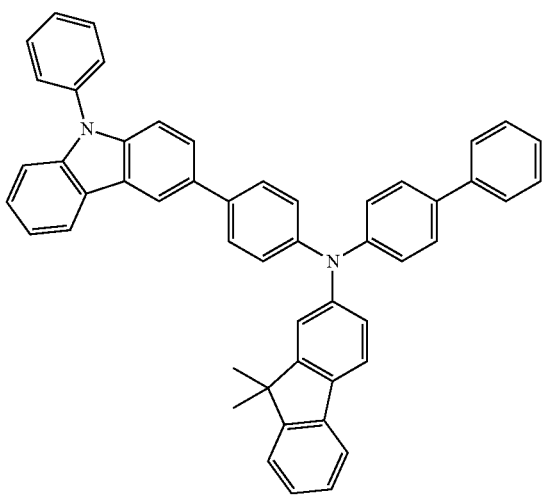

Compound 300

At least one of the HIL, the HTL, and the H-functional layer may further include a charge-generating material in addition to the carbazole-based compound represented by Formula 1 (and, optionally, the bipolar compound), known hole injecting materials, known hole transporting materials, and/or materials having both hole injecting and hole transporting capabilities in order to improve conductivity.

The charge-generating material may be a p-dopant. Examples of the p-dopant include a quinine derivative such as tetracyanoquinonedimethane (TCNQ) and 2,3,5,6-tetrafluorotetracyano-1,4-benzoquinonedimethane (F4TCNQ); a metal oxide such as tungsten oxide and molybdenum oxide; and a cyano group-containing compound such as Compound 200 below, but are not limited thereto.

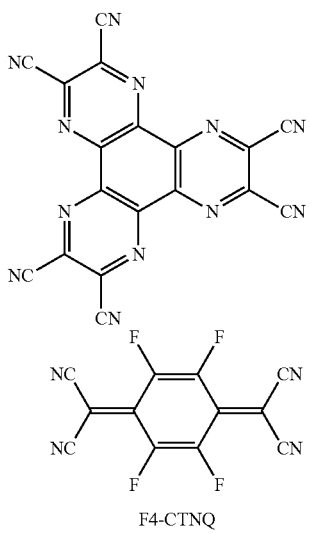

Compound 200

F4-CTNQ

If the HIL, the HTL, or the H-functional layer further includes the charge-generating to material, the charge-generating material may be homogeneously or non-homogeneously dispersed in the HIL, the HTL, or the H-functional layer, or a variety of modifications may be possible.

A buffer layer may be interposed between the EML and at least one of the HIL, the HTL, and the H-functional layer. The buffer layer may increase efficiency by compensating an optical resonance length according to a wavelength of light emitted from the EML. The buffer layer may include known hole injecting materials and known hole transporting materials. The buffer layer may also include a material that is the same as one of the materials contained in the HIL, the HTL, and the H-functional layer disposed under the buffer layer.

The thickness of the buffer layer may be in the range of 10 Å to 700 Å, for example, 20 Å to 500 Å, but is not limited thereto. If the thickness of the buffer layer is within the range described above, an optical resonance length according to the wavelength of the light emitted from the EML is efficiently compensated, thereby increasing efficiency of the organic light-emitting diode.

If the HTL is disposed between the first electrode (for example, anode) and the second electrode (for example, cathode) of the organic light-emitting diode, the HTL may have a single-layered or multi-layered structure.

For example, the HTL may be a single layer including the carbazole-based compound represented by Formula 1, or a single layer including the carbazole-based compound of Formula 1 and the bipolar compound represented by Formula 300. For example, the organic light-emitting diode may have the following structures 1) to 4) between the first electrode and the EML, but is not limited thereto:

1) first electrode/HIL/HTL(carbazole-based compound of Formula 1)/EML;
2) first electrode/HIL/HTL(carbazole-based compound of Formula 1+bipolar compound of Formula 300)/EML;
3) first electrode/HIL/HTL(carbazole-based compound of Formula 1+bipolar compound of Formula 300)/buffer layer(carbazole-based compound of Formula 1)/EML; and
4) first electrode/HIL/HTL(carbazole-based compound of Formula 1+bipolar compound of Formula 300)/buffer layer(bipolar compound of Formula 300)/EML.

In the structures 1) to 4), the HTL may further include the charge-generating material as described above.

In addition, if the HTL has a multi-layered structure, the HTL may include a first HTL and a second HTL which are sequentially stacked from the first electrode. The first HTL and the second HTL may include at least one of the carbazole-based compound of Formula 1 and the bipolar compound of Formula 300. For example, the organic light-emitting diode may have the following structures 5) to 16) between the first electrode and the EML, but is not limited thereto:

5) first electrode/HIL/first HTL(bipolar compound of Formula 300)/second HTL(carbazole-based compound of Formula 1)/EML;
6) first electrode/HIL/first HTL(carbazole-based compound of Formula 1)/second HTL(bipolar compound of Formula 300)/EML;
7) first electrode/HIL/first HTL(bipolar compound of Formula 300)/second HTL(carbazole-based compound of Formula 1+bipolar compound of Formula 300)/EML;
8) first electrode/HIL/first HTL(carbazole-based compound of Formula 1)/second HTL(carbazole-based compound of Formula 1+bipolar compound of Formula 300)/EML;
9) first electrode/HIL/first HTL(carbazole-based compound of Formula 1+bipolar compound of Formula 300)/second HTL(carbazole-based compound of Formula 1)/EML;
10) first electrode/HIL/first HTL(carbazole-based compound of Formula 1+bipolar compound of Formula 300)/second HTL(bipolar compound of Formula 300)/EML;
11) first electrode/HIL/first HTL(bipolar compound of Formula 300)/second HTL(carbazole-based compound of Formula 1)/buffer layer(bipolar compound of Formula 300)/EML;
12) first electrode/HIL/first HTL(carbazole-based compound of Formula 1)/second HTL(bipolar compound of Formula 300)/buffer layer(carbazole-based compound of Formula 1)/EML;
13) first electrode/HIL/first HTL(bipolar compound of Formula 300)/second HTL(carbazole-based compound of Formula 1+bipolar compound of Formula 300)/buffer layer(carbazole-based compound of Formula 1)/EML;
14) first electrode/HIL/first HTL(bipolar compound of Formula 300)/second HTL(carbazole-based compound of Formula 1+bipolar compound of Formula 300)/buffer layer(bipolar compound of Formula 300)/EML;
15) first electrode/HIL/first HTL(carbazole-based compound of Formula 1)/second HTL(carbazole-based compound of Formula 1+bipolar compound of Formula 300)/buffer layer(carbazole-based compound of Formula 1)/EML; and
16) first electrode/HIL/first HTL(carbazole-based compound of Formula 1)/second HTL(carbazole-based compound of Formula 1+bipolar compound of Formula 300)/buffer layer(bipolar compound of Formula 300)/EML.

In the structures 5) to 16), at least one of the first HTL and the second HTL may further include the charge-generating material as described above.

The thickness ratio between the first HTL and the second HTL may be in the range of 1:9 to 9:1, for example, 3:7 to 7:3. For example, the thickness ratio between the first HTL and the second HTL may be about 5:5.

If the H-functional layer is interposed between the first electrode and the second electrode of the organic light-emitting diode, the H-functional layer may have a single-layered or multi-layered structure.

For example, the H-functional layer may be a single layer including the carbazole-based compound represented by Formula 1, or a single layer including the carbazole-based compound of Formula 1 and the bipolar compound represented by Formula 300. For example, the organic light-emitting diode may have the following structures 17) to 20) between the first electrode and the EML, but is not limited thereto:

17) first electrode/H-functional layer(carbazole-based compound of Formula 1)/EML;
18) first electrode/H-functional layer(carbazole-based compound of Formula 1+bipolar compound of Formula 300)/EML;
19) first electrode/H-functional layer(carbazole-based compound of Formula 1+bipolar compound of Formula 300)/buffer layer(carbazole-based compound of Formula 1)/EML; and
20) first electrode/H-functional layer(carbazole-based compound of Formula 1+bipolar compound of Formula 300)/buffer layer(bipolar compound of Formula 300)/EML.

In the structures 17) to 20), the H-functional layer may further include the charge-generating material as described above.

In addition, if the H-functional layer has a multi-layered structure, the H-functional layer may include a first H-functional layer and a second H-functional layer which are sequentially stacked from the first electrode. The first H-functional layer and the second H-functional layer may include at least one of the carbazole-based compound of Formula 1 and the bipolar compound of Formula 300. For example, the organic light-emitting diode may have the following structures 21) to 32) between the first electrode and the EML, but is not limited thereto:

21) first electrode/first H-functional layer(bipolar compound of Formula 300)/second H-functional layer(carbazole-based compound of Formula 1)/EML;
22) first electrode/first H-functional layer(carbazole-based compound of Formula 1)/second H-functional layer(bipolar compound of Formula 300)/EML;
23) first electrode/first H-functional layer(bipolar compound of Formula 300)/second H-functional layer(carbazole-based compound of Formula 1+bipolar compound of Formula 300)/EML;
24) first electrode/first H-functional layer(carbazole-based compound of Formula 1)/second H-functional layer (carbazole-based compound of Formula 1+bipolar compound of Formula 300)/EML;
25) first electrode/first H-functional layer(carbazole-based compound of Formula 1+bipolar compound of Formula 300)/second H-functional layer(carbazole-based compound of Formula 1)/EML;
26) first electrode/first H-functional layer(carbazole-based compound of Formula 1+bipolar compound of Formula 300)/second H-functional layer(bipolar compound of Formula 300)/EML;
27) first electrode/first H-functional layer(bipolar compound of Formula 300)/second H-functional layer(carbazole-based compound of Formula 1)/buffer layer(bipolar compound of Formula 300)/EML;
28) first electrode/first H-functional layer(carbazole-based compound of Formula 1)/second H-functional layer(bipolar compound of Formula 300)/buffer layer(carbazole-based compound of Formula 1)/EML;
29) first electrode/first H-functional layer(bipolar compound of Formula 300)/second H-functional layer(carbazole-based compound of Formula 1+bipolar compound of Formula 300)/buffer layer(carbazole-based compound of Formula 1)/EML;
30) first electrode/first H-functional layer(bipolar compound of Formula 300)/second H-functional layer(carbazole-based compound of Formula 1+bipolar compound of Formula 300)/buffer layer(bipolar compound of Formula 300)/EML;
31) first electrode/first H-functional layer(carbazole-based compound of Formula 1)/second H-functional layer (carbazole-based compound of Formula 1+bipolar compound of Formula 300)/buffer layer(carbazole-based compound of Formula 1)/EML; and
32) first electrode/first H-functional layer(carbazole-based compound of Formula 1)/second H-functional layer (carbazole-based compound of Formula 1+bipolar compound of Formula 300)/buffer layer(bipolar compound of Formula 300)/EML.

In the structures 21) to 32), at least one of the first H-functional layer and the second H-functional layer may further include the charge-generating material as described above.

The thickness ratio between the first H-functional layer and the second H-functional layer may be in the range of 1:9 to 9:1, for example, 3:7 to 7:3. For example, the thickness ratio between the first H-functional layer and the second H-functional layer may be about 5:5.

The EML may further include a phosphorescent dopant, and the carbazole-based compound contained in the EML may function as a phosphorescent host. The phosphorescent dopant may be an organic metal complex including Ir, Pt, Os, Re, Ti, Zr, Hf, or any combination of at least two thereof, but is not limited thereto.

The EML may be a red, green, or blue EML. For example, the EML may be a blue EML. The carbazole-based compound may be used with a blue EML including a phosphorescent dopant, resulting in providing an organic light-emitting diode emitting blue light and having high efficiency, high brightness, high color purity, and long lifetime.

In addition, the organic layer may include an ETL that include the carbazole-based compound. In this regard, the ETL may further include a metal-containing compound in addition to the carbazole-based compound.

Alternatively, the organic layer may include an ETL that includes known electron transporting organic compounds and metal-containing compounds.

The metal-containing compound may include a Li complex. Examples of the Li complex include lithium quinolate (LiQ) or Compound 203 below, but are not limited thereto.

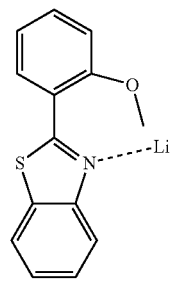

Compound 203

FIG. 1 is a schematic sectional view of an organic light-emitting diode 10 according to an embodiment of the present invention. Hereinafter, the organic light-emitting diode 10 and a method of fabricating the organic light-emitting diode 10 will be described with reference to FIG. 1.

The substrate 11, which may be any substrate that is commonly used in organic light emitting devices, may be a glass substrate or a transparent plastic substrate with excellent mechanical strength, thermal stability, transparency, surface smoothness, ease of handling, and waterproofness.

The first electrode 13 may be formed on the substrate 11 by depositing or sputtering a to material that is used to form the first electrode 13. When the first electrode 13 constitutes an anode, the material used to form the first electrode 13 may be a high work-function material so as to facilitate hole injection. The first electrode 13 may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layered or a multi-layered structure. For example, the first electrode 13 may have a triple-layer structure of ITO/Ag/ITO, but is not limited thereto.

The organic layer 15 may be disposed on the first electrode 13.

The organic layer 15 may include a HIL, a HTL, a buffer layer, an EML, an ETL, and an EEL.

The HIL may be formed on the first electrode 13 by vacuum deposition, spin coating, casting, Langmuir-Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec, but are not limited thereto.

When the HIL is formed using spin coating, coating conditions may vary according to a compound that is used to form the HIL, and the structure and thermal properties of the HTL to be formed. For example, the coating conditions may include a coating speed of about 2000 rpm to about 5000 rpm, and a thermal treatment temperature of about 80° C. to about 200° C., wherein the thermal treatment is for removing a solvent after coating. However, the coating conditions are not limited thereto.

The HIL may be formed of any material that is commonly used to form a HIL. Examples of known hole injecting materials include, but are not limited to, N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS).

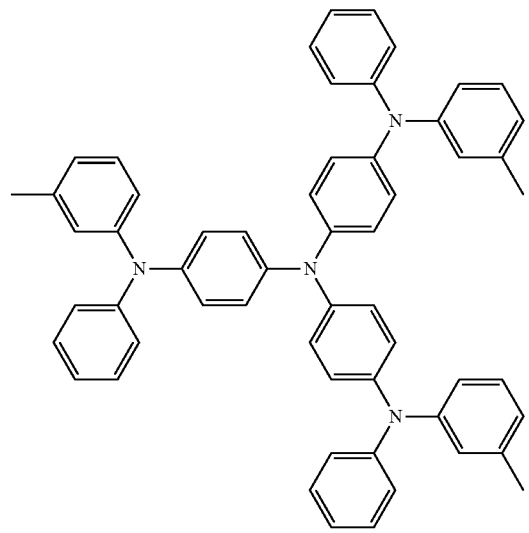

m-MTDATA

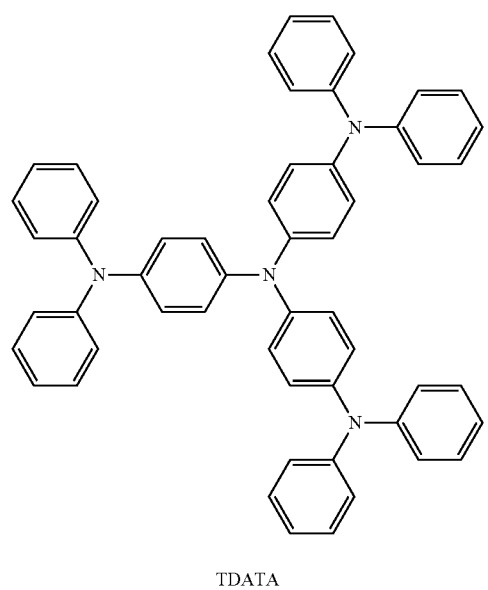

TDATA

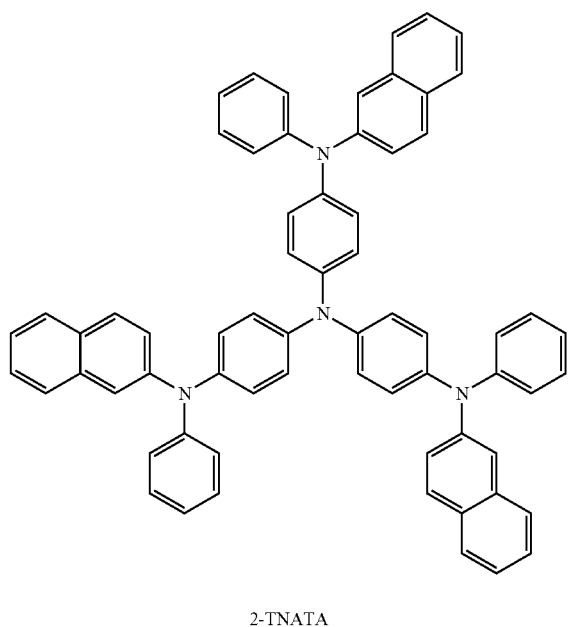 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

The thickness of the HIL may be about 100 to about 10,000 Å, and for example, about 100 to about 1,000 Å. When the thickness of the HIL is within this range, the HIL may have excellent hole injecting ability without a substantial increase in driving voltage Then, the HTL may be formed on the HIL by using vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used to form the HTL.

The hole transporting materials may include at least one of the carbazole-based compound of Formula 1, the bipolar compound, or known hole transporting materials. Examples of the known hole transporting material include a carbazole derivative such as N-phenylcarbazole and polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB), but are not limited thereto.

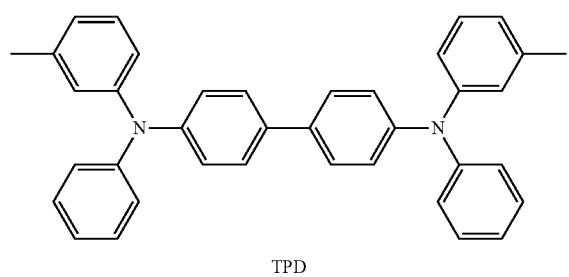

TPD

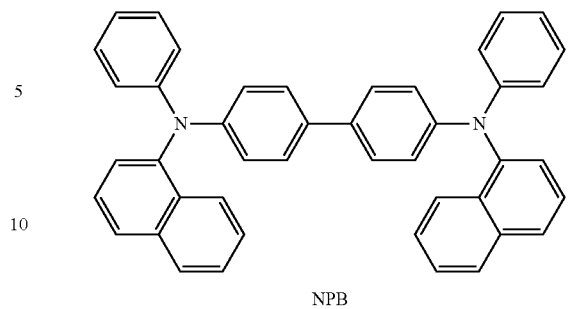

NPB

The thickness of the HTL may be in a range of about 50 to about 2000 Å, for example, about 100 to about 1500 Å. When the thickness of the HTL is within this range, the HTL may have excellent hole transporting ability without a substantial increase in driving voltage The buffer layer may be formed on the HTL by vacuum deposition, spin coating, casting, LB deposition, or the like. When the buffer layer is formed by vacuum deposition or spin coating, the conditions for deposition and coating may be similar to those for the formation of the HIL, although the conditions for the deposition and coating may vary according to the material that is used to form the buffer layer.

The buffer layer is defined as described above.

Then, the EML may be formed on the buffer layer by vacuum deposition, spin coating, casting, LB deposition, or the like. When the EML is formed by using vacuum deposition or spin coating, the deposition and coating conditions may be similar to those used to form the HIL, although the deposition and coating conditions may vary according to a compound that is used to form the EML.

The material for forming the EML may include at least one of known emitting materials (host and/or dopant).

Examples of known host include tris(8-quinolinolate)aluminum (Alq3), 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

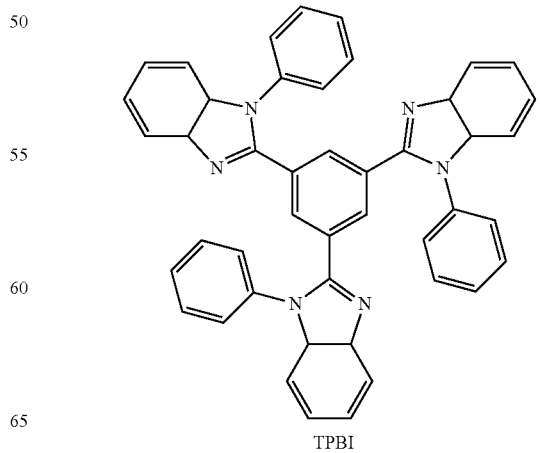

TPBI

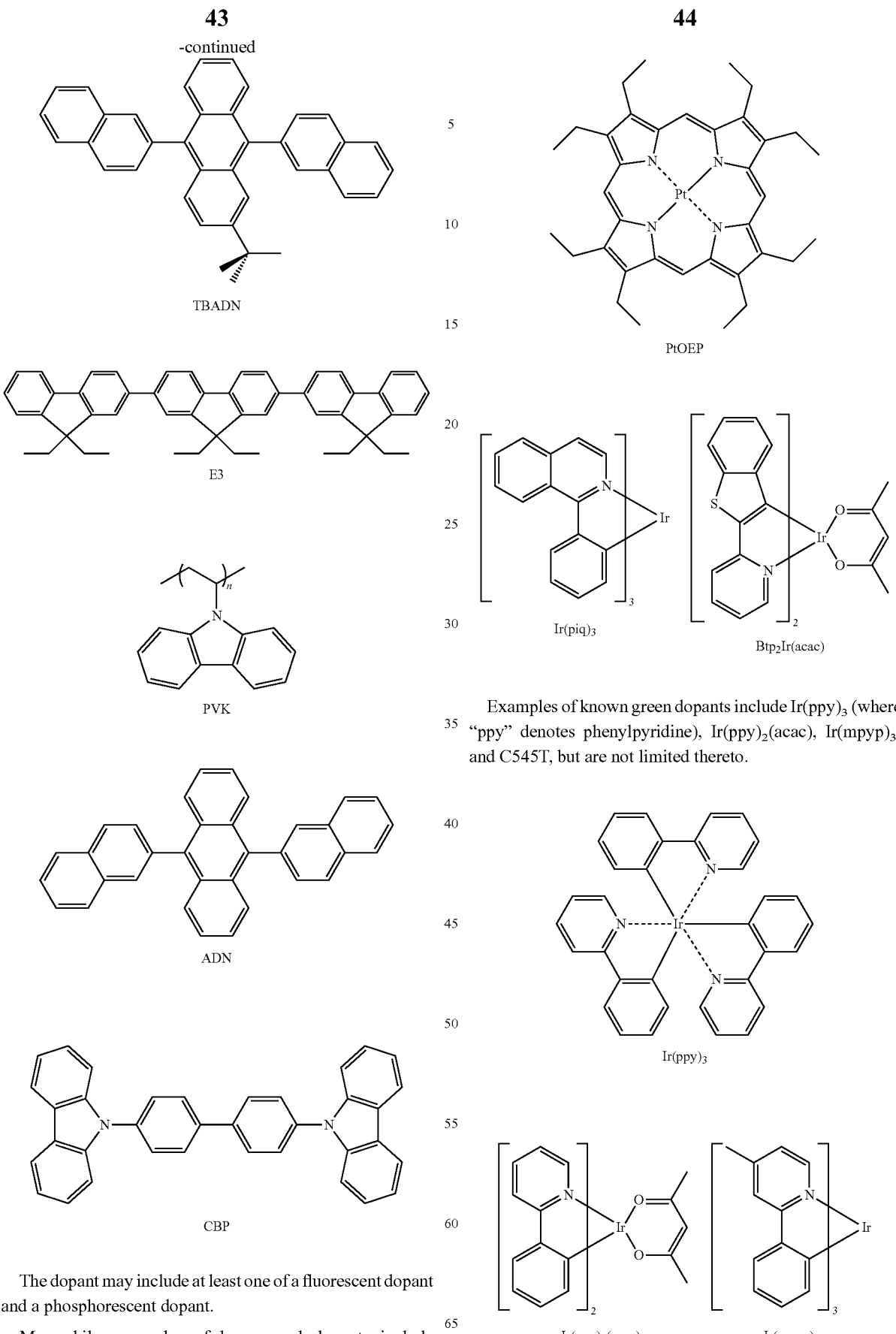
The dopant may include at least one of a fluorescent dopant and a phosphorescent dopant.
Meanwhile, examples of known red dopants include PtOEP, Ir(piq)$_3$, and Btp$_2$Ir(acac), but are not limited thereto.
Examples of known green dopants include Ir(ppy)$_3$ (where "ppy" denotes phenylpyridine), Ir(ppy)$_2$(acac), Ir(mpyp)$_3$, and C545T, but are not limited thereto.

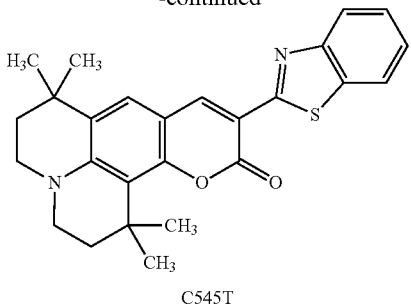

C545T

Examples of known blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), but are not limited thereto.

If the EML includes a host and a dopant, the amount of the dopant may be in the range of about 0.01 to about 15 parts by weight based on 100 parts by weight of the host, but is not limited thereto.

The thickness of the EML may be in the range of about 100 Å to about 1,000 Å, for example, about 200 Å to about 600 Å. When the thickness of the EML is within this range, the EML may have excellent light emitting ability without a substantial increase in driving voltage.

Then, the ETL may be formed on the EML by vacuum deposition, spin coating, casting, or the like. When the ETL is formed using vacuum deposition or spin coating, the deposition and coating conditions may be similar to those for formation of the HIL, although the deposition and coating conditions may vary according to a compound that is used to form the ETL. Electron transporting materials may include a material that can stably transport electrons injected from the electron injecting electrode (cathode) and the carbazole-based compound of Formula 1 may be used. Examples of known

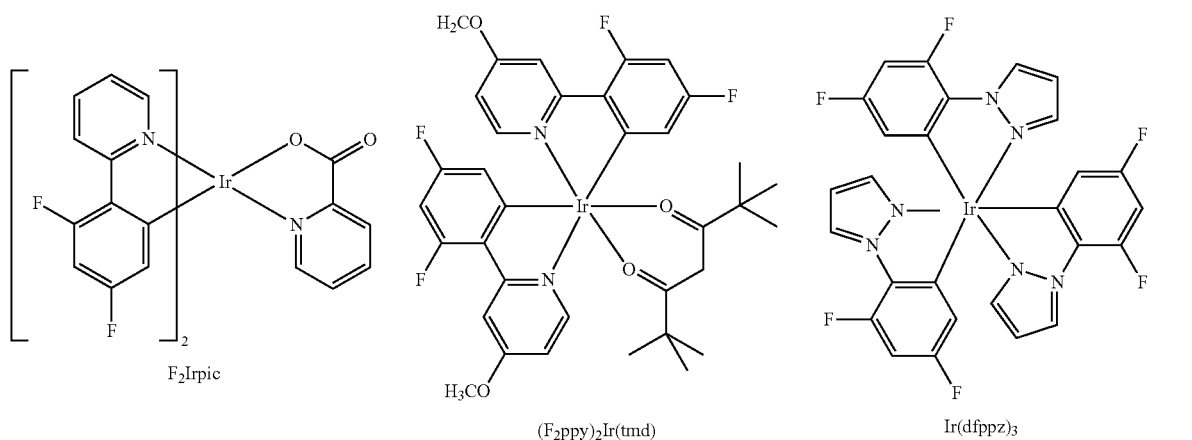

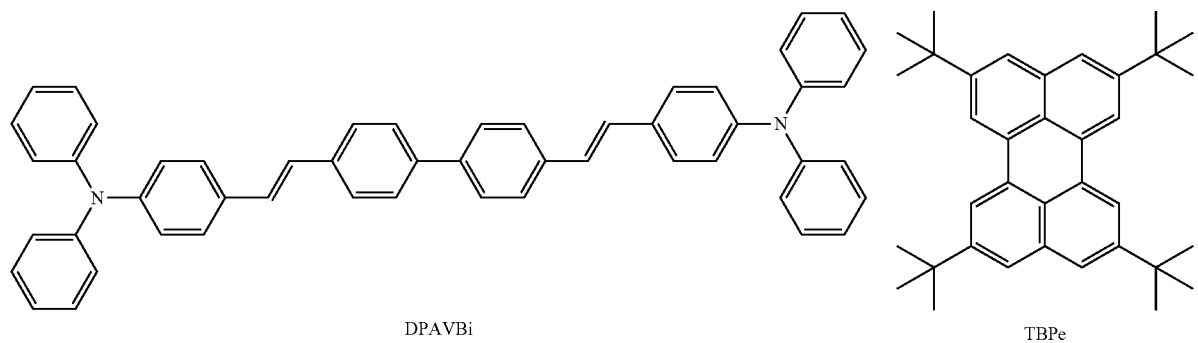

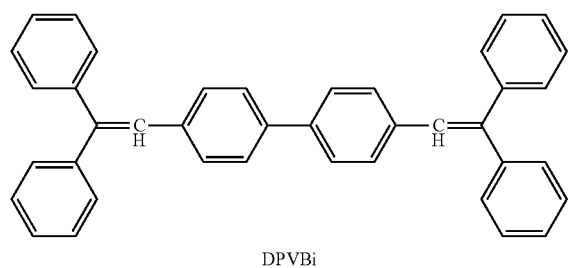

DPVBi electron transporting materials include quinoline derivatives, such as Alq3, TAZ, Balq1, beryllium bis(benzoquinolin-10-olate) (Balq$_2$), ADN, Compound 201, and Compound 202, but are not limited thereto.

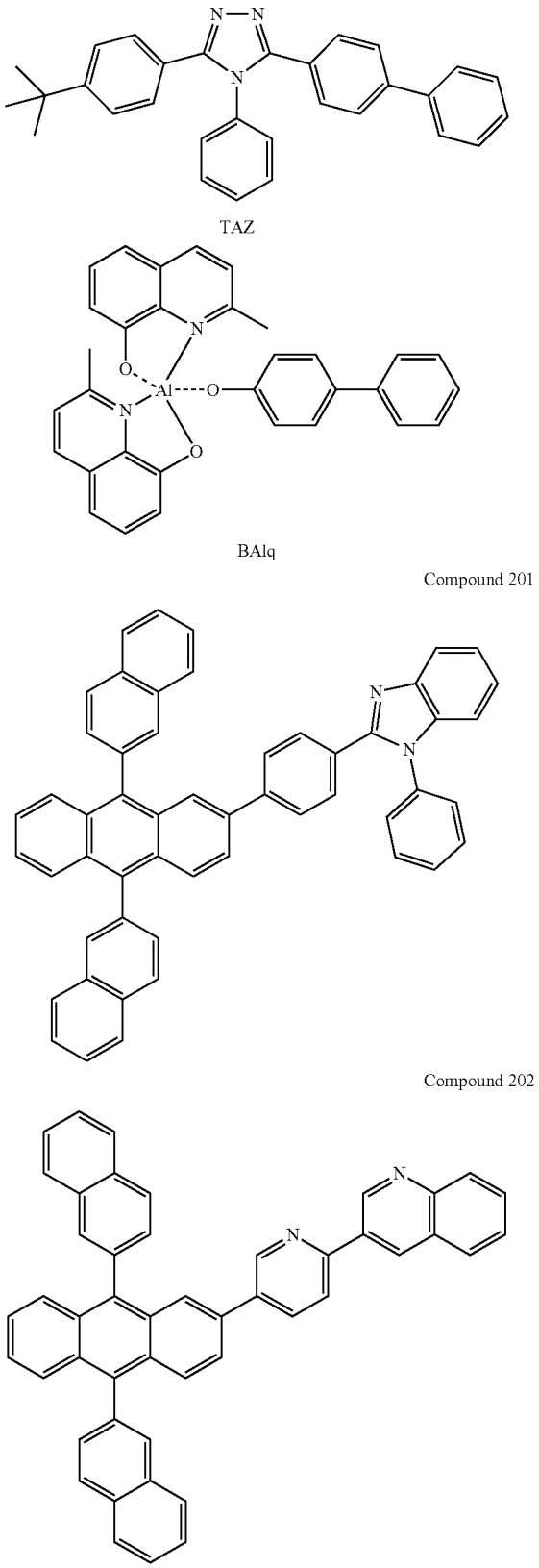

The thickness of the ETL may be in the range of about 100 Å to about 1,000 Å, for example, about 150 Å to about 500 Å. When the thickness of the ETL is within the range described above, the ETL may have excellent electron transporting ability without a substantial increase in driving voltage.

Alternatively, the ETL may further include a metal-containing material in addition to known electron transporting organic compounds or the carbazole-based compound of Formula 1.

In addition, the EIL may be formed on the ETL using any material that allows electrons to be easily injected from the cathode.

Examples of electron injecting materials include LiF, NaCl, CsF, Li$_2$O, and BaO, which are known in the art. The conditions for deposition of the EIL are similar to those for formation of the HIL, although the deposition conditions may vary according to a material that is used to form the EIL.

The thickness of the EIL may be in the range of about 1 to about 100 Å, for example, in the range of about 3 to about 90 Å. When the thickness of the EIL is within this range, the EIL may have excellent electron injecting ability without a substantial increase in driving voltage.

The second electrode 17 is disposed on the organic layer 15. The second electrode 17 may be a cathode, which is an electron-injecting electrode. A metal for forming the second electrode 17 may be a metal, an alloy, or an electrically conductive compound, which have a low-work function, or a mixture thereof. In this regard, the second electrode 17 may be a transmissive electrode formed of lithium (Li), magnesium (Mg), aluminum (Al), aluminum (Al)-lithium (Li), calcium (Ca), magnesium (Mg)-indium, (In), magnesium (Mg)-silver (Ag), or the like. Meanwhile, in order to manufacture a top-emission type organic light-emitting diode, a transmissive electrode formed of ITO or IZO may be used.

The organic light-emitting diode is described with reference to FIG. 1, but is not limited thereto.

For example, the organic light-emitting diode may have one of the structures 1) to 32) above between the first electrode 13 and the EML. In this regard, the thickness of the H-functional layer may be in the range of 100 Å to 10000 Å, for example, 500 Å to 5000 Å. If the thickness of the H-functional layer is within the range described above, the organic light-emitting diode may have excellent electrical characteristics without an increase in driving voltage.

When a phosphorescent dopant is also used to form the EML, a HBL may be formed between the HTL and the EML or between the H-functional layer and the EML by using vacuum deposition, spin coating, casting, LB deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any material that is commonly used to form a HBL may be used. Examples of electron blocking materials include an oxadiazole derivative, a triazole derivative, and a phenanthroline derivative. For example, BCP may be used as the hole blocking material.

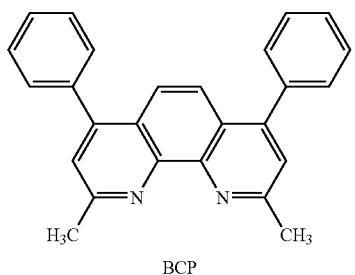
BCP

The thickness of the HBL may be in a range of about 20 to about 1,000 Å, for example, about 30 to about 300 Å. When the thickness of the HBL is within this range, the HBL may have excellent hole blocking ability without a substantial increase in driving voltage.

Hereinafter, one or more embodiments will be described in detail with reference to the following examples. These examples are not intended to limit the purpose and scope of the one or more embodiments of the present invention.

EXAMPLES

Synthesis of Intermediates a to j

Intermediates a to j were synthesized through Reaction Scheme 1 below:

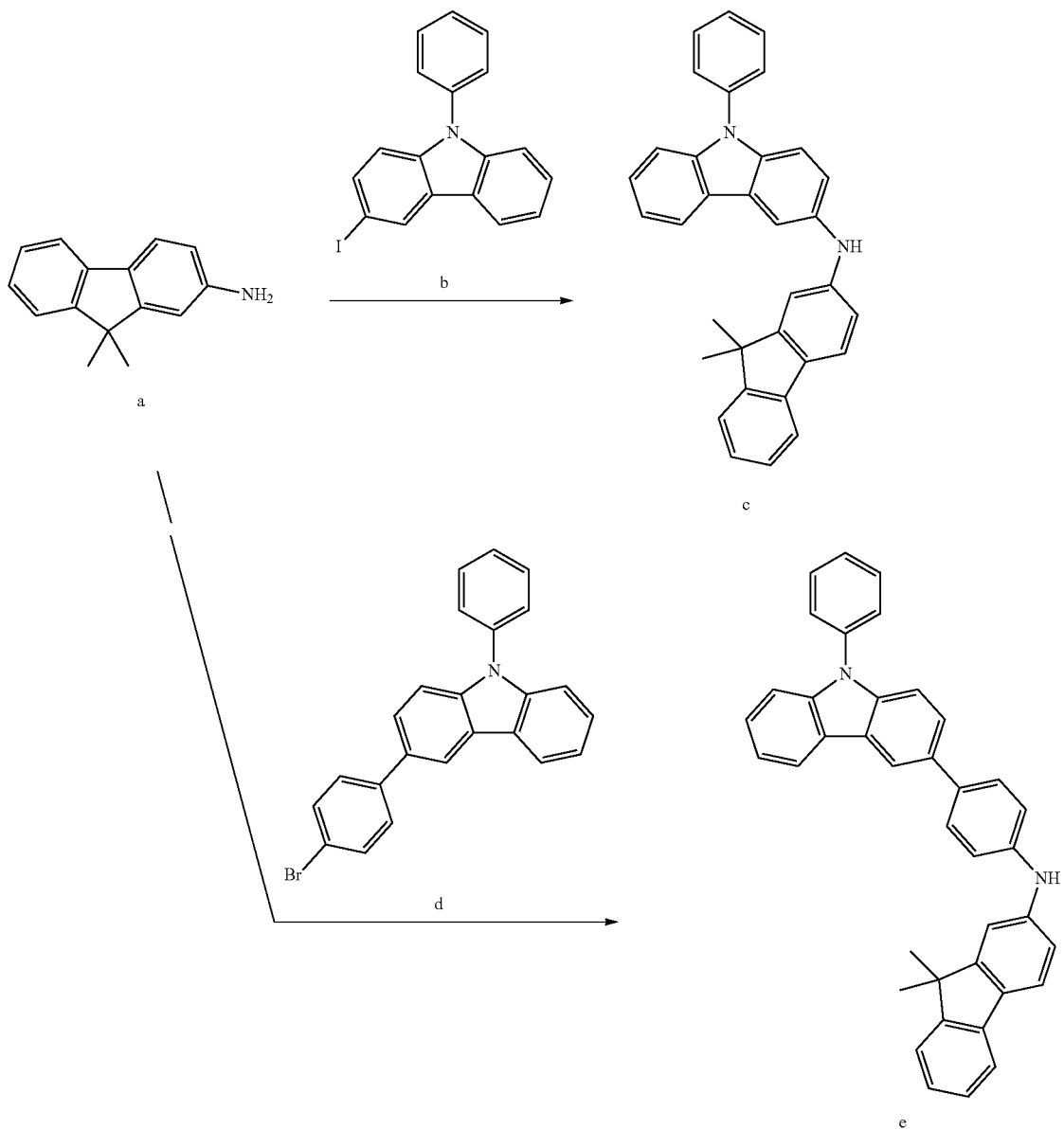

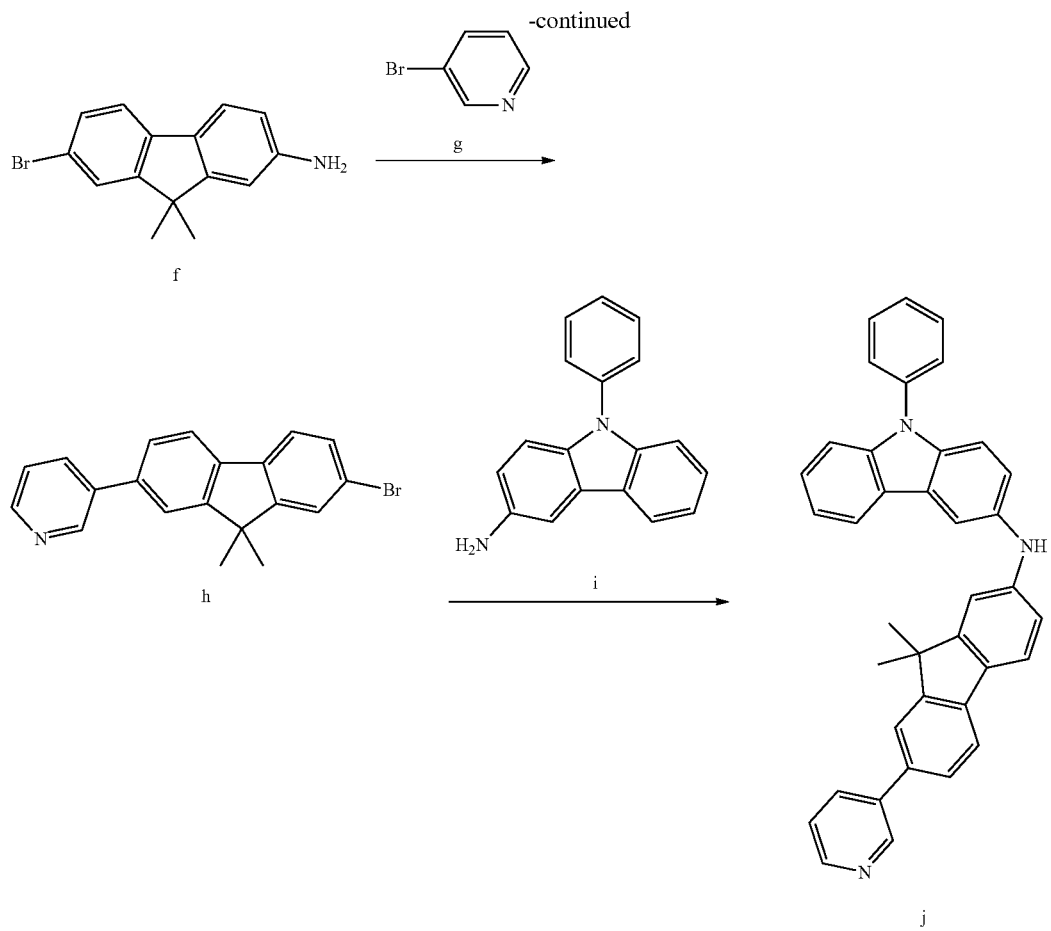

Synthesis of Intermediate c 0.5 g (50 mmol) of Intermediate a, 18.5 g (50 mmol) of Intermediate b, 1.35 g (3.0 mole %) of tris(dibenzylideneacetone)dipalladium(0) ($Pd_2(dba)_3$), 7.2 g (75 mmol) of sodium tert-butoxide, and 300 mg (3.0 mole %) of tri-tert-butylphosphine ($P(t-Bu)_3$) were added to 300 mL of toluene, and the mixture was refluxed while stirring at 100° C. for 5 hours. The reaction mixture was cooled to room temperature and subjected to extraction with methylene chloride and $H_2O$. Then, the resultant was dried using magnesium sulfate to evaporate the solvent. The residue was separately purified using silica gel column chromatography to obtain 18.5 g of Intermediate c (Yield: 82%). The produced compound was identified using LC-MS. $C_{33}H_6N_2$:M+ 450.21

Synthesis of Intermediate e 10.5 g (50 mmol) of Intermediate a, 19.9 g (50 mmol) of Intermediate d, 1.35 g (3.0 mole %) of $Pd_2(dba)_3$, 7.2 g (75 mmol) of sodium tert-butoxide, and 300 mg (3.0 mole %) of $P(t-Bu)_3$ were added to 300 mL of toluene, and the mixture was refluxed while stirring at 100° C. for 5 hours. The reaction mixture was cooled to room temperature and subjected to extraction with methylene chloride and $H_2O$. Then, the resultant was dried using magnesium sulfate to evaporate the solvent. The residue was separately purified using silica gel column chromatography to obtain 22.5 g of Intermediate e (Yield: 85%). The produced compound was identified using LC-MS. $C_{39}H_{30}N_2$:M+ 526.24

Synthesis of Intermediate h 5.8 g (50 mmol) of Intermediate f, 9.5 g (60 mmol) of Intermediate g, 0.5 g (3.0 mole %) of $Pd_2(dba)_3$, 2.9 g (75 mmol) of sodium tert-butoxide, and 120 mg (3.0 mole %) of $P(t-Bu)_3$ were added to 100 mL of toluene, and the mixture was refluxed while stirring at 100° C. for 5 hours. The reaction mixture was cooled to room temperature and subjected to extraction with methylene chloride and $H_2O$. Then, the resultant was dried using magnesium sulfate to evaporate the solvent. The residue was separately purified using silica gel column chromatography to obtain 4.3 g of Intermediate h (Yield: 74%). The produced compound was identified using LC-MS. $C_{20}H_{18}N_2$:M+ 286.15

Synthesis of Intermediate j 4.0 g (14 mmol) of Intermediate h, 3.6 g (14 mmol) of Intermediate 1,380 mg (3.0 mole %) of $Pd_2(dba)_3$, 2.0 g (21 mmol) of sodium tert-butoxide, and 84 mg (3.0 mole %) of $P(t-Bu)_3$ were added to 100 mL of toluene, and the mixture was refluxed while stirring at 100° C. for 5 hours. The reaction mixture was cooled to room temperature and subjected to extraction with methylene chloride and $H_2O$. Then, the resultant was dried using magnesium sulfate to evaporate the solvent. The residue was separately purified using silica gel column chromatography to obtain 6.1 g of Intermediate j (Yield: 83%). The produced compound was identified using LC-MS. $C_{38}H_{29}N_3$:M+ 527.24

Intermediates 1 to 9
1 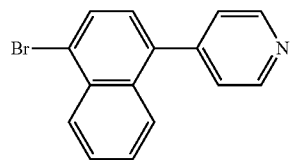
2 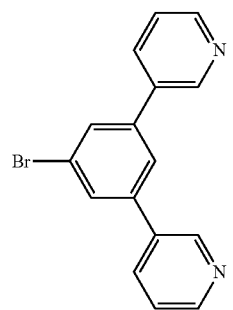
3 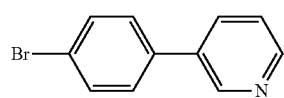
4 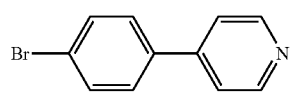
5 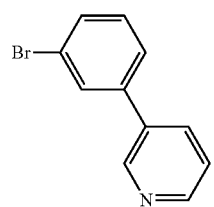
6 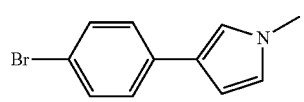
7 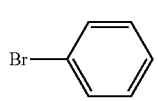
8 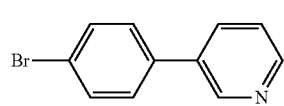
9 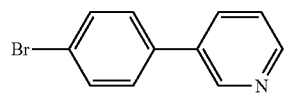
Reaction Scheme for Synthesizing Compounds 2, 3, 8, 14, 15, 16, 20, 31, and 33
c + 1 ⟶
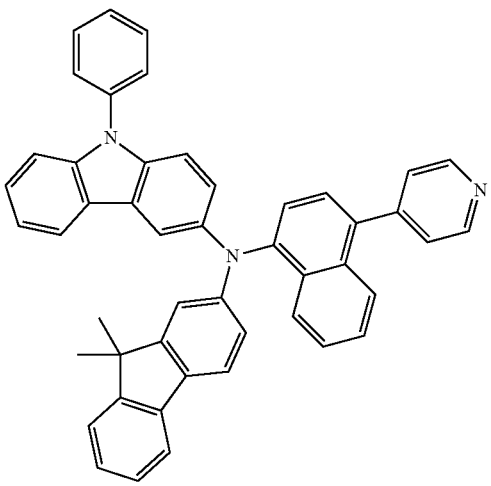
c + 2 ⟶
c + 3 ⟶ e + 4 →
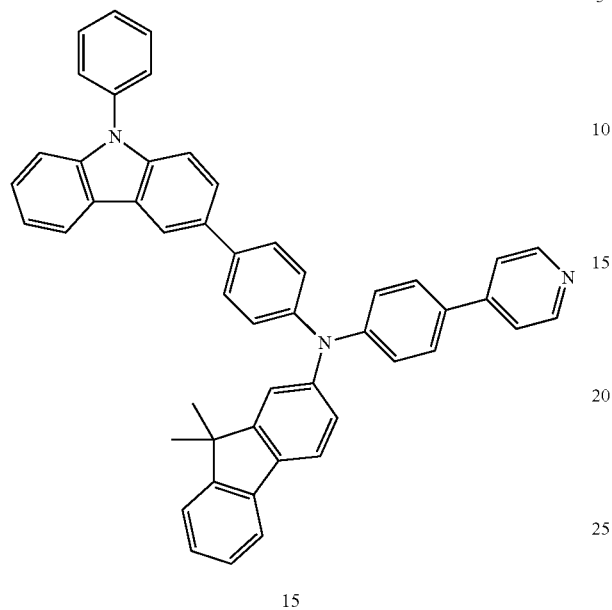
15
e + 5 →
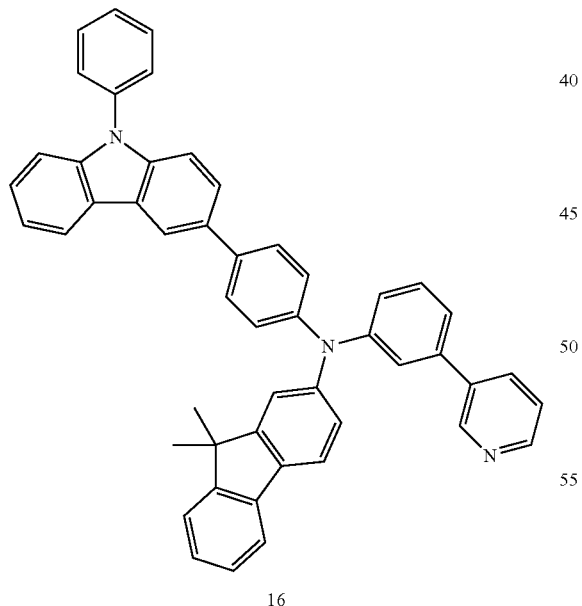
16
j + 7 →
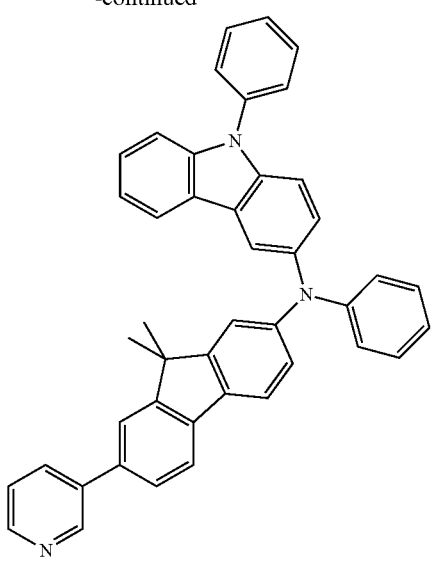
20
e + 6 →
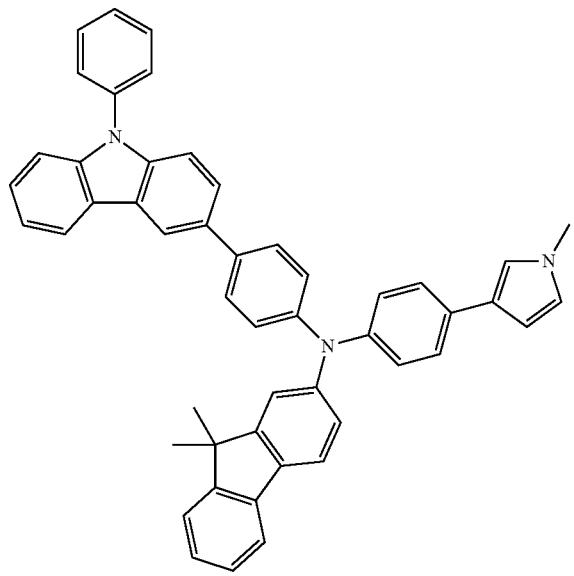
31
e + 8 →

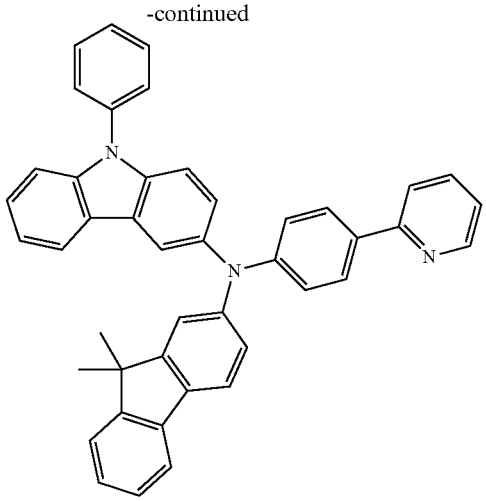

3 e + 9 →

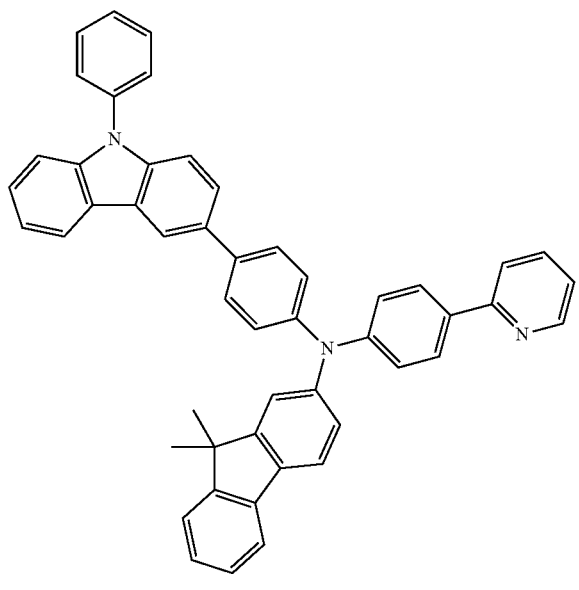

33

Synthesis of Compound 2

4.50 g (10 mmol) of Intermediate c, 2.84 g (10 mmol) of Intermediate 1,270 mg (3.0 mole %) of Pd$_2$(dba)$_3$, 1.4 g (15 mmol) of sodium tert-butoxide, and 60 mg (3.0 mole %) of P(t-Bu)$_3$ were added to 100 mL of toluene, and the mixture was refluxed while stirring at 100° C. for 5 hours. The reaction mixture was cooled to room temperature and subjected to extraction with methylene chloride and H$_2$O. Then, the resultant was dried using magnesium sulfate to evaporate the solvent. The residue was separately purified using silica gel column chromatography to obtain 5.69 g of Compound 2 (Yield: 87%). The produced compound was identified using LC-MS and NMR. C$_{48}$H$_{35}$N$_3$:M+ 653.28

$^1$H NMR (CDCl$_3$, 400 MHz) δ (ppm) 8.70 (m, 2H), 8.22-8.20 (d, 1H), 7.79 (d, 1H), 7.78-7.74 (m, 2H) 7.57-7.23 (m, 16H), 7.14-7.08 (m, 2H), 6.92-6.88 (m, 1H), 6.81-6.79 (m, 1H), 6.66-6.64 (m, 1H), 6.47 (m, 2H), 1.61 (s, 6H)

Synthesis of Compound 8

6.06 g of Compound 8 was synthesized with a yield of 89% in the same manner as in the synthesis of Compound 2, except that 3.1 g (10 mmol) of Intermediate 2 was used instead of Intermediate 1. The produced compound was identified using LC-MS and NMR. C$_{49}$H$_{36}$N$_4$:M+ 680.29

$^1$H NMR (CDCl$_3$, 400 MHz) δ (ppm) 8.89 (m, 2H), 8.67-8.66 (m, 2H), 8.22-8.20 (d, 1H), 7.94-7.90 (m, 3H), 7.78-7.76 (m, 1H), 7.68 (m, 1H), 7.63-7.61 (m, 1H), 7.50-7.46 (m, 6H), 7.40-7.22 (m, 6H), 7.14-7.08 (m, 2H), 7.00 (m, 2H), 6.91-6.89 (m, 1H), 6.74-6.72 (m, 1H) 6.61 (m, 1H), 1.61 (s, 6H)

Synthesis of Compound 14

5.30 g of Compound 14 was synthesized with a yield of 78% in the same manner as in the synthesis of Compound 2, except that 5.27 g (10 mmol) of Intermediate e and 2.3 g (10 mmol) of Intermediate 3 were used instead of Intermediates c and 1. The produced compound was identified using LC-MS and NMR. C$_{50}$H$_{37}$N$_3$:M+ 679.30

$^1$H NMR (CDCl$_3$, 400 MHz) δ (ppm) 8.90 (m, 1H), 8.60-8.58 (m, 1H), 8.24-8.22 (d, 1H), 8.15 (s, 1H), 7.93-7.91 (m, 1H), 7.78-7.84 (m, 2H), 7.67-7.64 (m, 1H), 7.58-7.54 (m, 3H), 7.52-7.46 (m, 5H), 7.38-7.24 (m, 6H), 7.21-7.19 (d, 1H), 7.13-7.10 (m, 2H), 6.71-6.64 (m, 3H), 6.58-6.54 (m, 2H), 6.42 (m, 1H), 1.61 (s, 6H)

Synthesis of Compound 15

5.57 g of Compound 15 was synthesized with a yield of 82% in the same manner as in the synthesis of Compound 2, except that 5.27 g (10 mmol) of Intermediate e and 2.3 g (10 mmol) of Intermediate 4 were used instead of Intermediates c and 1. The produced compound was identified using LC-MS and NMR. C$_{50}$H$_{37}$N$_3$:M+ 679.30

$^1$H NMR (CDCl$_3$, 400 MHz) δ (ppm) 8.72 (m, 2H), 8.24-8.22 (d, 1H), 8.15 (s, 1H), 7.78-7.73 (m, 2H), 7.67-7.64 (m, 1H), 7.58-7.55 (m, 7H), 7.51-7.47 (m, 4H), 7.39-7.27 (m, 4H), 7.21-7.19 (d, 1H), 7.13-7.10 (m, 2H), 6.71-6.66 (m, 3H), 6.58-6.54 (m, 2H), 6.42 (m, 1H), 1.61 (s, 6H)

Synthesis of Compound 16

5.85 g of Compound 16 was synthesized with a yield of 86% in the same manner as in the synthesis of Compound 2, except that 5.27 g (10 mmol) of Intermediate e and 2.3 g (10 mmol) of Intermediate 5 were used instead of Intermediates c and 1. The produced compound was identified using LC-MS and NMR. C$_{50}$H$_{37}$N$_3$:M+ 679.30

$^1$H NMR (CDCl$_3$, 400 MHz) δ (ppm) 8.86 (m, 1H), 8.65-8.64 (m, 1H), 8.24-8.22 (d, 1H), 8.15 (s, 1H), 7.85-7.74 (m, 1H), 7.78-7.73 (m, 2H), 7.67-7.64 (m, 1H), 7.58-7.55 (m, 3H), 7.51-7.47 (m, 4H), 7.43-7.11 (m, 8H), 7.07-7.04 (m, 3H), 6.74-6.70 (m, 1H), 6.58-6.54 (m, 2H), 6.49 (m, 1H), 6.23-6.21 (m, 1H), 1.61 (s, 6H)

Synthesis of Compound 20

4.95 g of Compound 20 was synthesized with a yield of 82% in the same manner as in the synthesis of Compound 2, except that 5.27 g (10 mmol) of Intermediate j and 1.57 g (10 mmol) of Intermediate 7 were used instead of Intermediates c and 1. The produced compound was identified using LC-MS and NMR. $C_{44}H_{33}N_3$:M+ 03.27

$^1$H NMR (CDCl$_3$, 400 MHz) δ (ppm) 8.94 (s, 1H), 8.65-8.64 (m, 1H), 8.22-0.20 (d, 1H), 8.06-8.04 (m, 1H), 7.76-7.72 (m, 3H), 7.57-7.55 (m, 2H), 7.50-7.45 (m, 4H), 7.43-7.23 (m, 6H), 7.09-7.05 (m, 2H), 6.87-6.85 (m, 1H), 7.73-7.70 (m, 1H), 6.67-6.63 (m, 1H), 6.48-6.47 (m, 1H), 6.30-6.27 (m, 2H), 0.63 (s, 6H)

Synthesis of Compound 31

5.04 g of Compound 31 was synthesized with a yield of 74% in the same manner as in the synthesis of Compound 2, except that 5.27 g (10 mmol) of Intermediate e and 2.2 g (10 mmol) of Intermediate 6 were used instead of Intermediates c and 1. The produced compound was identified using LC-MS and NMR. $C_{50}H_{39}N_3$:M+ 681.31

$^1$H NMR (CDCl$_3$, 400 MHz) δ (ppm) 8.24-8.22 (m, 1H), 8.15 (m, 1H), 7.78-7.73 (m, 2H), 7.67-7.64 (m, 1H), 7.58-7.55 (m, 3H), 7.52-7.47 (m, 4H), 7.39-7.27 (m, 4H), 7.21-7.19 (m, 1H), 7.14-7.09 (m, 2H), 7.05-7.01 (m, 2H), 6.90 (m, 1H), 6.71-6.67 (m, 3H), 6.58-6.51 (m, 4H), 6.42-6.41 (m, 1H), 3.47 (s, 3H), 1.61 (s, 6H)

Synthesis of Compound 3

5.31 g of Compound 3 was synthesized with a yield of 88% in the same manner as in the synthesis of Compound 2, except that 2.34 g (10 mmol) of Intermediate 8 was used instead of Intermediate 1. The produced compound was identified using LC-MS and NMR $C_{44}H_{33}N_3$ M+603.27

$^1$NMR (CDCl$_3$, 400 MHz) δ (ppm) 8.56 (d, 1H), 7.84-6.98 (m, 20H), 6.75 (s, 2H), 6.58-6.55 (m, 3H), 6.28 (d, 1H), 10.67 (s, 6H)

Synthesis of Compound 33

6.05 g of Compound 33 was synthesized with a yield of 89% in the same manner as in the synthesis of Compound 2, except that 5.27 g (10 mmol) of Intermediate e and 2.34 g (10 mmol) of Intermediate 9 was used instead of intermediates c and 1, respectively. The produced compound was identified using LC-MS and NMR. $C_{50}H_{37}N_3$: M+679.30

$^1$NMR (CDCl$_3$, 400 MHz) δ (ppm) 8.56 (d, 1H), 7.84-6.98 (m, 24H), 6.75 (s, 1H), 6.58-6.52 (m, 5H), 1.67 (s, 6H)

Compounds A to G

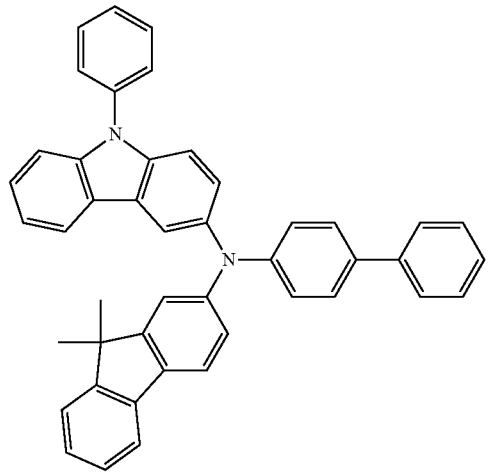

A

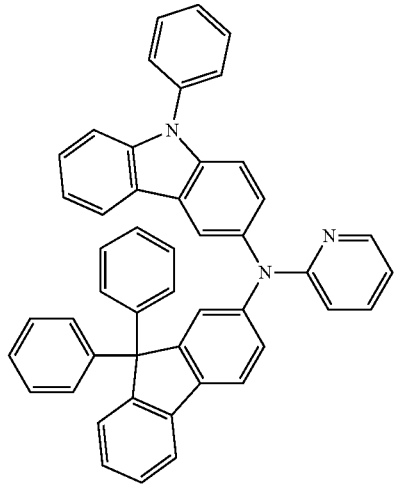

B

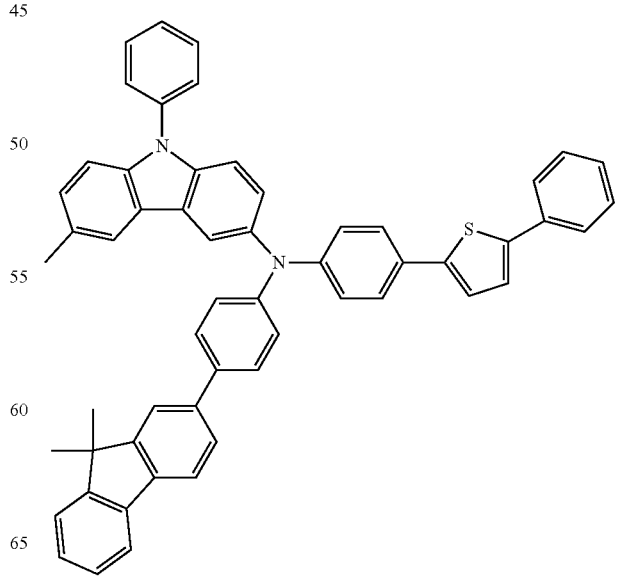

C

D
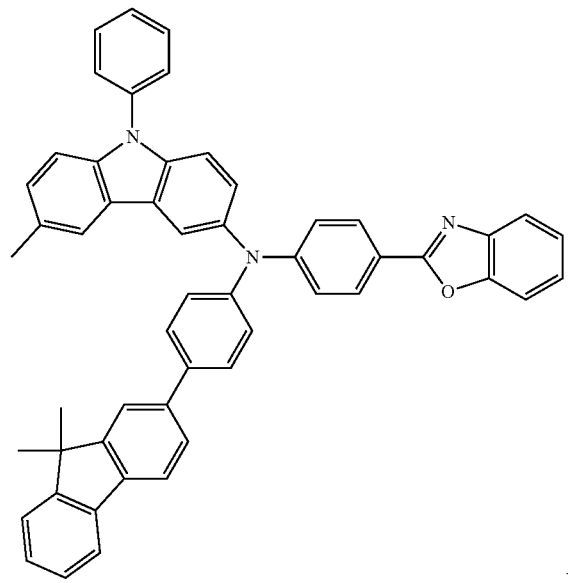
E
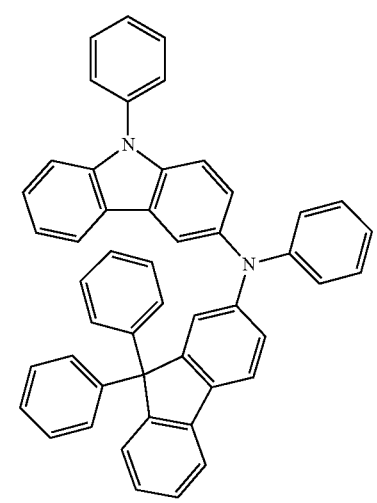
F
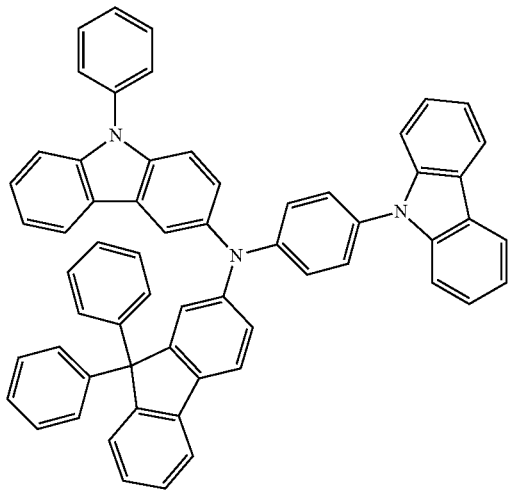
G
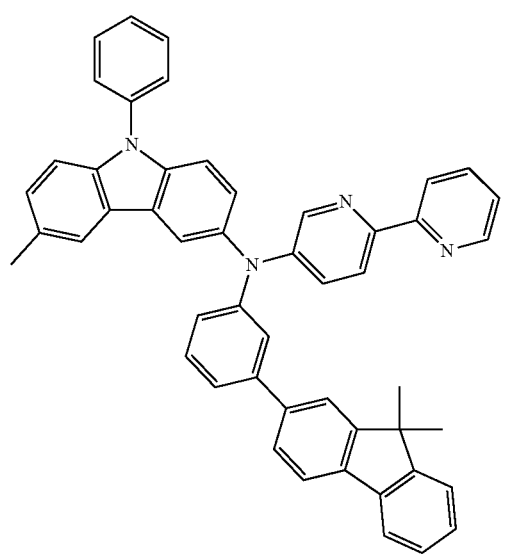
Reaction Scheme for Synthesizing Compounds A to G
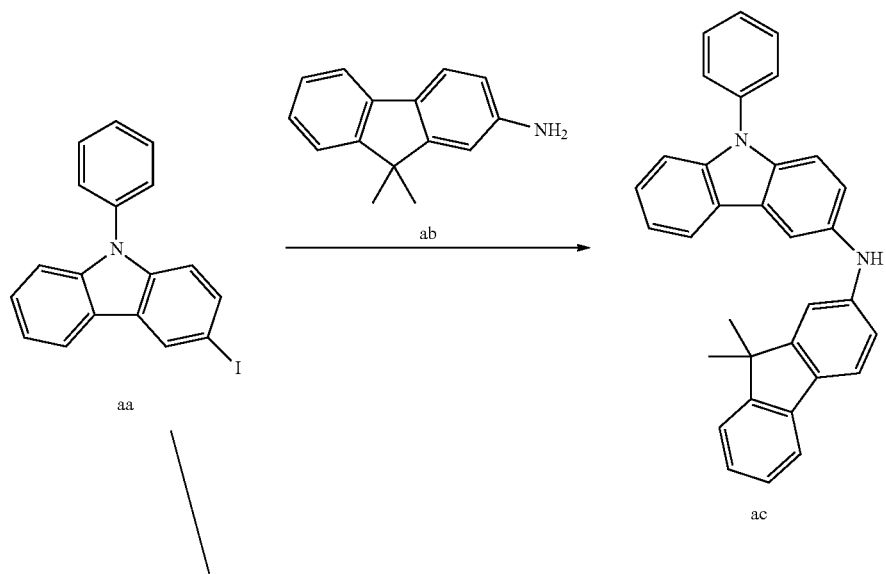

-continued
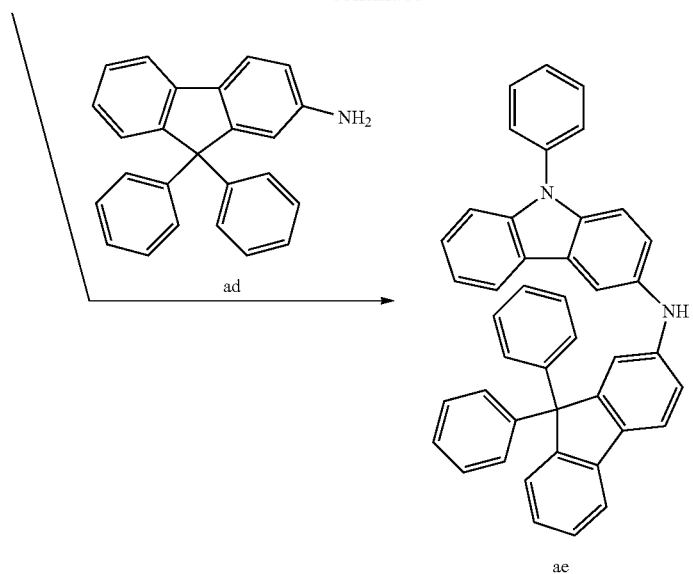
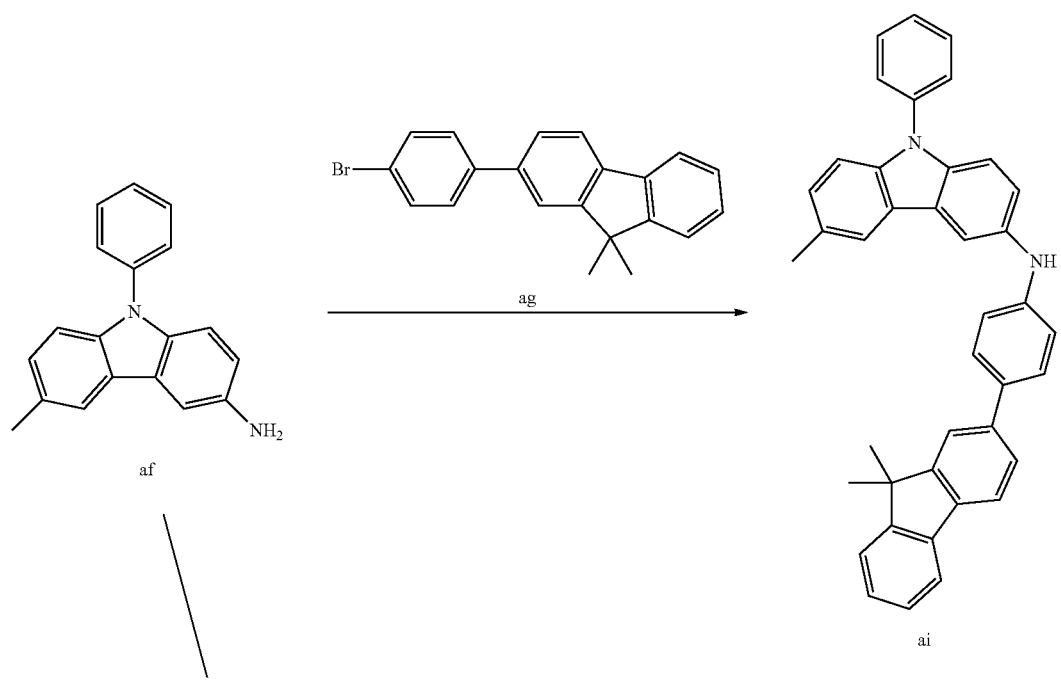

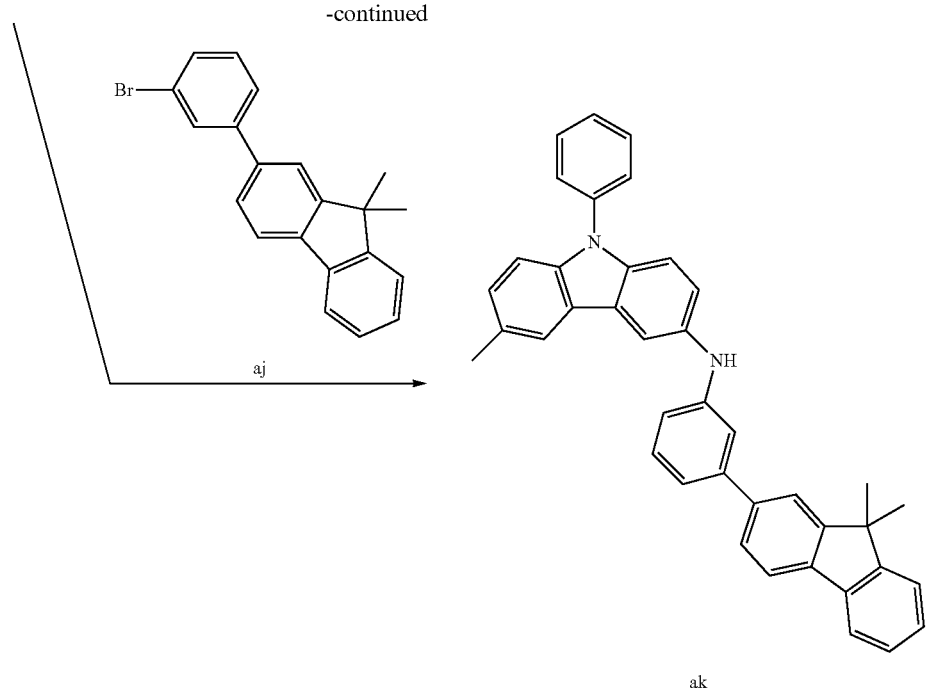

Synthesis of Intermediate ac

Intermediate ac was synthesized in the same manner as in the synthesis of Intermediate c (Intermediate aa=Intermediate b, and Intermediate ab=Intermediate a).

Synthesis of Intermediate ae 12.1 g of Intermediate ae was synthesized with a yield of 65% in the same manner as in the synthesis of Intermediate e, except that 18.5 g (50 mmol) of Intermediate aa and 16.7 g (50 mmol) of Intermediate ad were used instead of Intermediates a and d, and the produced compound was identified using LC-MS. $C_{48}H_{30}N_2$:M+ 574.24

Synthesis of Intermediate ai 16.5 g of Intermediate ai was synthesized with a yield of 61% in the same manner as in the synthesis of Intermediate e, except that 13.6 g (50 mmol) of Intermediate of and 17.5 g (50 mmol) of Intermediate ag were used instead of Intermediates a and d, and the produced compound was identified using LC-MS. $C_{40}H_{32}N_2$:M+ 540.26

Synthesis of Intermediate ak 17.8 g of Intermediate ak was synthesized with a yield of 66% in the same manner as in the synthesis of Intermediate e, except that 13.6 g (50 mmol) of Intermediate of and 17.5 g (50 mmol) of Intermediate aj were used instead of Intermediates a and d, and the produced compound was identified using LC-MS. $C_{40}H_{32}N_2$:M+ 540.26

Intermediates 11 to 17

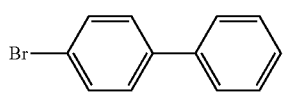

11

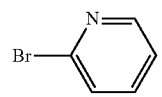

12

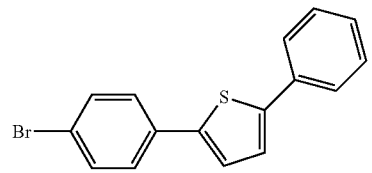

13

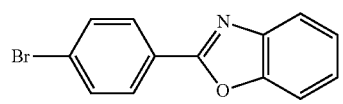

14

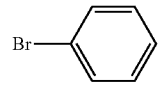

15

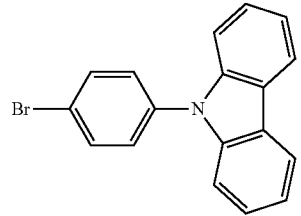

16

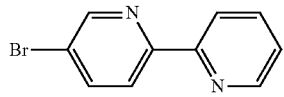

17

Reaction Scheme for Synthesizing Compounds A to G
ac + 11 ⟶
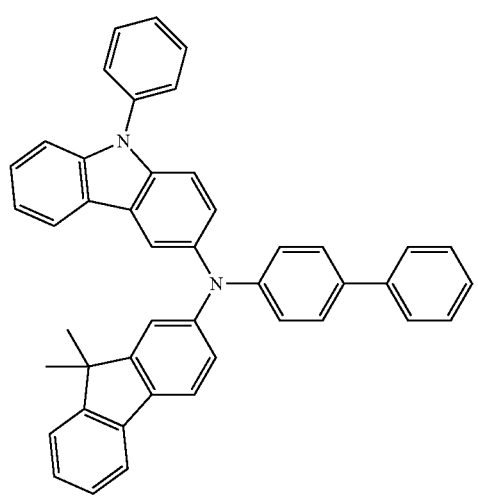
A
ae + 12 ⟶
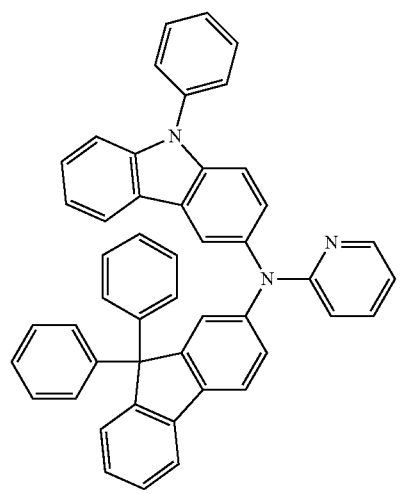
B
ai + 13 ⟶
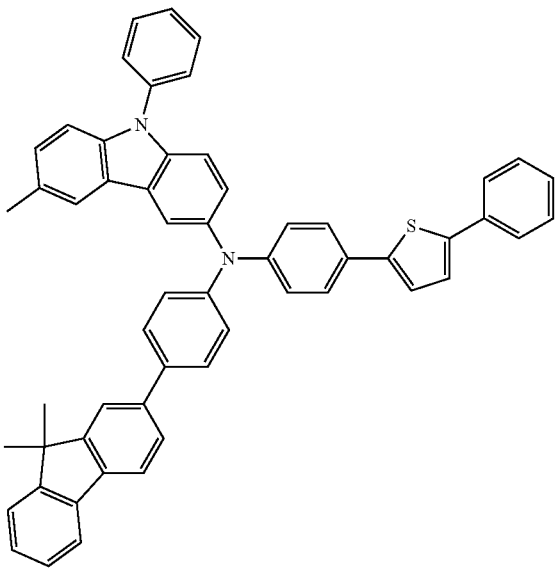
C
ai + 14 ⟶
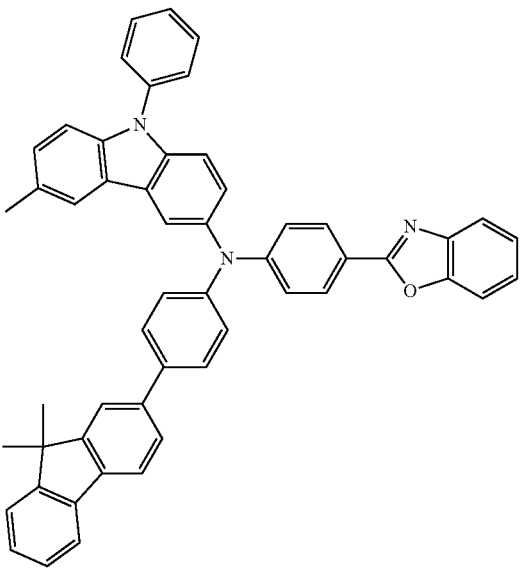
D ae + 15 ⟶ E

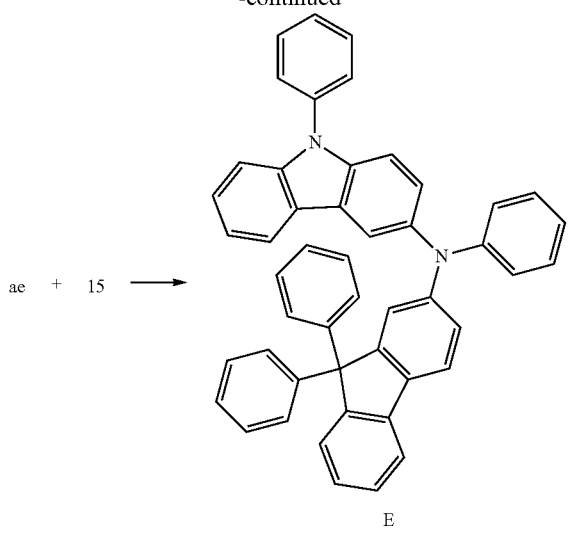

ae + 16 ⟶ F ak + 17 ⟶ G

Synthesis of Compound A 4.51 g (10 mmol) of Intermediate ac, 2.33 g (10 mmol) of Intermediate 11, 270 mg (3.0 mole %) of $Pd_2(dba)_3$, 1.4 g (15 mmol) of sodium tert-butoxide, and 60 mg (3.0 mole %) of $P(t-Bu)_3$ were added to 100 mL of toluene, and the mixture was refluxed while stirring at 100° C. for 5 hours. The reaction mixture was cooled to room temperature and subjected to extraction with methylene chloride and $H_2O$. Then, the resultant was dried using magnesium sulfate to evaporate the solvent. The residue was separately purified using silica gel column chromatography to obtain Compound A (Yield: 87%). The produced compound was identified using LC-MS and NMR. $C_{45}H_{34}N_2$ $M^+$ 602.27

$^1$H NMR ($CDCl_3$, 400 MHz) δ 8.23-8.20 (m, 1H), 7.82 (m, 1H), 7.78-7.76 (m, 1H), 7.64-7.72 (m, 2H), 7.58-7.56 (m, 1H), 7.53-7.24 (m, 13H), 7.14-7.08 (m, 3H), 6.96-6.93 (m, 2H), 6.76-6.73 (m, 1H), 6.59-6.56 (m, 2H), 6.52 (m, 1H), 1.61 (s, 6H)

Synthesis of Compound B

Compound B was synthesized with a yield of 73% in the same manner as in the synthesis of Compound A, except that 1.58 g (10 mmol) of Intermediate 12 was used instead of Intermediate 11. The produced compound was identified using LC-MS and NMR. $C_{48}H_{33}N_3$ $M^+$ 651.27

$^1$H NMR ($CDCl_3$, 400 MHz) δ8.23-8.19 (m, 2H), 7.86-7.85 (m, 1H), 7.54-7.42 (m, 7H), 7.39-7.35 (m, 1H), 7.31-7.06 (m, 17H), 6.92-6.89 (m, 1H), 6.81-6.76 (m, 2H), 6.65-6.62 (m, 1H), 6.57 (m, 1H)

Synthesis of Compound C

Compound C was synthesized with a yield of 71% in the same manner as in the synthesis of Compound A, except that 5.41 g (10 mmol) of Intermediate ai and 3.15 g (10 mmol) of Intermediate 13 were used instead of Intermediates ac and 11. The produced compound was identified using LC-MS and NMR. $C_{56}H_{42}N_2S$, $M^+$ 774.31

$^1$H NMR ($CDCl_3$, 400 MHz) δ7.81-7.79 (m, 1H), 7.77 (s, 1H), 7.73-7.70 (m, 1H), 7.65 (m, 1H), 7.61-7.59 (m, 2H), 7.52-7.09 (m, 21H), 7.07-7.06 (m, 1H), 6.69-6.65 (m, 2H), 6.61-6.56 (m, 2H), 2.56 (s, 4H), 1.57 (s, 6H)

Synthesis of Compound D

Compound D was synthesized with a yield of 77% in the same manner as in the synthesis of Compound A, except that 5.41 g (10 mmol) of Intermediate ai and 2.74 g (10 mmol) of Intermediate 14 were used instead of Intermediates ac and 11. The produced compound was identified using LC-MS and NMR. $C_{53}H_{39}N_3O_1$ $M^+$ 733.31

$^1$H NMR ($CDCl_3$, 400 MHz) δ 8.12-8.08 (m, 2H), 7.81-7.79 (m, 1H), 7.77 (s, 1H), 7.73-7.71 (m, 2H), 7.65 (m, 1H), 7.52-7.47 (m, 5H), 7.43-7.09 (m, 13H), 6.90-6.87 (m, 2H), 6.61-6.50 (m, 3H), 2.56 (s, 3H), 1.57 (s, 6H)

Synthesis of Compound E

Compound E was synthesized with a yield of 84% in the same manner as in the synthesis of Compound A, except that 5.75 g (10 mmol) of Intermediate ae and 1.57 g (10 mmol) of Intermediate 15 were used instead of Intermediates ac and 11. The produced compound was identified using LC-MS and NMR. $C_{49}H_{34}N_2$ $M^+$ 650.27

¹H NMR (CDCl₃, 400 MHz) δ 8.23-8.20 (m, 1H), 7.86-7.85 (m, 1H), 7.54-7.23 (m, 12H), 7.18-7.05 (m, 13H), 6.87-6.84 (m, 1H), 6.81-6.79 (m, 1H), 6.66-6.63 (m, 2H), 6.54 (m, 1H), 6.30-6.28 (m, 2H)

Synthesis of Compound F

Compound F was synthesized with a yield of 85% in the same manner as in the synthesis of Compound A, except that 5.75 g (10 mmol) of Intermediate ae and 3.22 g (10 mmol) of Intermediate 16 were used instead of Intermediates ac and 11. The produced compound was identified using LC-MS and NMR. $C_{61}H_{41}N_3$ M⁺ 815.33

¹H NMR (CDCl₃, 400 MHz) δ 8.23-8.20 (m, 1H), 8.12-8.10 (d, 2H), 7.86-7.85 (m, 1H), 7.54-7.49 (m, 4H), 7.48-7.06 (m, 27H), 6.81-6.79 (m, 1H), 6.76-6.68 (m, 3H), 6.58 (m, 1H), 6.53-6.51 (m, 1H)

Synthesis of Compound G

Compound G was synthesized with a yield of 72% in the same manner as in the synthesis of Compound A, except that 5.41 g (10 mmol) of Intermediate ak and 2.35 g (10 mmol) of Intermediate 17 were used instead of Intermediates ac and 11. The produced compound was identified using LC-MS and NMR. $C_{50}H_{38}N_4$ M⁺ 694.31

¹H NMR (CDCl₃, 400 MHz) δ 8.71-8.70 (m, 1H), 8.38-8.36 (m, 1H), 8.17 (m, 1H), 8.12-8.10 (m, 1H), 7.84-7.79 (m, 3H), 7.77 (s, 1H), 7.70-7.68 (m, 1H), 7.64 (m, 1H), 7.52-7.41 (m, 6H), 7.35-7.09 (m, 11H), 7.02 (m, 1H), 6.65-6.63 (m, 1H), 6.31-6.26 (m, 1H), 2.56 (s, 3H), 1.57 (s, 6H)

Example 1

A Corning 15 Ω/cm² (1200 Å) ITO glass substrate was cut to a size of 50 mm×50 mm×0.7 mm, sonicated using isopropyl alcohol and pure water for five minutes each, and then cleaned by irradiation of UV rays for 30 minutes and exposure to ozone. Then, resulting glass substrate was disposed in a vacuum deposition apparatus.

Then, 2-TNATA was deposited on the ITO glass substrate to form a HIL having a thickness of 600 Å, and then Compound 2 was deposited on the HIL to form a HTL having a thickness of 300 Å.

Then, ADN and DPVBi were co-deposited on the HTL in a weight ratio of 98:2 to form an EML with a thickness of 300 Å.

Then, Alq3 was deposited on the EML to form an ETL having a thickness of 300 Å, and LiF was deposited on the ETL to form an EIL having a thickness of 10 Å. Then, Al was deposited on the EIL to a thickness of 3000 Å, thereby forming a second electrode (cathode). As a result, an organic light-emitting diode emitting blue light was prepared.

Example 2

An organic light-emitting diode was manufactured in the same manner as in Example 1, except that Compound 8 was used instead of Compound 2 when the HTL is formed.

Example 3

An organic light-emitting diode was manufactured in the same manner as in Example 1, except that Compound 14 was used instead of Compound 2 when the HTL is formed.

Example 4

An organic light-emitting diode was manufactured in the same manner as in Example 1, except that Compound 15 was used instead of Compound 2 when the HTL is formed.

Example 5

An organic light-emitting diode was manufactured in the same manner as in Example 1, except that Compound 16 was used instead of Compound 2 when the HTL is formed.

Example 6

An organic light-emitting diode was manufactured in the same manner as in Example 1, except that Compound 20 was used instead of Compound 2 when the HTL is formed.

Example 7

An organic light-emitting diode was manufactured in the same manner as in Example 1, except that Compound 31 was used instead of Compound 2 when the HTL is formed.

Example 8

An organic light-emitting diode was manufactured in the same manner as in Example 1, except that Compound 3 was used instead of Compound 2 when the HTL is formed.

Example 9

An organic light-emitting diode was manufactured in the same manner as in Example 1, except that Compound 33 was used instead of Compound 2 when the HTL is formed.

Comparative Example 1

An organic light-emitting diode was manufactured in the same manner as in Example 1, except that Compound A was used instead of Compound 2 when the HTL is formed.

Comparative Example 2

An organic light-emitting diode was manufactured in the same manner as in Example is 1, except that Compound B was used instead of Compound 2 when the HTL is formed.

Comparative Example 3

An organic light-emitting diode was manufactured in the same manner as in Example 1, except that Compound C was used instead of Compound 2 when the HTL is formed.

Comparative Example 4

An organic light-emitting diode was manufactured in the same manner as in Example 1, except that Compound D was used instead of Compound 2 when the HTL is formed.

Comparative Example 5

An organic light-emitting diode was manufactured in the same manner as in Example 1, except that Compound E was used instead of Compound 2 when the HTL is formed.

Comparative Example 6

An organic light-emitting diode was manufactured in the same manner as in Example 1, except that Compound F was used instead of Compound 2 when the HTL is formed.

Comparative Example 7

An organic light-emitting diode was manufactured in the same manner as in Example 1, except that Compound G was used instead of Compound 2 when the HTL is formed.

Evaluation Example 1

Driving voltage, current density, brightness, color of emitted light, efficiency, and half lifetime of the organic light-emitting diodes manufactured according to Examples 1 to 9 and Comparative Examples 1 to 7 were evaluated using a PR650 Spectroscan Source Measurement Unit (PhotoResearch). The results are shown in Table 1 below.

TABLE 1

| | HTL | Driving voltage (V) | Current density (mA/cm$^2$) | Brightness (cd/m$^2$) | Efficiency (cd/A) | Color | Half lifetime (hr) |
|---|---|---|---|---|---|---|---|
| Example 1 | Compound 2 | 6.67 | 50 | 2,433 | 4.87 | blue | 293 |
| Example 2 | Compound 8 | 6.53 | 50 | 2,547 | 5.09 | blue | 302 |
| Example 3 | Compound 14 | 6.58 | 50 | 2,663 | 5.33 | blue | 285 |
| Example 4 | Compound 15 | 6.68 | 50 | 2,770 | 5.54 | blue | 334 |
| Example 5 | Compound 16 | 6.71 | 50 | 2,598 | 5.20 | blue | 317 |
| Example 6 | Compound 20 | 6.76 | 50 | 2,238 | 4.90 | blue | 287 |
| Example 7 | Compound 31 | 6.62 | 50 | 2,552 | 5.10 | blue | 304 |
| Example 8 | Compound 3 | 6.50 | 50 | 2,835 | 5.67 | blue | 359 |
| Example 9 | Compound 33 | 6.47 | 50 | 2,865 | 5.71 | blue | 342 |
| Comparative Example 1 | Compound A | 7.85 | 50 | 1,561 | 3.12 | blue | 113 |
| Comparative Example 2 | Compound B | 8.04 | 50 | 1,316 | 2.63 | blue | 104 |
| Comparative Example 3 | Compound C | 7.49 | 50 | 1,472 | 2.94 | blue | 97 |
| Comparative Example 4 | Compound D | 7.27 | 50 | 1,245 | 2.49 | blue | 107 |
| Comparative Example 5 | Compound E | 7.95 | 50 | 1,183 | 2.37 | blue | 95 |
| Comparative Example 6 | Compound F | 7.74 | 50 | 1,627 | 3.25 | blue | 120 |
| Comparative Example 7 | Compound G | 7.89 | 50 | 1,255 | 2.51 | blue | 109 |

Referring to Table 1, it was identified that the organic light-emitting diodes manufactured according to Examples 1 to 9 had lower driving voltage, higher brightness, higher efficiency, higher color purity, and longer lifetime than the organic light-emitting diodes manufactured according to Comparative Examples 1 to 7.

Example 11

A Corning 15 Ω/cm$^2$ (1200 Å) ITO glass substrate was cut to a size of 50 mm×50 mm×0.7 mm, sonicated using isopropyl alcohol and pure water for five minutes each, and then cleaned by irradiation of UV rays for 30 minutes and exposure to ozone. Then, resulting glass substrate was disposed in a vacuum deposition apparatus.

Then, 2-TNATA was deposited on the ITO glass substrate to form a HIL having a thickness of 600 Å, and then Compound 300, Compound 15, and F4-CTNQ (p-dopant) were co-12 deposited on the HIL to form a HTL having a thickness of 1140 Å, wherein the weight ratio of Compound 300:Compound 15 was 70:30, and the amount of the p-dopant was 1% by weight based on 100% by weight of the total amount of Compound 300 and Compound 15.

Then, Compound 300 was deposited on the HTL to form a buffer layer having a thickness of 230 Å, and ADN and DPVBi were co-deposited on the buffer layer in a weight ratio of 98:2 to form an EML having a thickness of 300 Å.

Then, Alq3 was deposited on the EML to form an ETL having a thickness of 300 Å, and LiF was deposited on the ETL to form an EIL having a thickness of 10 Å. Then, Al was deposited on the EIL to a thickness of 3000 Å, thereby forming a second electrode (cathode). As a result, an organic light-emitting diode emitting blue light was prepared.

Example 12

An organic light-emitting diode was prepared in the same manner as in Example 11, except that Compound 300 and Compound 16 were co-deposited to form a HTL having a thickness of 1320 Å, and the thickness of the buffer layer was 50 Å, wherein the weight ratio of Compound 300:Compound 16 was 70:30.

Example 13

An organic light-emitting diode was prepared in the same manner as in Example 12, except that Compound 300 and Compound 16 were co-deposited to form a HTL having a thickness of 1270 Å, and the thickness of the buffer layer was 100 Å, wherein the weight ratio of Compound 300:Compound 16 was 70:30.

Comparative Example 11

An organic light-emitting diode was manufactured in the same manner as in Example 11, except that NPB was used instead of Compound 300 and Compound 15 during formation of the HTL and NPB was used instead of Compound 300 during formation of the buffer layer.

Evaluation Example 2

Driving voltage, current density, brightness, color of emitted light, efficiency, and half lifetime of the organic light emitting diodes manufactured according to Examples 11 to 13 and Comparative Example 11 were evaluated using PR650 Spectroscan Source Measurement Unit (PhotoResearch). The results are shown in Table 2 below, and FIG. 2 is a time-brightness graph of organic light-emitting diodes prepared according to Examples 11 to 13 and Comparative Example 11.

TABLE 2

|  | Example 11 | Example 12 | Example 13 | Comparative Example 11 |
|---|---|---|---|---|
| HIL | 2-TNATA (600 Å) | 2-TNATA (600 Å) | 2-TNATA (600 Å) | 2-TNATA (600 Å) |
| HTL | Co-deposition of Compound 300, Compound 15, and F4-CTNQ (1140 Å) | Co-deposition of Compound 300, Compound 16, and F4-CTNQ (1320 Å) | Co-deposition of Compound 300, Compound 16, and F4-CTNQ (1270 Å) | Co-deposition of NPB and F4-CTNQ (1140 Å) |
| Buffer layer | Compound 300 (230 Å) | Compound 300 (50 Å) | Compound 300 (100 Å) | NPB (230 Å) |
| Driving voltage (V) | 5.6 | 5.0 | 5.0 | 5.2 |
| Efficiency (cd/A) | 5.5 | 5.1 | 4.9 | 3.8 |
| CIE_x | 0.135 | 0.135 | 0.136 | 0.137 |
| CIE_y | 0.057 | 0.057 | 0.054 | 0.052 |
| Calculated efficiency (cd/A)/CIE_y | 95.3 | 89.4 | 90.7 | 72.8 |
| Half lifetime (hr) (@400 nit) | 68.0 | 263 | 225 | 26.0 |

Figure 2:
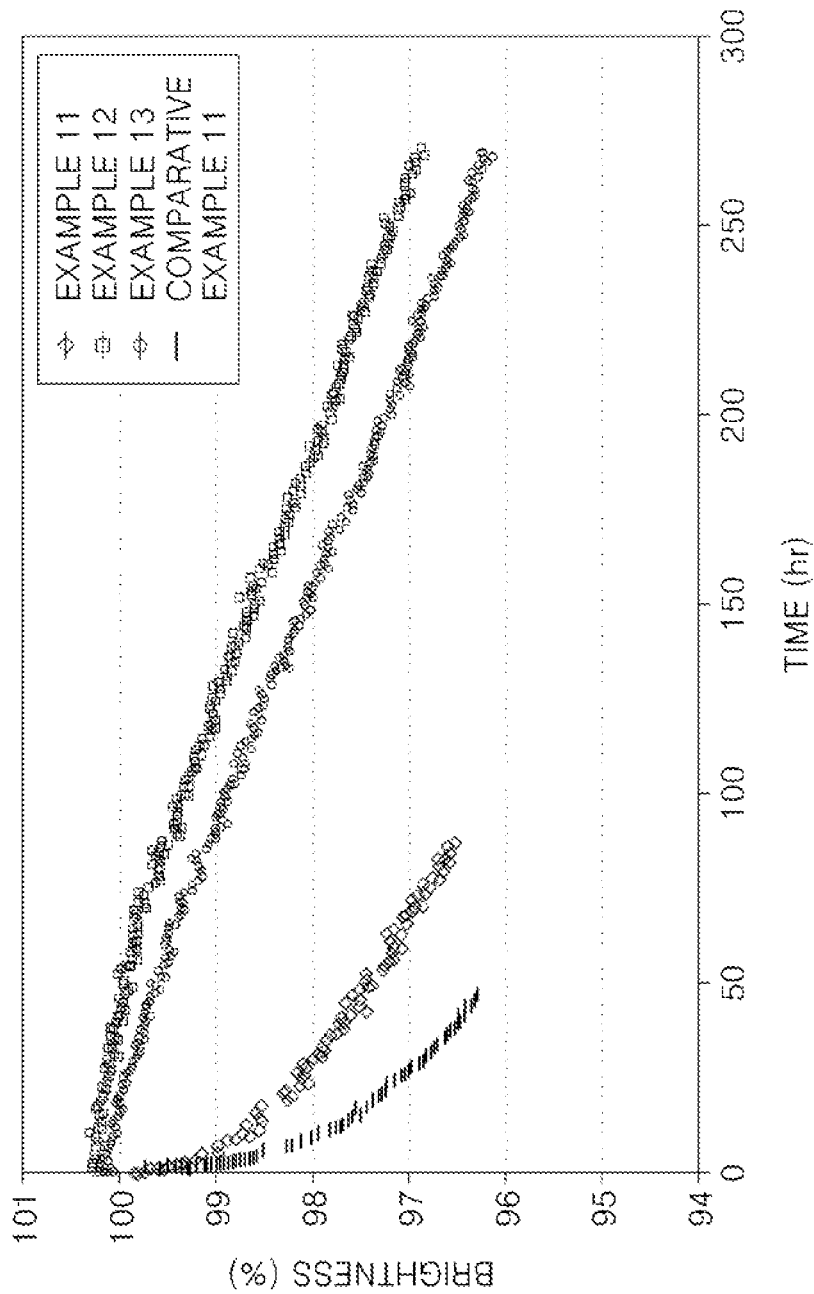
FIG. 2 is a time-brightness graph of organic light-emitting diodes prepared according to Examples 11 to 13 and Comparative Example 11.
Figure 3:
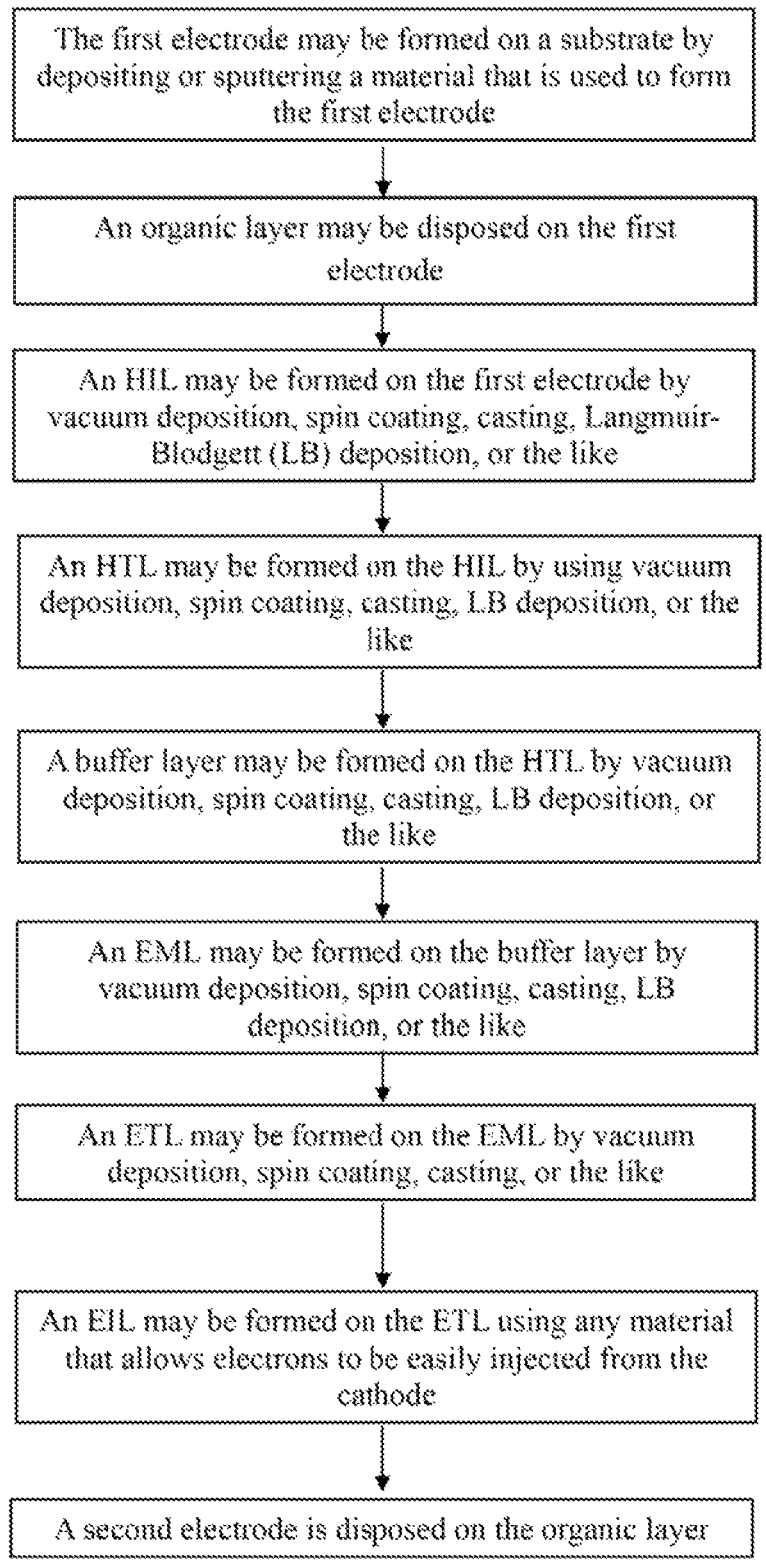
FIG. 3 is a flow-chart showing the preparation of an organic light-emitting diode of the present invention.

Referring to Table 2 and FIG. 2, it was identified that the organic light-emitting diodes manufactured according to Examples 11 to 13 had lower driving voltage, higher brightness, higher efficiency, higher color purity, and longer lifetime than the organic light-emitting diodes manufactured according to Comparative Example 11.

The organic light-emitting diode including the carbazole-based compound may have low driving voltage, high brightness, high efficiency, and long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A carbazole-based compound represented by Formula 1:

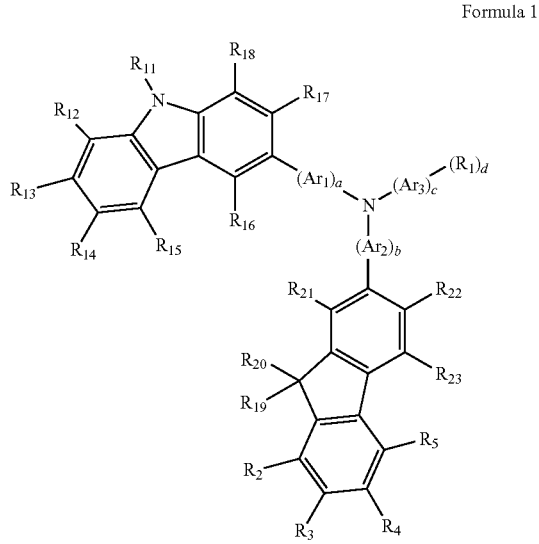

Formula 1 wherein $Ar_1$ to $Ar_3$ are each independently a substituted or unsubstituted $C_6$-$C_{60}$ arylene group;
a and b are each independently an integer from 0 to 5;
c is an integer from 1 to 5;

$R_1$ to $R_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{31}$)($R_{32}$)($R_{33}$), —N($R_{34}$)($R_{35}$) or a nitrogen-containing group, wherein at least one of $R_1$ or $R_3$ is a nitrogen-containing group;

d is an integer from 0 to 5;

$R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{36}$)($R_{37}$)($R_{38}$), or —N($R_{39}$)($R_{40}$);

$R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group; and the nitrogen-containing group is a 5-membered aromatic ring group, a 6-membered aromatic ring group, or a 9-membered aromatic ring group in which a 5-membered aromatic ring group and a 6-membered aromatic ring group are fused to each other, each of which includes at least one nitrogen atom as a ring atom, wherein the nitrogen-containing group is one of Formulae 3A to 3M below:

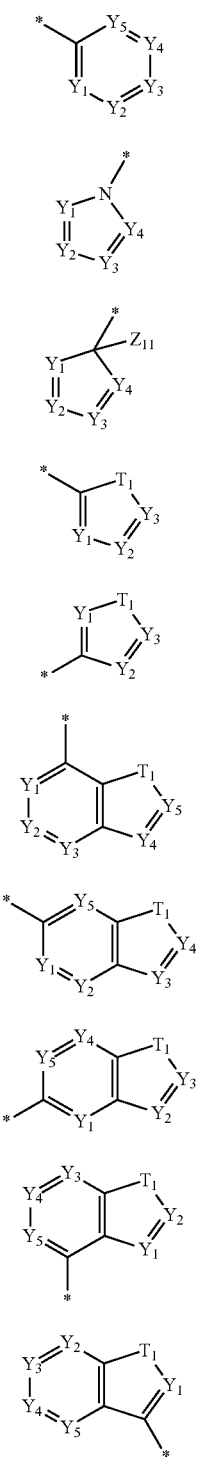

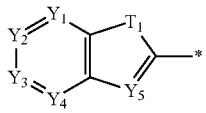

Formula 3K

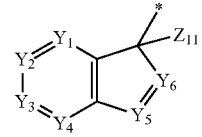

Formula 3L

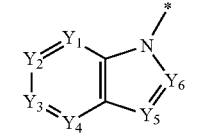

Formula 3M wherein $Y_1$ to $Y_6$ are each independently =N— or =C($Z_{12}$)—;

$T_1$ is —N($Z_{13}$)— or —C($Z_{14}$)($Z_{15}$)—;

$Z_{11}$ to $Z_{15}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group;

wherein in Formula 3F, 3G, 3H, 3I and 3K $T_1$ is —C($Z_{14}$)($Z_{15}$)—; and

* represents a chemical bond.

2. A carbazole-based compound of claim 1, wherein $Ar_1$ to $Ar_3$ are each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyranylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group.

3. A carbazole-based compound of claim 1, wherein $Ar_1$ to $Ar_3$ are each independently one of Formulae 2A to 2I below:

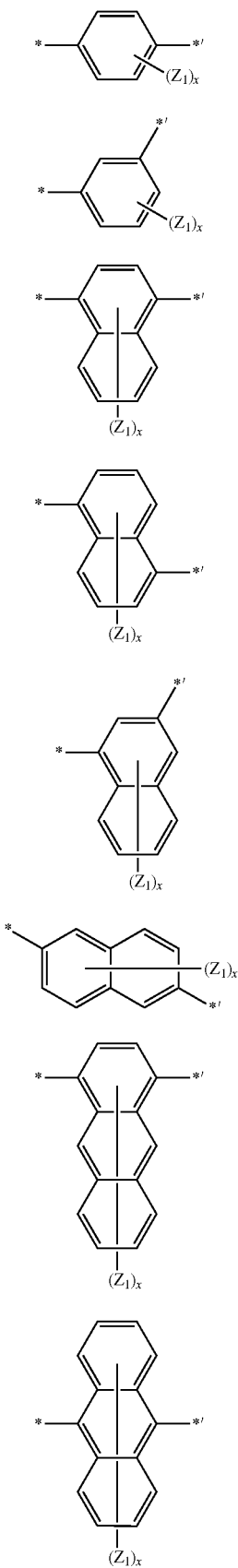

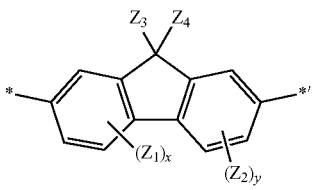

wherein $Z_1$ to $Z_4$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($Q_1$)($Q_2$)($Q_3$), or —N($Q_4$)($Q_5$);

$Q_1$ to $Q_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

x is an integer from 1 to 8;

y is an integer from 1 to 3; and

* is a binding site with nitrogen positioned at the center of Formula 1, and *' is a binding site with at least one $R_1$, a carbazole ring, or a fluorene ring in Formula 1.

4. A carbazole-based compound of claim 1, wherein $Z_{11}$ to $Z_{15}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_6$-$C_{20}$ aryl group.

5. A carbazole-based compound of claim 1, wherein $R_1$ is a nitrogen-containing group, and c and d are each independently 1 or 2.

6. A carbazole-based compound of claim 1, wherein $R_3$ is a nitrogen-containing group.

7. A carbazole-based compound of claim 1, represented by one of Formulae 1A to 1K below:

Formula 1A
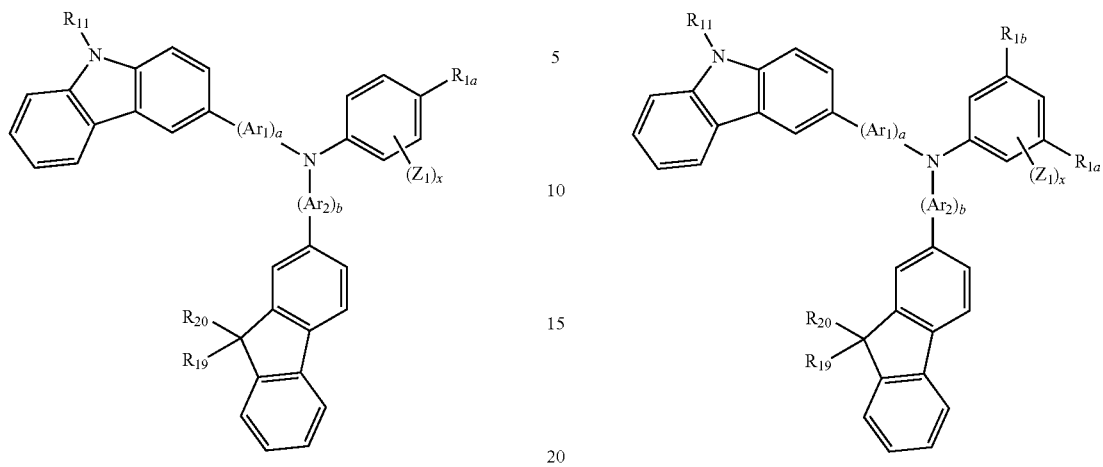
Formula 1B
Formula 1C
Formula 1D
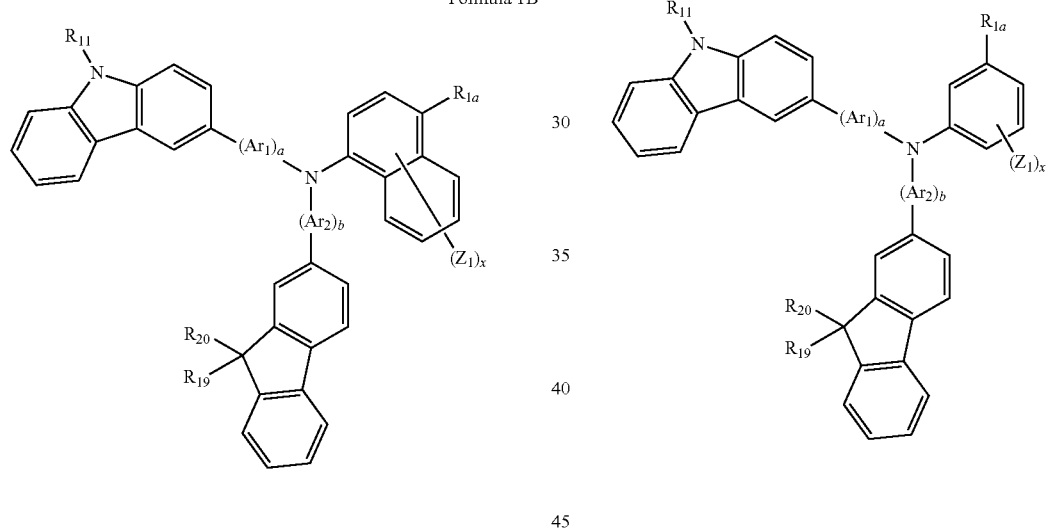
Formula 1E
Formula 1F
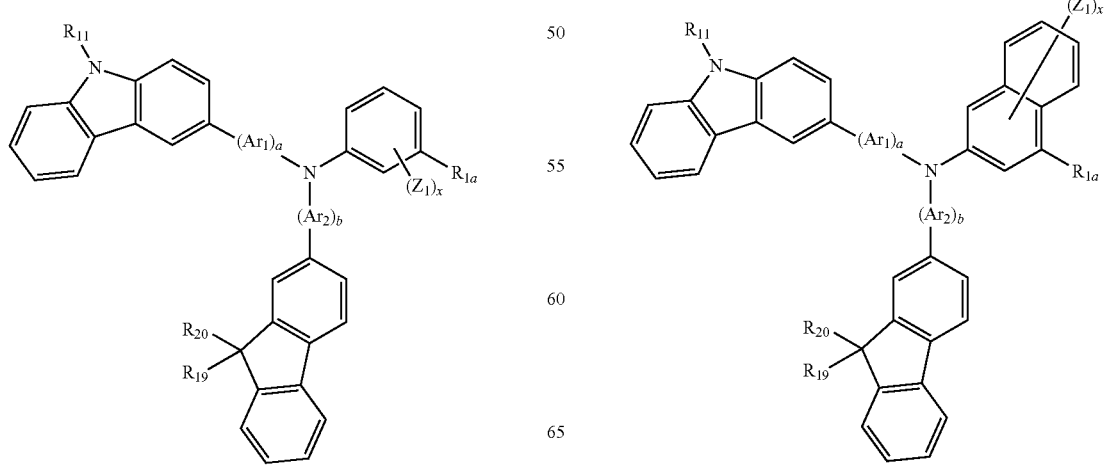

Formula 1G

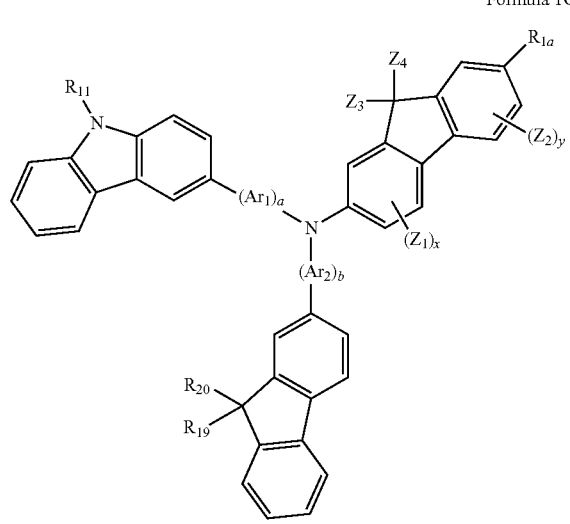

Formula 1H

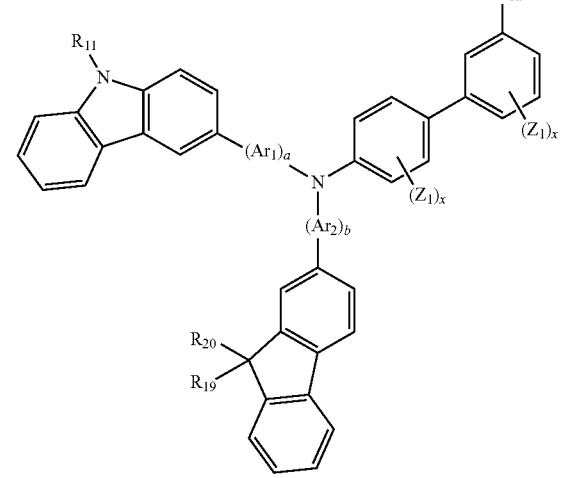

Formula 1I

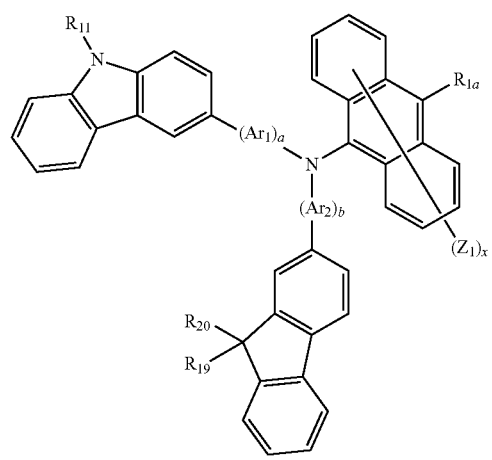

Formula 1J

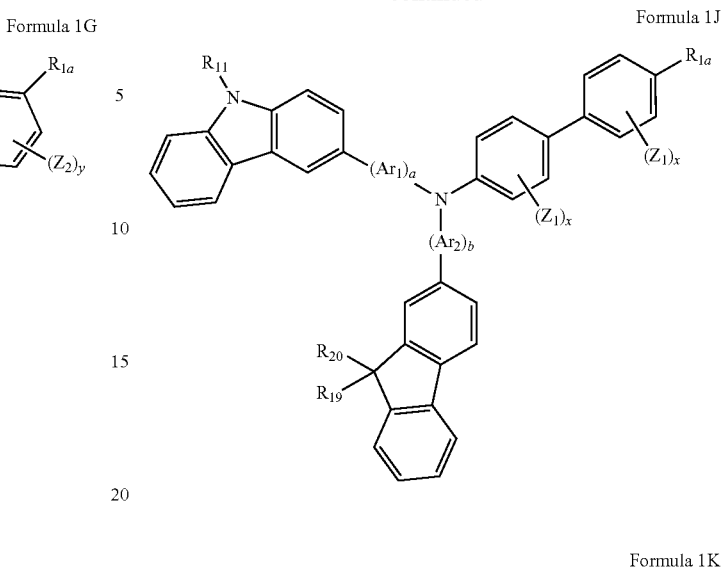

Formula 1K

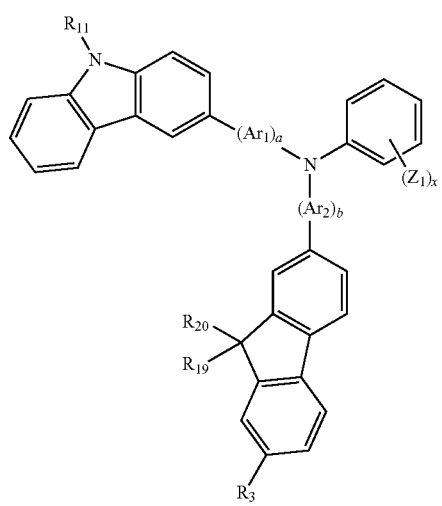

wherein $Ar_1$ and $Ar_2$ are each independently a substituted or unsubstituted $C_6$-$C_{60}$ arylene group;

a and b are each independently an integer from 0 to 5;

$R_{1a}$, $R_{1b}$ and $R_3$ are the nitrogen-containing group;

$R_{11}$, $R_{19}$ and $R_{20}$ are each independently a substituted or unsubstituted $C_1$-$C_{60}$ alkyl group or a substituted or unsubstituted $C_6$-$C_{60}$ aryl group;

$Z_1$ to $Z_4$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($Q_1$)($Q_2$)($Q_3$), or —N($Q_4$)($Q_5$);

Q₁ to Q₅ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

x is an integer from 1 to 8; and y is an integer from 1 to 3.

8. A carbazole-based compound of claim 1, of one of structures 1 to 33:

1

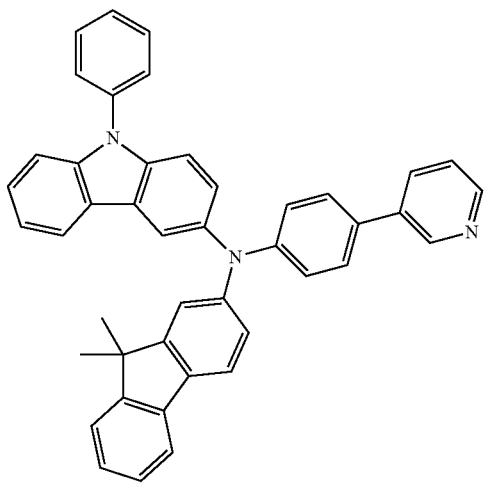

2

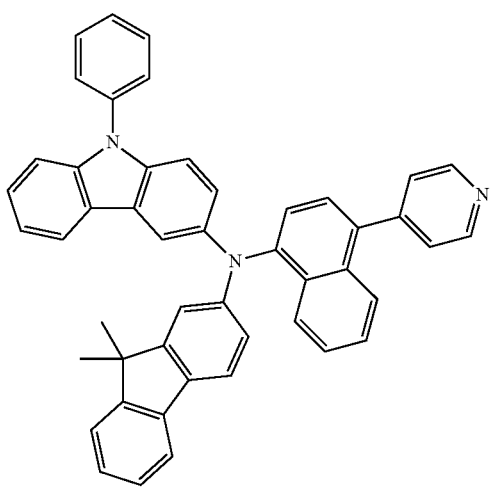

3

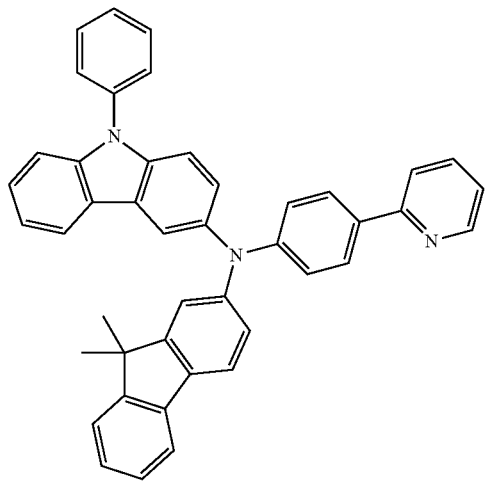

4

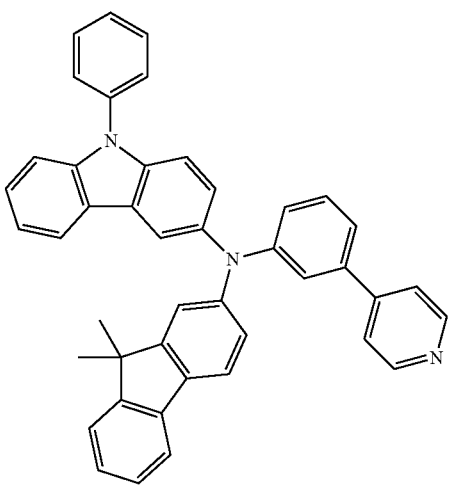

5

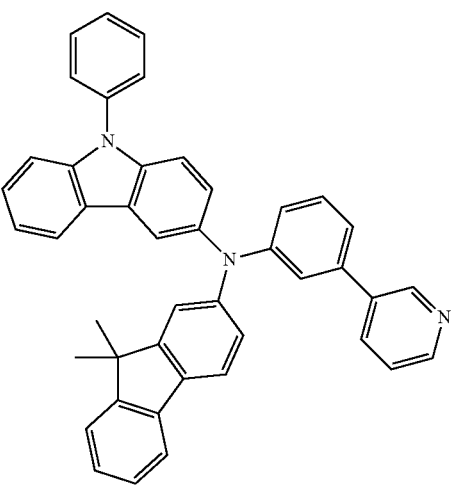

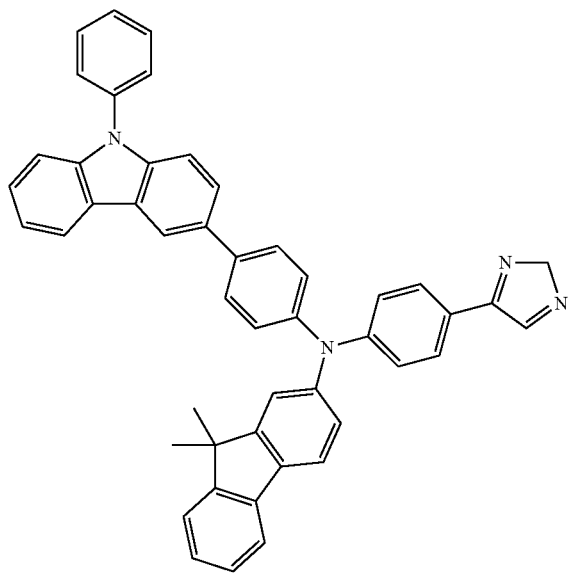
6
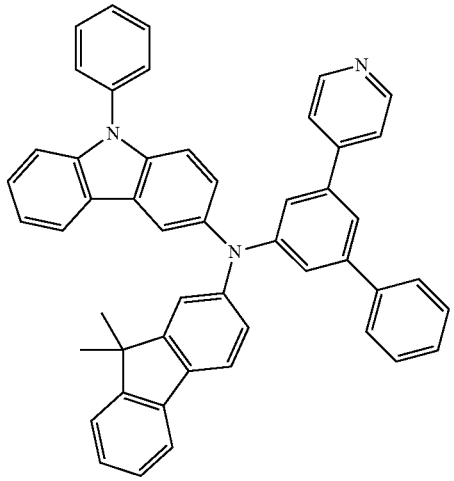
9
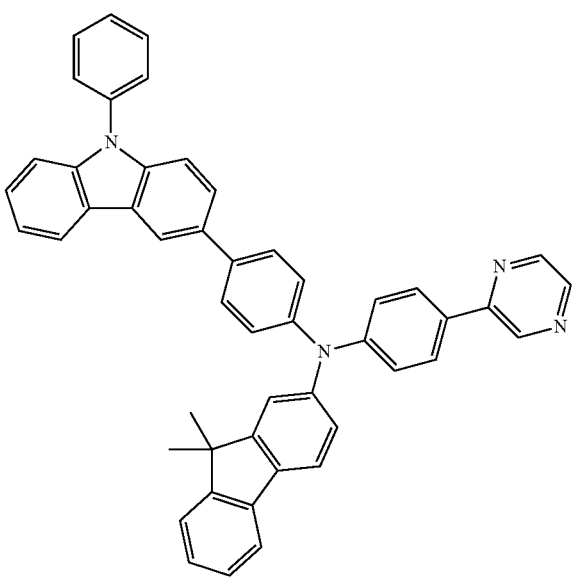
7
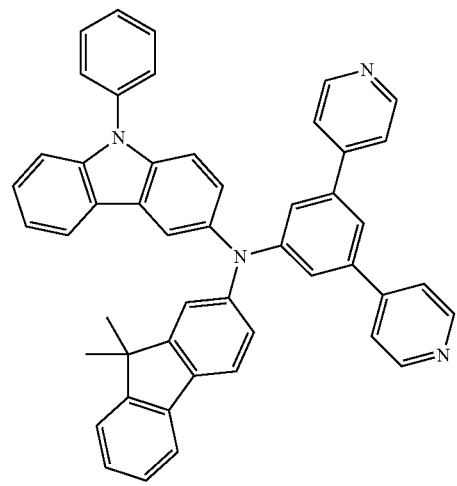
10
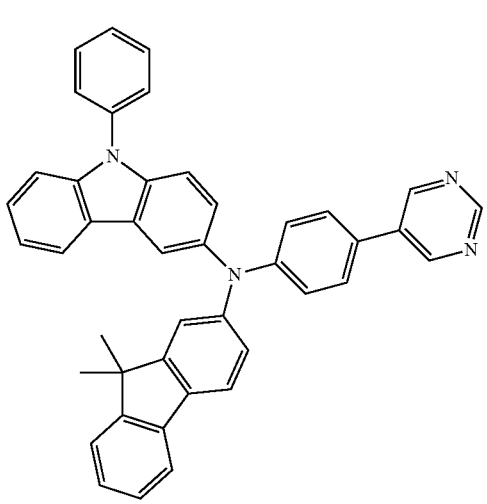
11

-continued
12
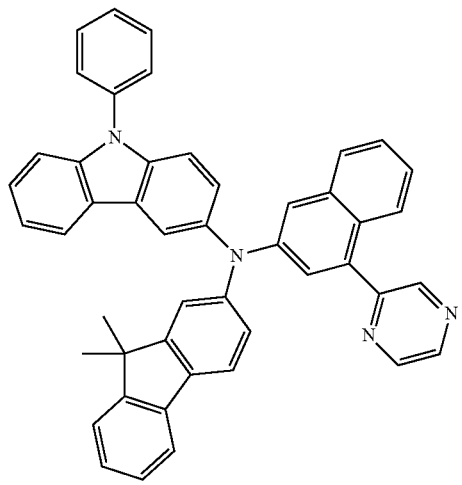
13
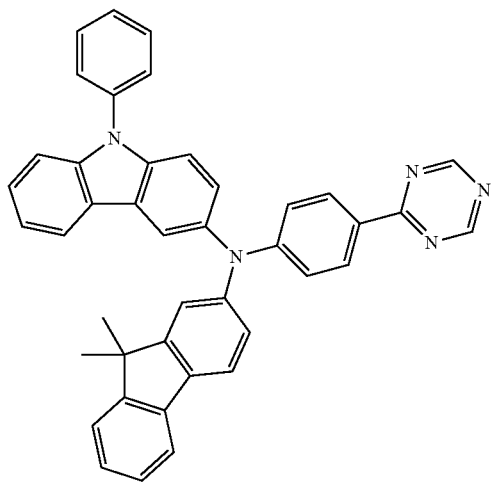
14
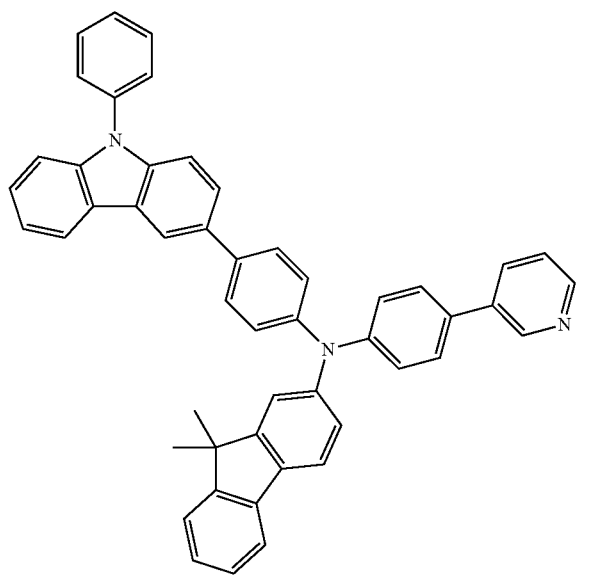
-continued
15
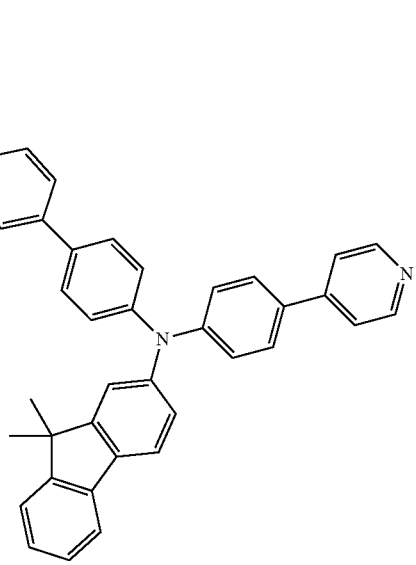
16
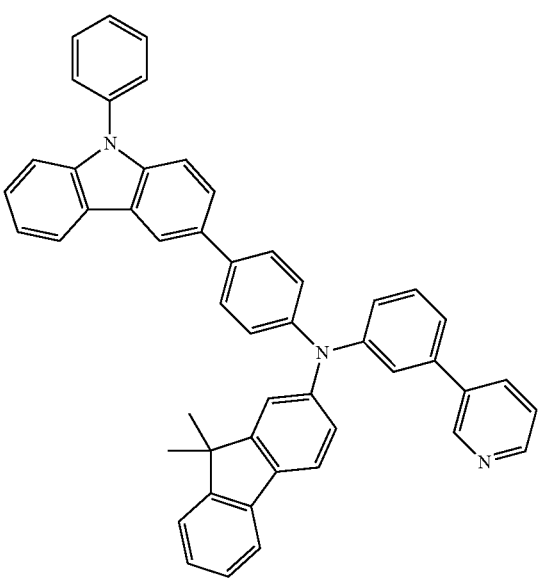

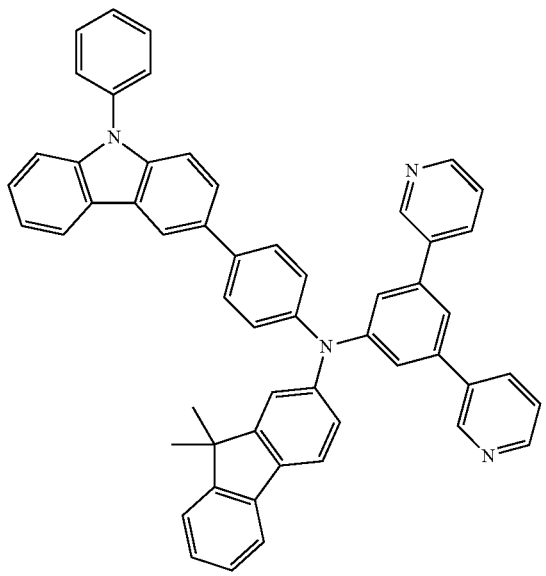
17
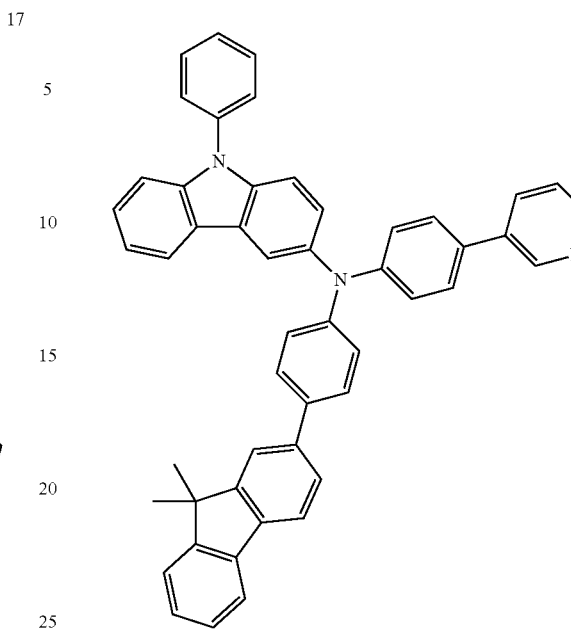
19
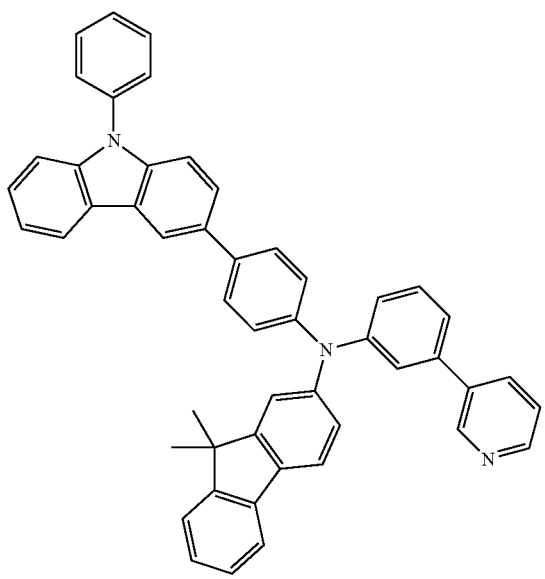
18
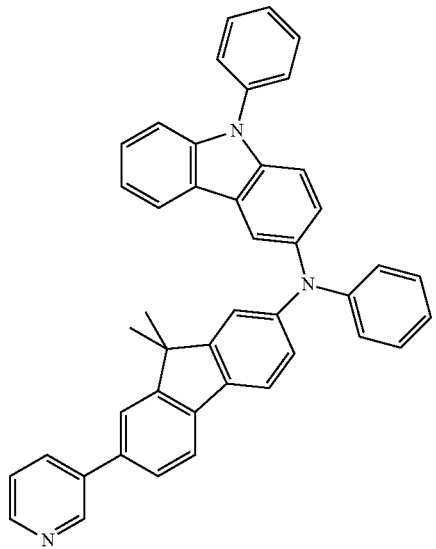
20

21
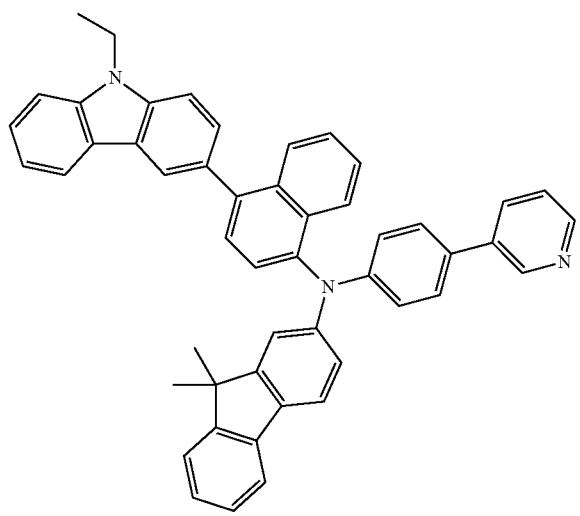
22
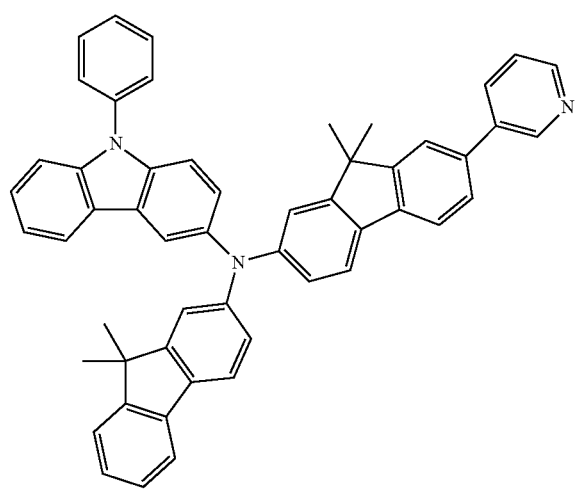
23
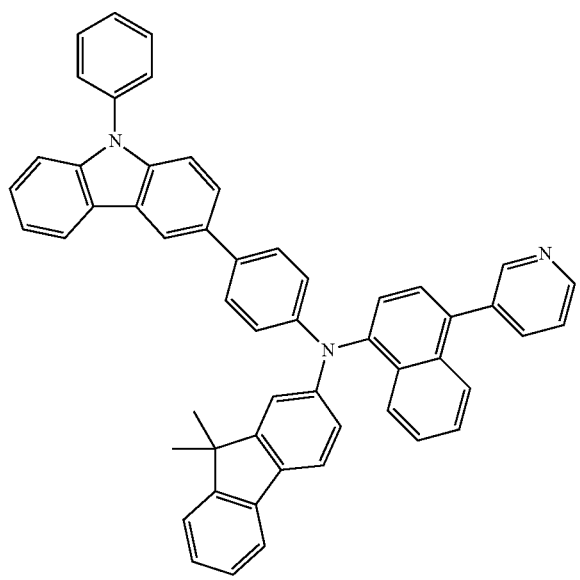
24
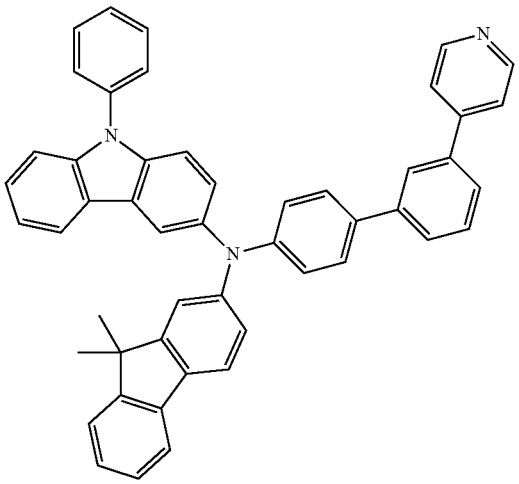
25
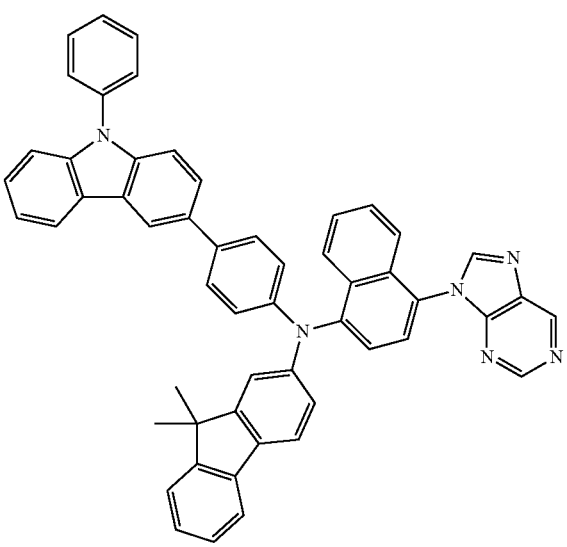
26
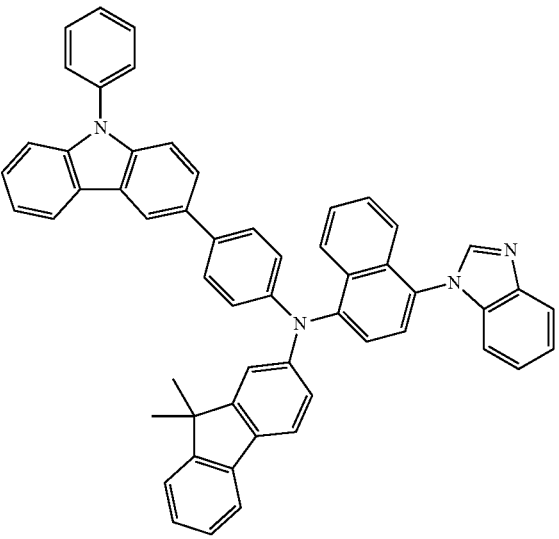

27
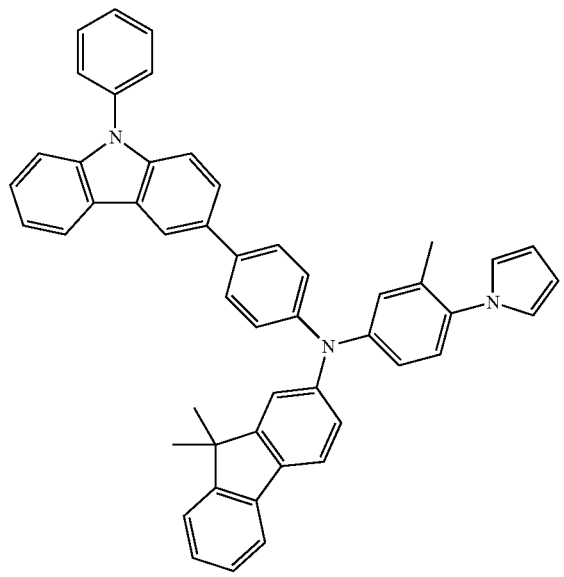
28
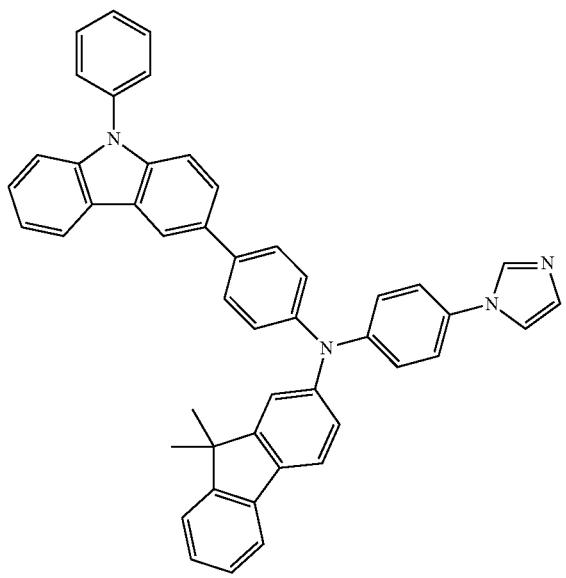
29
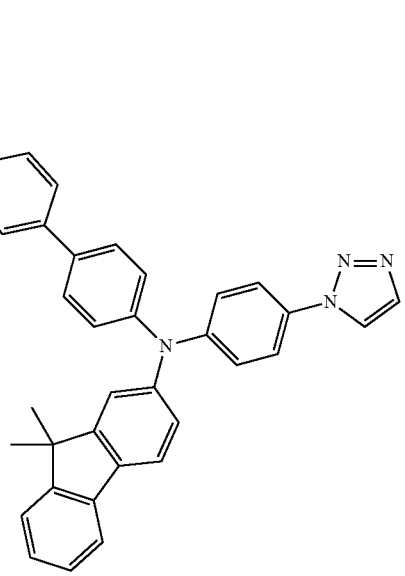
30
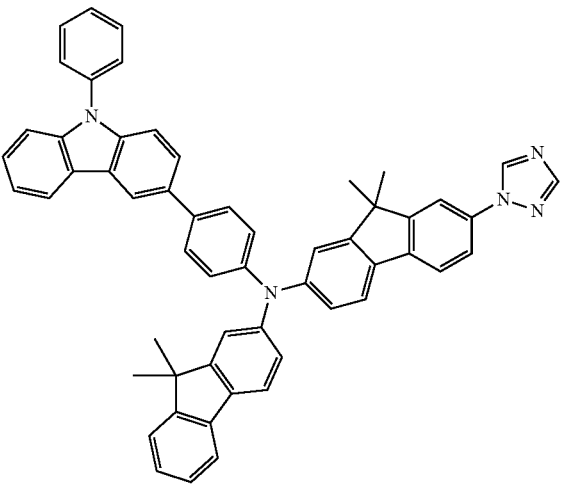

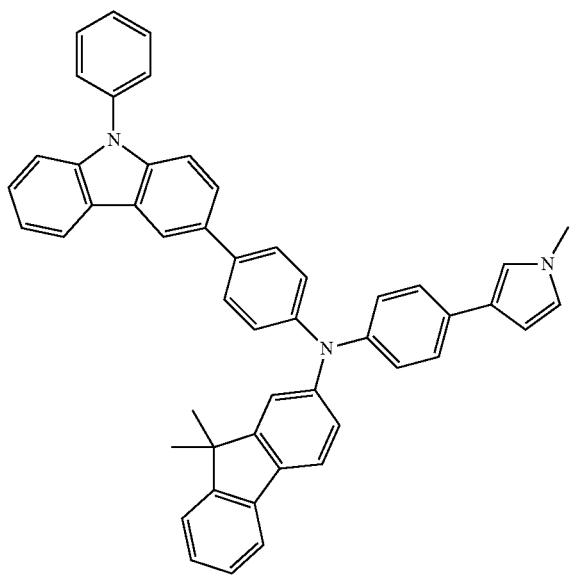

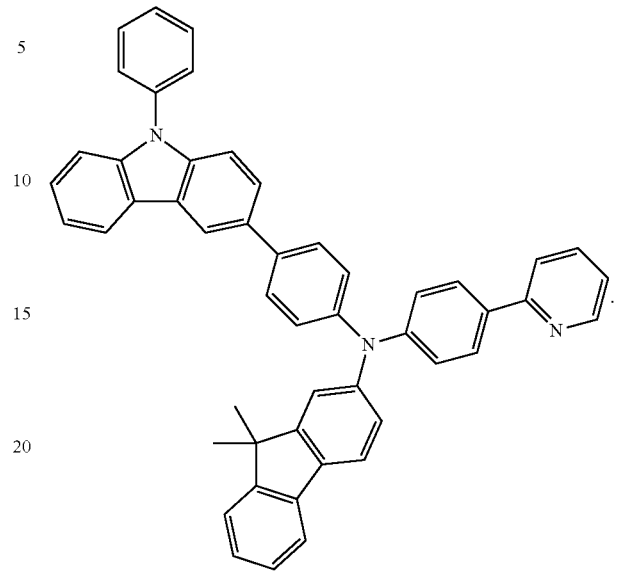

9. A carbazole-based compound of claim 1, with the following structure:

Compound 3

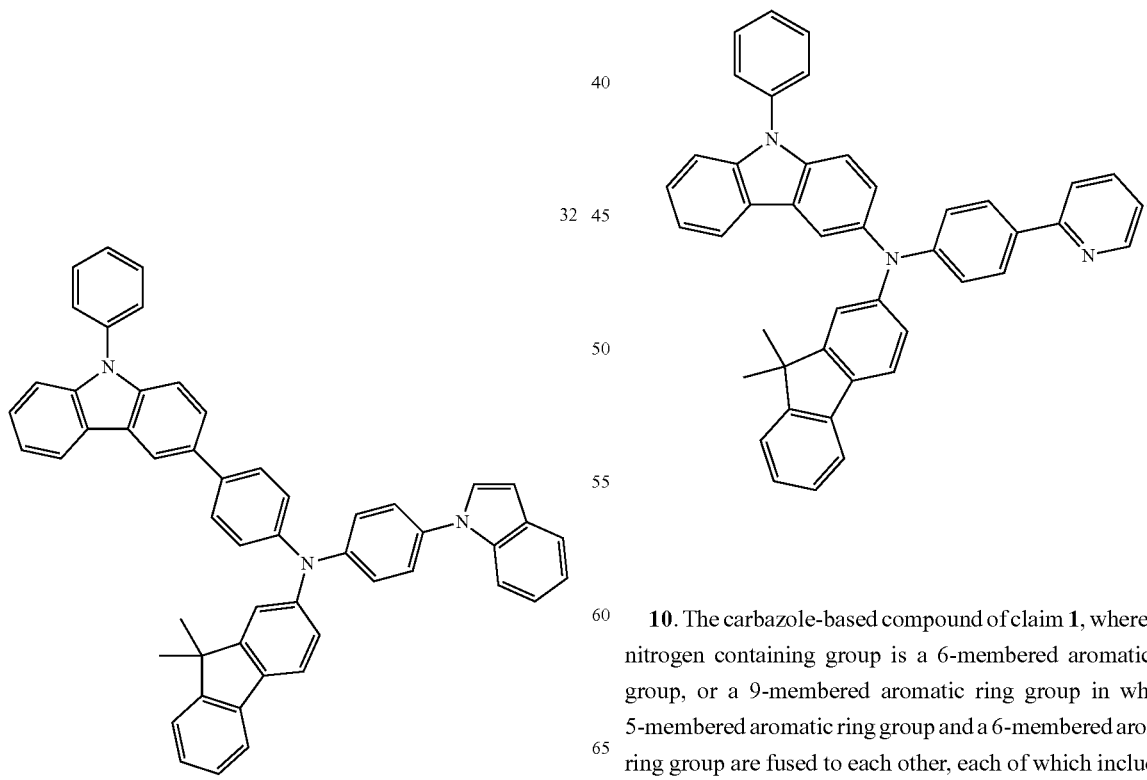

10. The carbazole-based compound of claim 1, wherein the nitrogen containing group is a 6-membered aromatic ring group, or a 9-membered aromatic ring group in which a 5-membered aromatic ring group and a 6-membered aromatic ring group are fused to each other, each of which includes at least one nitrogen atom as a ring atom.

11. A carbazole-based compound represented by Formula 1:

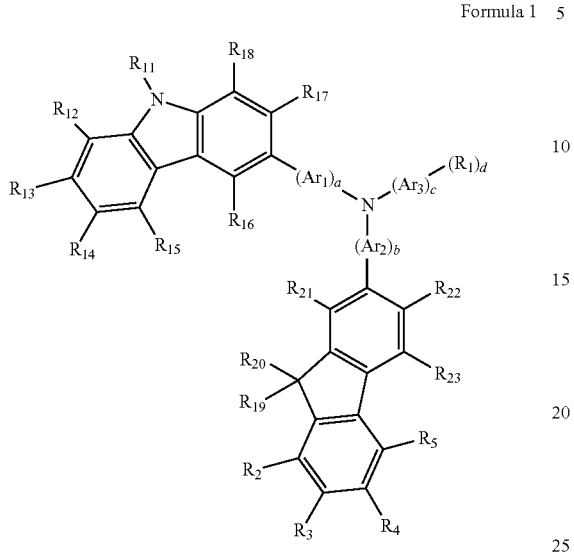

Formula 1 wherein $Ar_1$ to $Ar_3$ are each independently a substituted or unsubstituted $C_6$-$C_{60}$ arylene group;

a and b are each independently an integer from 0 to 5;

c is an integer from 1 to 5;

$R_1$ to $R_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{31}$)($R_{32}$)($R_{33}$), —N($R_{34}$)($R_{35}$) or a nitrogen-containing group, wherein at least one of $R_1$ or $R_3$ is a nitrogen-containing group;

d is an integer from 0 to 5;

$R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{36}$)($R_{37}$)($R_{38}$), or —N($R_{39}$)($R_{40}$);

$R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group; and the nitrogen-containing group is a 5-membered aromatic ring group, a 6-membered aromatic ring group, or a 9-membered aromatic ring group in which a 5-membered aromatic ring group and a 6-membered aromatic ring group are fused to each other, each of which includes at least one nitrogen atom as a ring atom, wherein the nitrogen-containing group is one of Formulae 4A to 4P below:

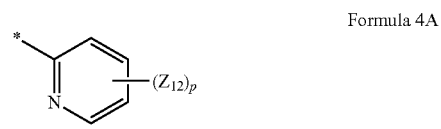

Formula 4A

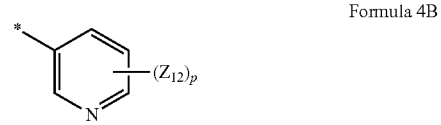

Formula 4B

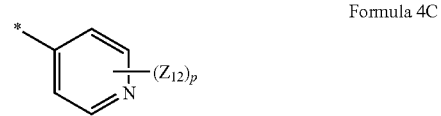

Formula 4C

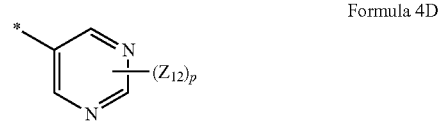

Formula 4D

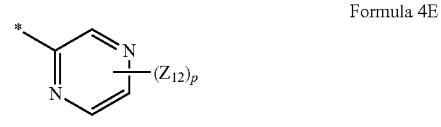

Formula 4E

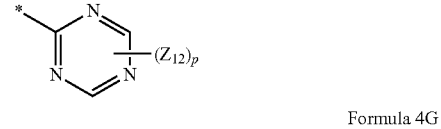

Formula 4F

Formula 4G

Formula 4H

Formula 4I

-continued

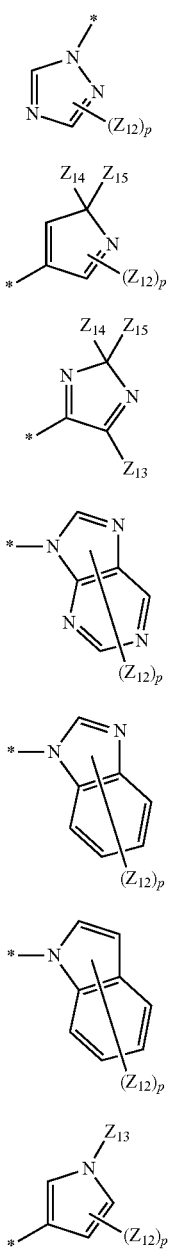

Formula 4J

Formula 4K

Formula 4L

Formula 4M

Formula 4N

Formula 4O

Formula 4P wherein $Z_{12}$, $Z_{13}$, $Z_{14}$ and $Z_{15}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group;

p is an integer from 1 to 6; and

* represents a chemical bond.

12. A carbazole-based compound represented by Formula 1:

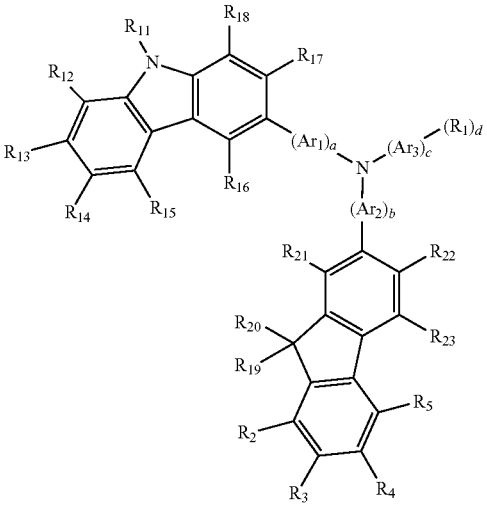

Formula 1 wherein $Ar_1$ to $Ar_3$ are each independently a substituted or unsubstituted $C_6$-$C_{60}$ arylene group;

a and b are each independently an integer from 0 to 5;

c is an integer from 1 to 5;

$R_1$ to $R_5$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{31}$)($R_{32}$)($R_{33}$), —N($R_{34}$)($R_{35}$) or a nitrogen-containing group, wherein at least one of $R_1$ or $R_3$ is a nitrogen-containing group;

d is an integer from 1 to 5;

$R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{36}$)($R_{37}$)($R_{38}$), or —N($R_{39}$)($R_{40}$);

$R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group; and the nitrogen-containing group is an unsubstituted 5-membered aromatic ring group, a 6-membered aromatic ring group, or a 9-membered aromatic ring group in which a 5-membered aromatic ring group and a 6-membered aromatic ring group are fused to each other, each of which includes at least one nitrogen atom as a ring atom, wherein at least one $R_1$ is a substituted or unsubstituted $C_5$-$C_{60}$ aryl group.

13. An organic light-emitting diode comprising a first electrode; a second electrode disposed opposite to the first electrode; and an organic layer interposed between the first electrode and the second electrode, wherein the organic layer comprises a carbazole-based compound according to claim 1.

14. The organic light emitting diode of claim 13, wherein the organic layer comprises at least one of a hole injection layer, a hole transport layer, a layer having both hole injecting and hole transporting capabilities, a buffer layer, an electron blocking layer, an emission layer, a hole blocking layer, an electron transport layer, an electron injection layer, or a layer having both electron injecting and electron transporting capabilities.

15. The organic light emitting diode of claim 14, wherein the organic layer comprises at least one of the hole injection layer, the hole transport layer, and the layer having both hole injecting and hole transporting capabilities, and the emission layer, wherein at least one of the hole injection layer, the hole transport layer, and the layer having both hole injecting and hole transporting capabilities comprises the carbazole-based compound.

16. The organic light emitting diode of claim 15, wherein at least one of the hole injection layer, the hole transport layer, and the layer having both hole injecting and hole transporting capabilities further comprises a bipolar compound that has higher hole mobility and higher conductivity than the carbazole-based compound.

17. The organic light emitting diode of claim 16, wherein the bipolar compound is represented by Formula 300 below:

Formula 300

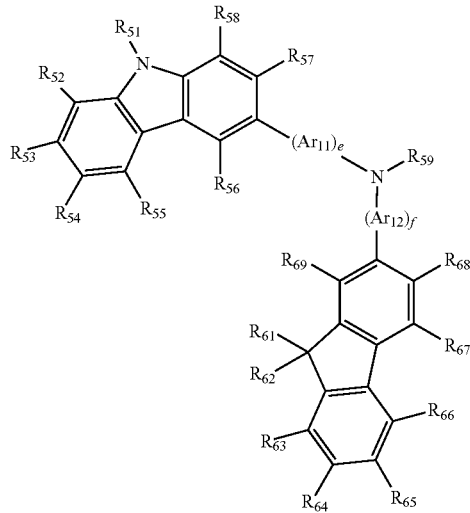

wherein $Ar_{11}$ and $Ar_{12}$ are each independently a substituted or unsubstituted $C_6$-$C_{60}$ arylene group;

e and f are each independently an integer from 0 to 5;

$R_{51}$ to $R_{58}$ and $R_{61}$ to $R_{69}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group; and $R_{59}$ is a phenyl group; a naphthyl group; an anthryl group; a biphenyl group; a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, or a substituted or unsubstituted $C_1$-$C_{20}$ alkoxy group.

18. The organic light emitting diode of claim 15, wherein at least one of the hole injection layer, the hole transport layer, or the layer having both hole injecting and hole transporting capabilities comprises a charge-generating material.

19. The organic light emitting diode of claim 15, wherein a buffer layer is interposed between at least one of the hole injection layer, the hole transport layer, or the layer having both hole injecting and hole transporting capabilities, and the emission layer.

20. The organic light emitting diode of claim 15, wherein the emission layer comprises a phosphorescent dopant.

21. The organic light emitting diode of claim 14, wherein the organic layer comprises an electron transport layer that comprises the carbazole-based compound.

22. The organic light emitting diode of claim 14, wherein the organic layer comprises an electron transport layer that comprises an electron transporting organic compound and a metal-containing material.

* * * * *